(12) United States Patent
Marques, Jr. et al.

(10) Patent No.: US 11,531,029 B2
(45) Date of Patent: Dec. 20, 2022

(54) **METHODS AND COMPOSITIONS FOR THE DETECTION OF *FLAVIVIRUS* INFECTIONS**

(71) Applicants: UNIVERSITY OF PITTSBURGH-OF THE COMMONWEALTH SYSTEM OF HIGHER EDUCATION, Pittsburgh, PA (US); YALE UNIVERSITY, New Haven, CT (US)

(72) Inventors: Ernesto Torres De Azeved Marques, Jr., Pittsburgh, PA (US); Eduardo Nascimento, Pittsburgh, PA (US); Albert Icksang Ko, New Haven, CT (US); Donald S. Burke, Pittsburgh, PA (US)

(73) Assignee: UNIVERSITY OF PITTSBURGH-OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 158 days.

(21) Appl. No.: 16/611,876

(22) PCT Filed: May 8, 2018

(86) PCT No.: PCT/US2018/031540
§ 371 (c)(1),
(2) Date: Nov. 8, 2019

(87) PCT Pub. No.: WO2018/208741
PCT Pub. Date: Nov. 15, 2018

(65) Prior Publication Data
US 2021/0181199 A1    Jun. 17, 2021

Related U.S. Application Data

(60) Provisional application No. 62/608,927, filed on Dec. 21, 2017, provisional application No. 62/503,201, filed on May 8, 2017.

(51) Int. Cl.
*G01N 33/569* (2006.01)
*G01N 33/563* (2006.01)
*G01N 33/68* (2006.01)

(52) U.S. Cl.
CPC ..... *G01N 33/56983* (2013.01); *G01N 33/563* (2013.01); *G01N 33/6854* (2013.01); *G01N 2333/185* (2013.01); *G01N 2469/20* (2013.01)

(58) Field of Classification Search
None
See application file for complete search history.

(56) References Cited

U.S. PATENT DOCUMENTS

| 4,452,901 A | 6/1984 | Gordon et al. |
| 5,424,000 A | 6/1995 | Winicov et al. |

(Continued)

FOREIGN PATENT DOCUMENTS

| TW | 201506405 | 2/2015 |
| WO | 2015/196192 | 12/2015 |
| WO | 2017/075596 | 5/2017 |

OTHER PUBLICATIONS

Rothman, Alan L. "Immunity to dengue virus: a tale of original antigenic sin and tropical cytokine storms." Nature Reviews Immunology 11.8 (2011): 532-543.

(Continued)

*Primary Examiner* — Michelle S Horning
(74) *Attorney, Agent, or Firm* — Meunier Carlin & Curfman LLC

(57) ABSTRACT

Disclosed are compositions and methods for the detection of a *Flavivirus* infection. In some embodiments, the method comprises detecting a recent *Flavivirus* infection by measuring the amount of anti-NS1 IgG3. In other embodiments, the method comprises detecting a prior Dengue virus infection in a subject previously immunized with a Dengue virus (Continued)

vaccine comprising one or more non-Dengue *Flavivirus* proteins.

20 Claims, 20 Drawing Sheets

Specification includes a Sequence Listing.

(56) References Cited

U.S. PATENT DOCUMENTS

| | | | |
|---|---|---|---|
| 2012/0009216 A1 | 1/2012 | Flamand et al. | |
| 2014/0050754 A1* | 2/2014 | Tong | A61K 39/12 435/5 |
| 2015/0196631 A1 | 7/2015 | Bouckenooghe et al. | |
| 2015/0265695 A1 | 9/2015 | Yao et al. | |
| 2017/0304426 A1 | 10/2017 | Tornieporth | |

OTHER PUBLICATIONS

Maggio et al., Enzyme-Immunoassay, (1987) and Nakamura, et al., Enzyme Immunoassays: Heterogeneous and Homogeneous Systems, Handbook of Experimental Immunology, vol. 1: Immunochemistry, 27.1-27.20 (1986).
Matsudaira, P. T., and D. R. Burgess. "SDS microslab linear gradient polyacrylamide gel electrophoresis." Analytical biochemistry 87.2 (1978): 386-396.
Neuhoff, Volker, Reinhard Stamm, and Hansjörg Eibl. "Clear background and highly sensitive protein staining with Coomassie Blue dyes in polyacrylamide gels: a systematic analysis." Electrophoresis 6.9 (1985): 427-448.
World Health Organization, 1997. Dengue hemorrhagic fever: diagnosis, treatment, prevention and control. Second edition. World Health Organization, Geneva, Switzerland., available at: http://www.who.int/csr/resources/publications/dengue/Denguepublication/en/ (accessed Feb. 5, 2018).
O'Connell, M. A., B. A. Belanger, and P. D. Haaland. "Calibration and assay development using the four-parameter logistic model." Chemometrics and Intelligent Laboratory Systems 20.2 (1993): 97-114.
International Search Report and Written Opinion dated Sep. 7, 2018, from International Application No. PCT/US2018/031540, 11 pages.
Rodrigo, et al. "Dengue virus neutralization is modulated by IgG antibody subclass and Fcγ receptor subtype", Virology 394 (2009) 175-182.
Lustig, et al. "Sensitivity and Kinetics of an NS1-Based Zika Virus Enzyme-Linked Immunosorbent Assay in Zika Virus-Infected Travelers from Israel, the Czech Republic, Italy, Belgium, Germany, and Chile", Journal of Clinical Microbiology, vol. 55, issue 6, pp. 1894-1901.
Brault, et al. "A Zika Vaccine Targeting NS1 Protein Protects Immunocompetent Adult Mice in a Lethal Challenge Model", Scientific Reports, 7: 14769, 11 pages.
Nascimento, et al. "Development of antibody biomarkers of long term and recent dengue virus infections", Journal of Virological Methods 257 (2018) 62-68.
Freire et al. "Mapping Putative B-Cell Zika Virus NS1 Epitopes Provides Molecular Basis for Anti-NS1 Antibody Discrimination between Zika and Dengue Viruses", ACS Omega 2017, 2, 3913-3920.
Ahmed, Nishat Hussain, and Shobha Broor. "Comparison of NS1 antigen detection ELISA, real time RT-PCR and virus isolation for rapid diagnosis of dengue infection in acute phase." Journal of vector borne diseases 51.3 (2014): 194.
Altschul, Stephen F., et al. "Basic local alignment search tool." Journal of Molecular Biology 215.3 (1990): 403-410.
Altschul, Stephen F., et al. "Gapped BLAST and PSI-BLAST: a new generation of protein database search programs." Nucleic acids research 25.17 (1997): 3389-3402.

Anderson, Leigh, and Norman G. Anderson. "High resolution two-dimensional electrophoresis of human plasma proteins." Proceedings of the National Academy of sciences 74.12 (1977): 5421-5425.
Beatty, P. Robert, et al. "Dengue virus NS1 triggers endothelial permeability and vascular leak that is prevented by NS1 vaccination." Science Translational Medicine 7.304 (2015): 304ra141-304ra141.
Brady, Oliver J., et al. "Refining the global spatial limits of dengue virus transmission by evidence-based consensus." PLoS Neglected Tropical Diseases 6.8 (2012).6:e1760.
Cordeiro, et al., "Characterization of a Dengue Patient Cohort in Recife, Brazil", Am. J. Trop. Med. Hyg., 2007, 77:1128-34.
Cordeiro, Marli Tenorio, et al. "Reliable classifier to differentiate primary and secondary acute dengue infection based on IgG ELISA." PloS One 4.4 (2009). e4945.
De Melo, Andréa Barbosa, et al. "Description of a prospective 17DD yellow fever vaccine cohort in Recife, Brazil." The American Journal of Tropical Medicine and Hygiene 85.4 (2011): 739-747.
Falconar, Andrew KI, and Paul R. Young. "Immunoaffinity purification of native dimer forms of the flavivirus non-structural glycoprotein, NS1." Journal of Virological Methods 30.3 (1990): 323-332.
Grange, Laura, et al. "Epidemiological risk factors associated with high global frequency of inapparent dengue virus infections." Frontiers in Immunology 5 (2014): 280.
Guy, Bruno, et al. "From research to phase III: preclinical, industrial and clinical development of the Sanofi Pasteur tetravalent dengue vaccine." Vaccine 29.42 (2011): 7229-7241.
Guzman, et al., "Dengue: a continuing global threat", Nat. Rev. Microbiol., 2010, 8:S7-16.
Henikoff, Steven, and Jorja G. Henikoff. "Amino acid substitution matrices from protein blocks." Proceedings of the National Academy of Sciences 89.22 (1992): 10915-10919.
Hernández-Ávila, Mauricio, and José Ignacio Santos-Preciado. "Análisis de la evidencia sobre eficacia y seguridad de la vacuna de dengue CYD-TDV y su potencial registro e implementación en el Programa de Vacunación Universal de México." salud pública de méxico 58.1 (2016): 71-83. English Abstract included in text.
ICH Harmonized Tripartite Guideline, 2005, Validation of analytical procedures: text and methodology Q2 (R1), available at: https://www.ich.org/fileadmin/Public_Web_Site/ICH_Products/Guidelines/Quality/Q2_R1/Step4/Q2_R1__Guideline.pdf (accessed Jan. 25, 2018).
Kaabinejadian, Saghar, et al. "Identification of class I HLA T cell control epitopes for West Nile virus." PloS One 8.6 (2013). e66298.
Karlin, Samuel, and Stephen F. Altschul. "Applications and statistics for multiple high-scoring segments in molecular sequences." Proceedings of the National Academy of Sciences 90.12 (1993): 5873-5877.
Kassanjee, Reshma, et al. "A new general biomarker-based incidence estimator." Epidemiology (Cambridge, Mass.) 23.5 (2012): 721-8.
Kassanjee, Reshma, et al. "Independent assessment of candidate HIV incidence assays on specimens in the CEPHIA repository." AIDS (London, England) 28.16 (2014): 2439-49.
Laemmli, Ulrich K. "Cleavage of structural proteins during the assembly of the head of bacteriophage T4." Nature 227.5259 (1970): 680-685.
Malisheni, Moffat, et al. "Clinical efficacy, safety, and immunogenicity of a live attenuated tetravalent dengue vaccine (CYD-TDV) in children: a systematic review with meta-analysis." Frontiers in Immunology 8 (2017): 863.
Modhiran, Naphak, et al. "Dengue virus NS1 protein activates cells via Toll-like receptor 4 and disrupts endothelial cell monolayer integrity." Science Translational Medicine 7.304 (2015): 304ra142-304ra142.
Moodie, Zoe, et al. "Neutralizing antibody correlates analysis of tetravalent dengue vaccine efficacy trials in Asia and Latin America." The Journal of Infectious Diseases 217.5 (2018): 742-753.
Neuhoff, Volker, et al. "Improved staining of proteins in polyacrylamide gels including isoelectric focusing gels with clear background at nanogram sensitivity using Coomassie Brilliant Blue G-250 and R-250." Electrophoresis 9.6 (1988): 255-262.

(56) References Cited

OTHER PUBLICATIONS

O'Farrell, Patrick H. "High resolution two-dimensional electrophoresis of proteins." Journal of Biological Chemistry 250.10 (1975): 4007-4021.
Olivera-Botello, Gustavo, et al. "Tetravalent dengue vaccine reduces symptomatic and asymptomatic dengue virus infections in healthy children and adolescents aged 2-16 years in Asia and Latin America." The Journal of Infectious Diseases 214.7 (2016): 994-1000.
Ornstein, Leonard. "Disc electrophoresis. I. Background and theory." Ann. NY Acad. Sci. 121.2 (1964): 321.
Peeling, Rosanna W., et al. "Evaluation of diagnostic tests: dengue." Nature Reviews Microbiology 8.12 (2010): S30-S37.
Promega, Gel Shift Assay FAQ, available at <http://www.promega.com/faq/gelshfaq.html> (last visited Mar. 25, 2005).
Quinn, Conrad P., et al. "Specific, sensitive, and quantitative enzyme-linked immunosorbent assay for human immunoglobulin G antibodies to anthrax toxin protective antigen." Emerging Infectious Diseases 8.10 (2002): 1103.
R package inctools, available from https://cran.r-project.org/web/packages/inctools/.
Roopenian, Derry C., and Shreeram Akilesh. "FcRn: the neonatal Fc receptor comes of age." Nature Reviews Immunology 7.9 (2007): 715-725.
Scherwitzl, Iris, Juthathip Mongkolsapaja, and Gavin Screaton. "Recent advances in human flavivirus vaccines." Current Opinion in Virology 23 (2017): 95-101.
Seaton, Kelly E., et al. "Computational analysis of antibody dynamics identifies recent HIV-1 infection." JCI Insight 2.24 (2017). 94355.
Shu, Pei-Yun, et al. "Dengue NS1-specific antibody responses: Isotype distribution and serotyping in patients with dengue fever and dengue hemorrhagic fever." Journal of Medical Virology 62.2 (2000): 224-232.
Simmons, et al., "Dengue", N. Engl J. Med., 2012, 366:1423-32.
Stapleton, et. al., "Competition for FcRn-mediated Transport Gives Rise to Short Half-Life of Human IgG3 and Offers Therapeutic Potential", Nat. Commun., Dec. 20, 2011; 2:599.
Timiryasova, Tatyana M., et al. "Optimization and validation of a plaque reduction neutralization test for the detection of neutralizing antibodies to four serotypes of dengue virus used in support of dengue vaccine development." The American Journal of Tropical Medicine and Hygiene 88.5 (2013): 962-970.
Vidarsson, Gestur, Gillian Dekkers, and Theo Rispens. "IgG subclasses and allotypes: from structure to effector functions." Frontiers in Immunology 5 (2014): 520.
Watterson, Daniel, Naphak Modhiran, and Paul R. Young. "The many faces of the flavivirus NS1 protein offer a multitude of options for inhibitor design." Antiviral Research 130 (2016): 7-18.
Yates, Nicole L., et al. "Multiple HIV-1-specific IgG3 responses decline during acute HIV-1: implications for detection of incident HIV infection." AIDS (London, England) 25.17 (2011): 2089.

\* cited by examiner

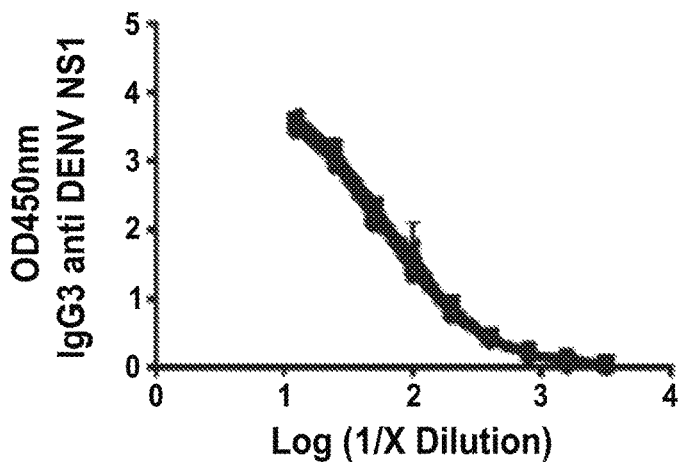
FIG. 2B
| Statistical parameters | Total IgG | | | IgG3 | | |
|---|---|---|---|---|---|---|
| | Mean | SD | %CV | Mean | SD | %CV |
| Upper asymptote | 4.08 | 0.08 | 2% | 4.20 | 0.08 | 2% |
| Lower asymptote | 0.14 | 0.02 | 16% | 0.01 | 0.03 | 233% |
| Slope | -1.38 | 0.07 | 5% | -1.13 | 0.05 | 5% |
| EC50 | 869.20 | 103.3 | 12% | 58.61 | 4.40 | 8% |
FIG. 2C
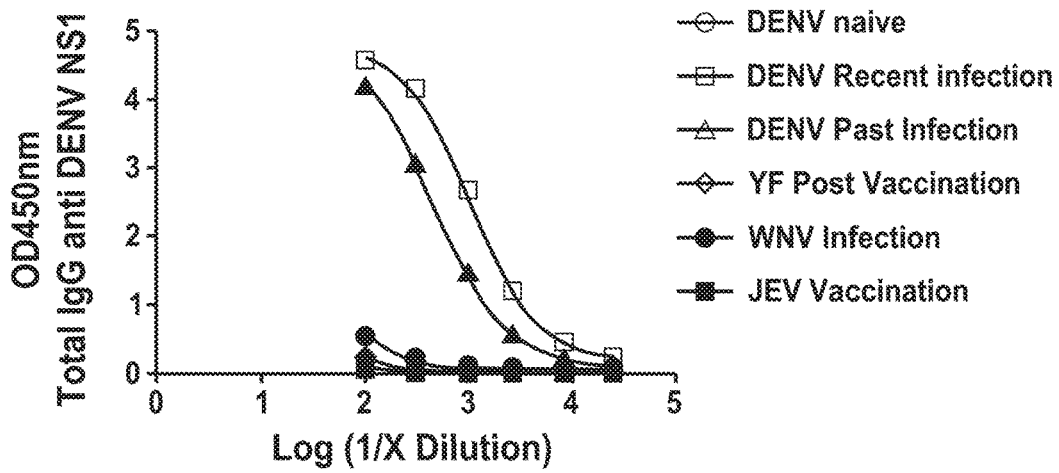
FIG. 2D Table 1: General participant demographics.

| Groups | Number of Patients (%) | Primary infection | | | | Total (%) |
|---|---|---|---|---|---|---|
| | | DF (%) | DFC (%) | DHF (%) | D (%) | |
| *All* | 266(100%) | 24(9.0%) | 34(12.8%) | 5(1.9%) | 11(4.1%) | 74(27.8%) |
| *Adults* | 170(64%) | 9(3.4%) | 19(7.1%) | 5(1.9%) | 9(3.4%) | 42(15.8%) |
| Male | 80(30%) | 2(0.8%) | 9(3.4%) | 1(0.4%) | 5(1.9%) | 17(6.5%) |
| Female | 90(34%) | 7(2.6%) | 10(3.8%) | 4(1.5%) | 4(1.5%) | 25(9.4%) |
| *Children* | 96(36%) | 15(5.6%) | 15(5.6%) | 0(0.0%) | 2(0.8%) | 32(12.0%) |
| Male | 48(18%) | 6(2.3%) | 8(3.0%) | 0(0.0%) | 0(0.0%) | 14(5.3%) |
| Female | 48(18%) | 9(3.4%) | 7(2.6%) | 0(0.0%) | 2(0.8%) | 18(6.8%) |

D - Confirmed dengue cases where clinical diagnosis could not be determined due to the lack of clinical and/or laboratory data.

DF - dengue fever; DFC - complicated dengue fever; DHF - dengue hemorrhagic fever Adults - ≥18 years old; Children< 18 years old

FIG. 7

| Secondary infection | | | | |
|---|---|---|---|---|
| DF (%) | DFC (%) | DHF (%) | D (%) | Total (%) |
| 84(31.6%) | 83(31.2%) | 10(3.8%) | 15(5.6%) | 192(72.2%) |
| 39(14.7%) | 67(25.2%) | 8(3.0%) | 14(5.3%) | 128(48.2%) |
| 16(6.0%) | 37(13.9%) | 2(0.8%) | 8(3.0%) | 63(23.7%) |
| 23(8.6%) | 30(11.3%) | 6(2.3%) | 6(2.3%) | 65(24.4%) |
| 45(16.9%) | 16(6.0%) | 2(0.8%) | 1(0.4%) | 64(24.1%) |
| 23(8.6%) | 9(3.4%) | 1(0.4%) | 1(0.4%) | 34(12.8%) |
| 22(8.3%) | 7(2.6%) | 1(0.4%) | 0(0.0%) | 30(11.3%) |

FIG. 7 Cont.

Table 2. Comparison on anti-dengue NS1-specific total IgG and IgG3 detection between primary and secondary dengue infections.

| Groups | Total anti-dengue NS1 IgG | | | | |
|---|---|---|---|---|---|
| | 1st (%) | 2nd (%) | OR | 95% CI | P |
| *All individuals (n)* | 74 | 192 | | | |
| *Positive* | 73(98.6%) | 192(100.0%) | – | – | – |
| *Negative* | 1(1.4%) | 0(0.0%) | | | |
| *Undetermined\** | 0(0.0%) | 0(0.0%) | | | |
| *Adults (n)* | 42 | 128 | | | |
| *Positive* | 42(100.0%) | 128(100.0%) | – | – | – |
| *Negative* | 00(0.0%) | 0(0.0%) | | | |
| *Undetermined\** | 00(0.0%) | 0(0.0%) | | | |
| *Children (n)* | 32 | 64 | | | |
| *Positive* | 31(96.9%) | 64(100.0%) | – | – | – |
| *Negative* | 1(3.1%) | 0(0.0%) | | | |
| *Undetermined\** | 00(0.0%) | 0(0.0%) | | | |

\* Test was undetermined because the timing the blood draw took place was either too early (<10 days post onset of symptoms) or too late (>90 days post onset of symptoms) to detect antigen-specific IgG3

1st - primary dengue infection; 2nd - secondary dengue infection

OR (odds ratio), 95% CI (confidence interval) and $p$ were calculated using Fisher's t test.

FIG. 8

| anti-dengue NS1 IgG3 | | | | |
|---|---|---|---|---|
| 1st (%) | 2nd (%) | OR | 95% CI | P |
| 74 | 192 | | | |
| 65(87.9%) | 143(74.5%) | 3.8 | 1.1 to 12.2 | 0.025 |
| 3(4.0%) | 25(13.0%) | | | |
| 6(8.1%) | 24(12.5%) | | | |
| 42 | 128 | | | |
| 39(92.9%) | 102(79.7%) | 5.4 | 0.8 to 58.2 | 0.117 |
| 1(2.4%) | 14(10.9%) | | | |
| 2(4.8%) | 12(9.4%) | | | |
| 32 | 64 | | | |
| 26(81.3%) | 41(64.1%) | 3.5 | 0.8 to 16.6 | 0.125 |
| 2(6.3%) | 11(17.2%) | | | |
| 4(12.5%) | 12(18.8%) | | | |

FIG. 8 Cont.

Table 3. Comparison of anti-dengue NS1-specific total IgG and IgG3 detection between mild (DF) and severe (DFC+DHF) dengue clinical manifestations.

| Groups | Anti-dengue NS1 total IgG | | | | |
| --- | --- | --- | --- | --- | --- |
| | DF (%) | DFC (%) | DHF (%) | OR | 95% CI |
| *All individuals (n)* | 108 | 117 | 15 | | |
| *Positive* | 108(100.0%) | 116(99.1%) | 15(100.0%) | – | – |
| *Negative* | 0(0.0%) | 1(0.9%) | 0(0.0%) | | |
| *Undetermined\** | 0(0.0%) | 0(0.0%) | 0(0.0%) | | |
| *Adults (n)* | 48 | 86 | 13 | | |
| *Positive* | 48(100.0%) | 86(100.0%) | 15(100.0%) | | |
| *Negative* | 0(0.0%) | 0(0.0%) | 0(0.0%) | | |
| *Undetermined\** | 0(0.0%) | 0(0.0%) | 0(0.0%) | | |
| *Children (n)* | 60 | 31 | 2 | | |
| *Positive* | 60(100.0%) | 30(96.8%) | 2(100.0%) | | |
| *Negative* | 0(0.0%) | 1(3.2%) | 0(0.0%) | | |
| *Undetermined\** | 0(0.0%) | 0(0.0%) | 0(0.0%) | | |

\* Analysis was performed between DF and DFC+DHF.

FIG. 9

| p | Anti-dengue NS1 total IgG3 | | | OR* | 95% CI* | p* |
|---|---|---|---|---|---|---|
| | DF (%) | DFC (%) | DHF (%) | | | |
| | 108 | 117 | 15 | | | |
| | 80(74.1%) | 97(82.9%) | 11(73.3%) | 0.49 | 0.21-1.13 | 0.133 |
| | 15(13.9%) | 8(6.8%) | 2(13.3%) | | | |
| | 13(12.0) | 12(10.3%) | 2(13.3%) | | | |
| | 48 | 86 | 13 | | | |
| | 40(83.3%) | 73(84.9%) | 11(84.6%) | 1.42 | 0.40-5.10 | 0.75 |
| | 3(6.3%) | 7(8.1%) | 2(15.4%) | | | |
| | 5(10.4%) | 6(7.0%) | 0(0.0%) | | | |
| | 60 | 31 | 2 | | | |
| | 40(66.7%) | 24(77.4%) | 0(0.0%) | 0.13 | 0.01-0.89 | 0.050 |
| | 12(20.0%) | 1(3.2%) | 0(0.0%) | | | |
| | 8(13.3%) | 6(19.4%) | 2(100.0%) | | | |

FIG. 9 Cont.

Table 4. Performance and limit ranges of the IVIG reference curve

| Reference Parameter | Number of Measurements | GM[2] | %GCV[3] | Acceptable Limits Lower | Upper |
|---|---|---|---|---|---|
| Unit Value | 104 | 863.3 | 12.4% | N/A[6] | N/A[6] |
| Upper Asymptote (OD)[1] | 350 | 3.83 | 6.2% | >3.203 | N/A[4] |
| Lower Asymptote (OD) | 350 | 0.15 | 55.7% | N/A[5] | <0.579 |
| Slope | 352 | 1.43 | 11.8% | 1.020 | 1.997 |

[1] OD – Optical density

[2] GM – Geometric Mean

[3] %GCV – coefficient of variance of data after log-normal transformation

[4] Upper limit for upper asymptote not calculated as it can be artificially high

[5] Lower limit for lower asymptote not calculated as it can be artificially low or negative

[6] Acceptable limits are not applicable to the unit value assignment

FIG. 10

Table 5. Performance characteristics for positive and negative control samples.

| Internal Quality Control | Number of measurements | Geometric Mean Concentration (EU/mL) | %GCV[1] | Acceptable Limits | |
|---|---|---|---|---|---|
| | | | | Lower | Upper |
| High | 456 | 2985.4 | 17.9% | 2147.9 | 4149.4 |
| Mid | 461 | 805.9 | 16.8% | 591.2 | 1098.5 |
| Low | 406 | 82.2 | 16.6% | 58.3 | 108.0 |
| Negative | 217 | 2.0 | N/A[2] | N/A[3] | <9 |

[1] %GCV – coefficient of variance of data after log-normal transformation.

[2] Not estimated for negative control as concentrations reported are below the LLOQ.

[3] Lower limit for negative sample was not calculated as it can be artificially low.

FIG. 11

Table 6. Evaluation of accuracy of the anti-dengue NS1 IgG ELISA.

| Sample | Percent Spike | Expected Value (EU/mL) | GMC1 (EU/mL) | Percent Recovery (%) |
|---|---|---|---|---|
| 1 | 100% | 863.3 | 884.0 | 102% |
| 2 | 50% | 432.8 | 456.1 | 105% |
| 3 | 25% | 217.6 | 214.8 | 99% |
| 4 | 12.50% | 109.9 | 106.4 | 97% |
| 5 | 6.25% | 93.1 | 84.6 | 91% |
| 6 | 10.80% | 56.5 | 53.8 | 95% |
| 7 | 5.40% | 46.6 | 42.3 | 91% |
| 8 | 2.71% | 23.4 | 22.6 | 97% |
| 9 | 1.37% | 11.8 | 10.4 | 89% |
| 10 | 0.66% | 5.7 | 6.5 | 114% |

[1]GMC – Geometric Mean Concentration.

FIG. 12

Table 7. Verification of lower limit of quantitation (LLOQ) of the anti-dengue NS1 IgG ELISA.

| Sample Range | Number of Samples | Intermediate Precision | 95% Confidence Interval | |
|---|---|---|---|---|
| | | | Lower Limit | Upper Limit |
| <9 EU/mL (below LLOQ) | 6 | 18.5% | 14.2% | 26.5% |
| 9–30 EU/mL (near LLOQ) | 9 | 13.8% | 11.5% | 17.3% |
| 30–100 EU/mL (above LLOQ) | 10 | 14.0% | 11.9% | 16.9% |

FIG. 13

Table 8. Evaluation of specificity of anti-dengue NS1 IgG ELISA with samples positive to other related flaviviruses.

| Description | N | GMC in EU/mL (95% CI) |
|---|---|---|
| Post JEV Vaccine | 31 | 4.7 (4.4, 5.1) |
| Post YFV Vaccine | 36 | 6.6 (5.5, 7.9) |
| Post WNV Infection | 3 | 51.0 (1.3, 1946.4)[1] |
| Post-ZIKV Infection | 4 | 21.9 (7.8, 61.6)[2] |

[1] The NS1 IgG results of the 3 samples are 16.3, 30.5, and 266.5 EU/mL
[2] The NS1 IgG results of the 4 samples are 10.4, 18.2, 24.8, and 49.3 EU/mL

FIG. 14

Table 9. M13 anti-dengue NS1 IgG ELISA serostatus classification of baseline (M0) antidengue NS1 IgG seronegative or seropositive participants who did not have symptomatic VCD infection between first and last injection.

| Classification by anti-dengue NS1 IgG ELISA at M0 (threshold of 9 EU/mL) | Treatment Group | Classification by anti-dengue NS1 IgG ELISA at M13 (threshold of 9 EU/mL) | | | p-value[2] |
|---|---|---|---|---|---|
| | | Seropositive | Seronegative | Total | |
| Seronegative | Control | 39 (11.6%) | 298 (88.4%) | 337 | 0.0009 |
| | Vaccine[1] | 139 (19.9%) | 560 (80.1%) | 699 | |
| Seropositive | Control | 860 (96.7%) | 29 (3.3%) | 889 | 0.1495 |
| | Vaccine[1] | 1770 (97.7%) | 42 (2.3%) | 1812 | |

[1]Participants classified as vaccine group if they received at least 1 injection of dengue vaccine

[2]p-valued from Chi-square test

FIG. 15

```
SEQUENCE LISTING

<160> NUMBER OF SEQ ID NOS: 6

<210> SEQ ID NO 1
<211> LENGTH: 352
<212> TYPE: PRT
<213> ORGANISM: Dengue virus 1

<400> SEQUENCE: 1

Asp Ser Gly Cys Val Ile Asn Trp Lys Gly Arg Glu Leu Lys Cys Gly
1               5                   10                  15

Ser Gly Ile Phe Val Thr Asn Glu Val His Thr Trp Thr Glu Gln Tyr
            20                  25                  30

Lys Phe Gln Ala Asp Ser Pro Lys Arg Leu Ser Ala Ala Ile Gly Lys
        35                  40                  45

Ala Trp Glu Glu Gly Val Cys Gly Ile Arg Ser Ala Thr Arg Leu Glu
    50                  55                  60

Asn Ile Met Trp Lys Gln Ile Ser Asn Glu Leu Asn His Ile Leu Leu
65                  70                  75                  80

Glu Asn Asp Met Lys Phe Thr Val Val Gly Asp Val Ser Gly Ile
                85                  90                  95

Leu Ala Gln Gly Lys Lys Met Ile Arg Pro Gln Pro Met Glu His Lys
            100                 105                 110

Tyr Ser Trp Lys Ser Trp Gly Lys Ala Lys Ile Ile Gly Ala Asp Val
        115                 120                 125

Gln Asn Thr Thr Phe Ile Ile Asp Gly Pro Asn Thr Pro Glu Cys Pro
    130                 135                 140

Asp Asn Gln Arg Ala Trp Asn Ile Trp Glu Val Glu Asp Tyr Gly Phe
145                 150                 155                 160

Gly Ile Phe Thr Thr Asn Ile Trp Leu Lys Leu Arg Asp Ser Tyr Thr
                165                 170                 175

Gln Val Cys Asp His Arg Leu Met Ser Ala Ala Ile Lys Asp Ser Lys
            180                 185                 190

Ala Val His Ala Asp Met Gly Tyr Trp Ile Glu Ser Glu Lys Asn Glu
        195                 200                 205

Thr Trp Lys Leu Ala Arg Ala Ser Phe Ile Glu Val Lys Thr Cys Ile
    210                 215                 220
```

```
Trp Pro Lys Ser His Thr Leu Trp Ser Asn Gly Val Leu Glu Ser Glu
225                 230                 235                 240

Met Ile Ile Pro Lys Ile Tyr Gly Gly Pro Ile Ser Gln His Asn Tyr
            245                 250                 255

Arg Pro Gly Tyr Phe Thr Gln Thr Ala Gly Pro Trp His Leu Gly Lys
        260                 265                 270

Leu Glu Leu Asp Phe Asp Leu Cys Glu Gly Thr Thr Val Val Val Asp
    275                 280                 285

Glu His Cys Gly Asn Arg Gly Pro Ser Leu Arg Thr Thr Thr Val Thr
290                 295                 300

Gly Lys Thr Ile His Glu Trp Cys Cys Arg Ser Cys Thr Leu Pro Pro
305                 310                 315                 320

Leu Arg Phe Lys Gly Glu Asp Gly Cys Trp Tyr Gly Met Glu Ile Arg
            325                 330                 335

Pro Val Lys Glu Lys Glu Glu Asn Leu Val Lys Ser Met Val Ser Ala
            340                 345                 350

<210> SEQ ID NO 2
<211> LENGTH: 351
<212> TYPE: PRT
<213> ORGANISM: Dengue virus 2

<400> SEQUENCE: 2

Asp Ser Gly Cys Val Val Ser Trp Lys Asn Lys Glu Leu Lys Cys Gly
1               5                   10                  15

Ser Gly Ile Phe Ile Thr Asp Asn Val His Thr Trp Thr Glu Gln Tyr
            20                  25                  30

Lys Phe Gln Pro Glu Ser Pro Ser Lys Leu Ala Ser Ala Ile Gln Lys
        35                  40                  45

Ala His Glu Glu Gly Ile Cys Gly Ile Arg Ser Val Thr Arg Leu Glu
    50                  55                  60

Asn Leu Met Trp Lys Gln Ile Thr Pro Glu Leu Asn His Ile Leu Ser
65                  70                  75                  80

Glu Asn Glu Val Lys Leu Thr Ile Met Thr Gly Asp Ile Lys Gly Ile
                85                  90                  95

Met Gln Ala Gly Lys Arg Ser Leu Arg Pro Gln Pro Thr Glu Leu Lys
            100                 105                 110

Tyr Ser Trp Lys Thr Trp Gly Lys Ala Lys Met Leu Ser Thr Glu Ser
        115                 120                 125

His Asn Gln Thr Phe Leu Ile Asp Gly Pro Glu Thr Ala Glu Cys Pro
    130                 135                 140

Asn Thr Asn Arg Ala Trp Asn Ser Leu Glu Val Glu Asp Tyr Gly Phe
145                 150                 155                 160

Gly Val Phe Thr Thr Asn Ile Trp Leu Lys Leu Lys Glu Lys Gln Asp
                165                 170                 175

Val Phe Cys Asp Ser Lys Leu Met Ser Ala Ala Ile Lys Asp Asn Arg
            180                 185                 190

Ala Val His Ala Asp Met Gly Tyr Trp Ile Glu Ser Ala Leu Asn Asp
        195                 200                 205

Thr Trp Lys Ile Glu Lys Ala Ser Phe Ile Glu Val Lys Asn Cys His
    210                 215                 220

Trp Pro Lys Ser His Thr Leu Trp Ser Gly Val Leu Glu Ser Glu Met
225                 230                 235                 240

Ile Ile Pro Lys Asn Leu Ala Gly Pro Val Ser Gln His Asn Tyr Arg
                245                 250                 255
```

```
Pro Gly Tyr His Thr Gln Ile Thr Gly Pro Trp His Leu Gly Lys Leu
            260                 265                 270

Glu Met Asp Phe Asp Phe Cys Asp Gly Thr Thr Val Val Thr Glu
        275                 280                 285

Asp Cys Gly Asn Arg Gly Pro Ser Leu Arg Thr Thr Thr Ala Ser Gly
290                 295                 300

Lys Leu Ile Thr Glu Trp Cys Cys Arg Ser Cys Thr Leu Pro Pro Leu
305                 310                 315                 320

Arg Tyr Arg Gly Glu Asp Gly Cys Trp Tyr Gly Met Glu Ile Arg Pro
            325                 330                 335

Leu Lys Glu Lys Glu Glu Asn Leu Val Asn Ser Leu Val Thr Ala
        340                 345                 350

<210> SEQ ID NO 3
<211> LENGTH: 352
<212> TYPE: PRT
<213> ORGANISM: Dengue virus 3

<400> SEQUENCE: 3

Asp Met Gly Cys Val Ile Asn Trp Lys Gly Lys Glu Leu Lys Cys Gly
1               5                   10                  15

Ser Gly Ile Phe Val Thr Asn Glu Val His Thr Trp Thr Glu Gln Tyr
            20                  25                  30

Lys Phe Gln Ala Asp Ser Pro Lys Arg Leu Ala Thr Ala Ile Ala Gly
        35                  40                  45

Ala Trp Glu Asn Gly Val Cys Gly Ile Arg Ser Thr Thr Arg Met Glu
    50                  55                  60

Asn Leu Leu Trp Lys Gln Ile Ala Asn Glu Leu Asn Tyr Ile Leu Trp
65                  70                  75                  80

Glu Asn Asn Ile Lys Leu Thr Val Val Val Gly Asp Thr Leu Gly Val
                85                  90                  95

Leu Glu Gln Gly Lys Arg Thr Leu Thr Pro Gln Pro Met Glu Leu Lys
            100                 105                 110

Tyr Ser Trp Lys Thr Trp Gly Lys Ala Lys Ile Val Thr Ala Glu Thr
        115                 120                 125

Gln Asn Ser Ser Phe Ile Ile Asp Gly Pro Asn Thr Pro Glu Cys Pro
    130                 135                 140

Ser Ala Ser Arg Ala Trp Asn Val Trp Glu Val Glu Asp Tyr Gly Phe
145                 150                 155                 160

Gly Val Phe Thr Thr Asn Ile Trp Leu Lys Leu Arg Glu Val Tyr Thr
                165                 170                 175

Gln Leu Cys Asp His Arg Leu Met Ser Ala Ala Val Lys Asp Glu Arg
            180                 185                 190

Ala Val His Ala Asp Met Gly Tyr Trp Ile Glu Ser Gln Lys Asn Gly
        195                 200                 205

Ser Trp Lys Leu Glu Lys Ala Ser Leu Ile Glu Val Lys Thr Cys Thr
    210                 215                 220

Trp Pro Lys Ser His Thr Leu Trp Thr Asn Gly Val Leu Glu Ser Asp
225                 230                 235                 240

Met Ile Ile Pro Lys Ser Leu Ala Gly Pro Ile Ser Gln His Asn Tyr
                245                 250                 255

Arg Pro Gly Tyr His Thr Gln Thr Ala Gly Pro Trp His Leu Gly Lys
            260                 265                 270

Leu Glu Leu Asp Phe Asn Tyr Cys Glu Gly Thr Thr Val Val Ile Thr
```

```
                    275                 280                 285
Glu Ser Cys Gly Thr Arg Gly Pro Ser Leu Arg Thr Thr Val Ser
    290                 295                 300

Gly Lys Leu Ile His Glu Trp Cys Cys Arg Ser Cys Thr Leu Pro Pro
305                 310                 315                 320

Leu Arg Tyr Met Gly Glu Asp Gly Cys Trp Tyr Gly Met Glu Ile Arg
                    325                 330                 335

Pro Ile Ser Glu Lys Glu Glu Asn Met Val Lys Ser Leu Val Ser Ala
                340                 345                 350

<210> SEQ ID NO 4
<211> LENGTH: 352
<212> TYPE: PRT
<213> ORGANISM: Dengue virus 4

<400> SEQUENCE: 4

Asp Met Gly Cys Val Ala Ser Trp Ser Gly Lys Glu Leu Lys Cys Gly
1               5                   10                  15

Ser Gly Ile Phe Val Val Asp Asn Val His Thr Trp Thr Glu Gln Tyr
            20                  25                  30

Lys Phe Gln Pro Glu Ser Pro Ala Arg Leu Ala Ser Ala Ile Leu Asn
        35                  40                  45

Ala His Lys Asp Gly Val Cys Gly Ile Arg Ser Thr Thr Arg Leu Glu
    50                  55                  60

Asn Val Met Trp Lys Gln Ile Thr Asn Glu Leu Asn Tyr Val Leu Trp
65                  70                  75                  80

Glu Gly Gly His Asp Leu Thr Val Val Ala Gly Asp Val Lys Gly Val
                85                  90                  95

Leu Thr Lys Gly Lys Arg Ala Leu Thr Pro Pro Val Ser Asp Leu Lys
            100                 105                 110

Tyr Ser Trp Lys Thr Trp Gly Lys Ala Lys Ile Phe Thr Pro Glu Ala
        115                 120                 125

Arg Asn Ser Thr Phe Leu Ile Asp Gly Pro Asp Thr Ser Glu Cys Pro
    130                 135                 140

Asn Glu Arg Arg Ala Trp Asn Ser Leu Glu Val Glu Asp Tyr Gly Phe
145                 150                 155                 160

Gly Met Phe Thr Thr Asn Ile Trp Met Lys Phe Arg Glu Gly Ser Ser
                165                 170                 175

Glu Val Cys Asp His Arg Leu Met Ser Ala Ala Ile Lys Asp Gln Lys
            180                 185                 190

Ala Val His Ala Asp Met Gly Tyr Trp Ile Glu Ser Ser Lys Asn Gln
        195                 200                 205

Thr Trp Gln Ile Glu Lys Ala Ser Leu Ile Glu Val Lys Thr Cys Leu
    210                 215                 220

Trp Pro Lys Thr His Thr Leu Trp Ser Asn Gly Val Leu Glu Ser Gln
225                 230                 235                 240

Met Leu Ile Pro Lys Ser Tyr Ala Gly Pro Phe Ser Gln His Asn Tyr
                245                 250                 255

Arg Gln Gly Tyr Ala Thr Gln Thr Val Gly Pro Trp His Leu Gly Lys
            260                 265                 270

Leu Glu Ile Asp Phe Gly Glu Cys Pro Gly Thr Thr Val Thr Ile Gln
        275                 280                 285

Glu Asp Cys Asp His Arg Gly Pro Ser Leu Arg Thr Thr Thr Ala Ser
    290                 295                 300
```

```
Gly Lys Leu Val Thr Gln Trp Cys Cys Arg Ser Cys Thr Met Pro Pro
305                 310                 315                 320

Leu Arg Phe Leu Gly Glu Asp Gly Cys Trp Tyr Gly Met Glu Ile Arg
                325                 330                 335

Pro Leu Ser Glu Lys Glu Glu Asn Met Val Lys Ser Gln Val Thr Ala
            340                 345                 350

<210> SEQ ID NO 5
<211> LENGTH: 352
<212> TYPE: PRT
<213> ORGANISM: Yellow fever virus

<400> SEQUENCE: 5

Asp Gln Gly Cys Ala Ile Asn Phe Gly Lys Arg Glu Leu Lys Cys Gly
1               5                   10                  15

Asp Gly Ile Phe Ile Phe Arg Asp Ser Asp Asp Trp Leu Asn Lys Tyr
            20                  25                  30

Ser Tyr Tyr Pro Glu Asp Pro Val Lys Leu Ala Ser Ile Val Lys Ala
        35                  40                  45

Ser Phe Glu Glu Gly Lys Cys Gly Leu Asn Ser Val Asp Ser Leu Glu
50                  55                  60

His Glu Met Trp Arg Ser Arg Ala Asp Glu Ile Asn Ala Ile Phe Glu
65                  70                  75                  80

Glu Asn Glu Val Asp Ile Ser Val Val Gln Asp Pro Lys Asn Val
                85                  90                  95

Tyr Gln Arg Gly Thr His Pro Phe Ser Arg Ile Arg Asp Gly Leu Gln
            100                 105                 110

Tyr Gly Trp Lys Thr Trp Gly Lys Asn Leu Val Phe Ser Pro Gly Arg
        115                 120                 125

Lys Asn Gly Ser Phe Ile Ile Asp Gly Lys Ser Arg Lys Glu Cys Pro
130                 135                 140

Phe Ser Asn Arg Val Trp Asn Ser Phe Gln Ile Glu Glu Phe Gly Thr
145                 150                 155                 160

Gly Val Phe Thr Thr Arg Val Tyr Met Asp Ala Val Phe Glu Tyr Thr
                165                 170                 175

Ile Asp Cys Asp Gly Ser Ile Leu Gly Ala Ala Val Asn Gly Lys Lys
            180                 185                 190

Ser Ala His Gly Ser Pro Thr Phe Trp Met Gly Ser His Glu Val Asn
        195                 200                 205

Gly Thr Trp Met Ile His Thr Leu Glu Ala Leu Asp Tyr Lys Glu Cys
210                 215                 220

Glu Trp Pro Leu Thr His Thr Ile Gly Thr Ser Val Glu Glu Ser Glu
225                 230                 235                 240

Met Phe Met Pro Arg Ser Ile Gly Gly Pro Val Ser Ser His Asn His
                245                 250                 255

Ile Pro Gly Tyr Lys Val Gln Thr Asn Gly Pro Trp Met Gln Val Pro
            260                 265                 270

Leu Glu Val Lys Arg Glu Ala Cys Pro Gly Thr Ser Val Ile Ile Asp
        275                 280                 285

Gly Asn Cys Asp Gly Arg Gly Lys Ser Thr Arg Ser Thr Thr Asp Ser
290                 295                 300

Gly Lys Val Ile Pro Glu Trp Cys Cys Arg Ser Cys Thr Met Pro Pro
305                 310                 315                 320

Val Ser Phe His Gly Ser Asp Gly Cys Trp Tyr Pro Met Glu Ile Arg
                325                 330                 335
```

Pro Arg Lys Thr His Glu Ser His Leu Val Arg Ser Trp Val Thr Ala
            340                 345                 350

<210> SEQ ID NO 6
<211> LENGTH: 352
<212> TYPE: PRT
<213> ORGANISM: Zika virus

<400> SEQUENCE: 6

Asp Val Gly Cys Ser Val Asp Phe Ser Lys Lys Glu Thr Arg Cys Gly
1               5                   10                  15

Thr Gly Val Phe Ile Tyr Asn Asp Val Glu Ala Trp Arg Asp Arg Tyr
            20                  25                  30

Lys Tyr His Pro Asp Ser Pro Arg Arg Leu Ala Ala Ala Val Lys Gln
            35                  40                  45

Ala Trp Glu Glu Gly Ile Cys Gly Ile Ser Ser Val Ser Arg Met Glu
        50                  55                  60

Asn Ile Met Trp Lys Ser Val Glu Gly Glu Leu Asn Ala Ile Leu Glu
65                  70                  75                  80

Glu Asn Gly Val Gln Leu Thr Val Val Gly Ser Val Lys Asn Pro
            85                  90                  95

Met Trp Arg Gly Pro Gln Arg Leu Pro Val Pro Val Asn Glu Leu Pro
            100                 105                 110

His Gly Trp Lys Ala Trp Gly Lys Ser Tyr Phe Val Arg Ala Ala Lys
            115                 120                 125

Thr Asn Asn Ser Phe Val Val Asp Gly Asp Thr Leu Lys Glu Cys Pro
            130                 135                 140

Leu Glu His Arg Ala Trp Asn Ser Phe Leu Val Glu Asp His Gly Phe
145                 150                 155                 160

Gly Val Phe His Thr Ser Val Trp Leu Lys Val Arg Glu Asp Tyr Ser
                165                 170                 175

Leu Glu Cys Asp Pro Ala Val Ile Gly Thr Ala Val Lys Gly Arg Glu
            180                 185                 190

Ala Ala His Ser Asp Leu Gly Tyr Trp Ile Glu Ser Glu Lys Asn Asp
        195                 200                 205

Thr Trp Arg Leu Lys Arg Ala His Leu Ile Glu Met Lys Thr Cys Glu
210                 215                 220

Trp Pro Lys Ser His Thr Leu Trp Thr Asp Gly Val Glu Glu Ser Asp
225                 230                 235                 240

Leu Ile Ile Pro Lys Ser Leu Ala Gly Pro Leu Ser His His Asn Thr
                245                 250                 255

Arg Glu Gly Tyr Arg Thr Gln Val Lys Gly Pro Trp His Ser Glu Glu
            260                 265                 270

Leu Glu Ile Arg Phe Glu Glu Cys Pro Gly Thr Lys Val Tyr Val Glu
            275                 280                 285

Glu Thr Cys Gly Thr Arg Gly Pro Ser Leu Arg Ser Thr Thr Ala Ser
        290                 295                 300

Gly Arg Val Ile Glu Glu Trp Cys Cys Arg Glu Cys Thr Met Pro Pro
305                 310                 315                 320

Leu Ser Phe Arg Ala Lys Asp Gly Cys Trp Tyr Gly Met Glu Ile Arg
                325                 330                 335

Pro Arg Lys Glu Pro Glu Ser Asn Leu Val Arg Ser Met Val Thr Ala
            340                 345                 350

METHODS AND COMPOSITIONS FOR THE DETECTION OF *FLAVIVIRUS* INFECTIONS

CROSS REFERENCE TO RELATED APPLICATIONS

This application claims the benefit of U.S. Provisional Patent Application Ser. No. 62/503,201 filed May 8, 2017 and U.S. Provisional Patent Application Ser. No. 62/608,927 filed Dec. 21, 2017, the disclosures of which are expressly incorporated herein by reference.

STATEMENT REGARDING FEDERALLY SPONSORED RESEARCH OR DEVELOPMENT

This invention was made with government support under AI121207 awarded by the National Institutes of Health. The government has certain rights in this invention.

BACKGROUND

*Flavivirus* is a genus of viruses in the family Flaviviridae. Dengue virus (DENV-1, DENV-2, DENV-3, DENV-4), west nile virus (WNV), Japanese encephalitis virus (JEV), yellow fever virus (YFV), zika virus (ZIKV) are the members of this genus with major public health concern worldwide. These viruses combined are responsible for millions of infections and tens of thousands of deaths annually. Clinical manifestations, following *Flavivirus* infections, range from unapparent to a mild febrile disease. However, in some cases a more severe manifestation, characterized by hemorrhagic fever (caused DENV and YFV) and encephalitis (caused by JEV and WNV) occur. More recently, congenital disease (microcephaly) has been associated with ZIKV infection.

Dengue is a global health concern affecting more than 100 countries worldwide. Dengue is caused by Dengue virus, a member of the genus *Flavivirus*, family Flaviviridae, with four antigenically distinct serotypes (DENV-1 to DENV-4). Dengue virus is transmitted by mosquitoes in tropical and subtropical areas of the globe causing illnesses that range from asymptomatic to severe (Rothman, et al., *Nat Rev Immunol.*, 2011, 11:532-43; Simmons, et al., *N Engl J Med.*, 2012, 366:1423-32). More than half of the human population is at risk of infection, making dengue a major public health problem worldwide (Brady, et al., *PLoS Negl Trop Dis.*, 2012, 6:e1760). Infection with any of the serotypes can cause a wide spectrum of clinical manifestations, ranging from asymptomatic or mild febrile symptoms [dengue fever (DF)] and, in rare occasions, life-threatening dengue hemorrhagic fever (DHF) (Peeling, et al., *Nat Rev Microbiol.*, 2010, 8:S30-8). Annually, 100 million symptomatic cases with 0.5-1 million hospitalizations and 25,000 deaths occur worldwide (Simmons, et al., *N Engl J Med.*, 2012, 366: 1423-32). There is currently no licensed treatment against dengue syndromes (DF/DHF).

DENV is a small, enveloped, positive single-stranded RNA that encodes three structural (envelope, membrane and capsid) and seven non-structural (NS) proteins (NS1, NS2a, NS2b, NS3, NS4a, NS4b and NS5) (Guzman, et al., *Nat Rev Microbiol.*, 2010, 8:S7-16). NS1 is particularly important for virus replication as well as disease pathogenesis and diagnosis (Watterson, et al., *Antiviral Res.*, 2016, 130:7-18); it is present on the virus replication complex and cell surface. NS1 is also secreted as a hexamer reaching the peripheral blood circulation, where it increases the permeability of endothelial cells, a hallmark of DHF, via toll-like receptor 4 (Beatty, et al., *Sci Transl Med.*, 2015, 7:304ra141; Modhiran, et al., *Sci Transl Med.*, 2015, 7:304ra142). Circulating NS1 induces antibody responses that have been shown to protect against the development of vasculopathies triggered by this viral protein (Beatty et al., 2015). However, anti-NS1 responses, including antibody isotypes involved and their kinetics, have not been fully characterized.

Efforts to mitigate the burden of the dengue disease have led to the evaluation of many vaccine candidates in clinical trials, and the eventual licensing of the recombinant, live, attenuated, tetravalent dengue vaccine (CYD-TDV; Sanofi Pasteur) in 19 countries to date (Scherwitzl, et al., *Curr Opin Virol.*, 2017, 23:95-101). CYD-TDV is a Chimeric Yellow Fever and Dengue viral construct expressing the envelope (Env) and pre-membrane (prM) proteins of each of the DENV serotypes, and the yellow fever virus (strain 17D) non-structural (NS) proteins, including NS1 (Guy, et al., *Vaccine*, 2011, 29:7229-41). CYD-TDV (also called tetravalent CYD; tetravalent dengue vaccine; Chimerivax®; Dengvaxia®), is disclosed in US Patent Application Publication Nos.: US20150196631, US20150265695, and US20170304426, each of which are incorporated by reference in their entireties. The vaccine has been shown to induce broad neutralizing antibodies and prevent onset of disease (Hernandez-Avila, et al., *Salud Publica Mex.*, 2016, 58:71-83; Malisheni, et al., *Front Immunol.*, 2017, 8:863; Moodie, et al., *J Infect Dis.*, 2017).

Direct isolation of infectious *Flavivirus* (or detection of its RNA) in serum samples is used to determine the etiologic agent. However, high costs and the short time window by which the virus can be detected are significant limitations to this approach. The most widespread method for confirmation of *Flavivirus* infection is by serology for detection of virus-specific IgM and total IgG. These assays are widely used for acute infection diagnosis, although they are highly cross-reactive among all flaviviruses, limiting their use in areas where multiple *Flavivirus* circulate. Moreover, once they are produced, these antibodies circulate in the blood for months (IgM) or even many years (total IgG) post infection, reducing or eliminating their utility to determine disease recency in endemic area.

For example, IgM is the first antibody to be produced during primary dengue infection in response to dengue infection during the first week after onset of the symptoms. Total IgG, on the other hand, can be detected at least two weeks post-symptoms in primary cases. In contrast, in secondary DENV infections, IgM can either be detected at very low titers or remain completely undetected. Total IgG, though, is detectable very early and unless the virus or IgM is detected, confirmation of dengue cases can be challenging in endemic areas where most people are immune to this *Flavivirus*.

Human IgG can be classified into 4 subclasses: IgG1, IgG2, IgG3 and IgG4. These subclasses differ mainly on their ability to bind to Fc-gamma receptors and activate complement system. Additionally, the half-life of most of these subclasses (IgG1, IgG2 and IgG4) is around 21 days, whereas for IgG3 is only 7 days. The reduced half-life of IgG3 is associated with reduced affinity of this antibody to the Fc-gamma receptor involved on the antibody recycling (FcRn) present on endosome compartments of several cells (e.g. endothelial cells and monocytes). Consequently, IgG3 is mostly degraded, rather than recycled, after IgG molecules undergo pinocytosis by monocytes and endothelial cells. See Stapleton, et. al., *Nat. Commun.*, Dec. 20, 2011; 2:599; Vidarsson, et. al., *Front. Immunol.*, Oct. 20, 2014; 5:520.

New assays and markers are needed which can detect *Flavivirus* infection, distinguish recent infection by a *Flavivirus* from a prior infection, and distinguish natural infections with a *Flavivirus* to an immunization with vaccine formulations that do not include NS1 protein. However, several Dengue virus vaccines contain yellow virus NSI protein. Thus, new assays and markers capable of detecting Dengue virus infection, and can distinguish infection by a Dengue virus from an immunization with vaccine formulations that do not include a Dengue virus NS1 protein, or distinguish from infection by another *Flavivirus* such as Zika virus.

SUMMARY

Disclosed are methods and compositions related to detection of recent *Flavivirus* infection. Also disclosed are methods and compositions related to detection of Dengue virus infection.

In one aspect, disclosed herein are methods of detecting recent infection in a subject by one or more flaviviruses comprising a) obtaining a biological sample from the subject; b) contacting the biological sample with one or more *Flavivirus* NS1 proteins; and c) measuring the amount of anti-NS1 IgG3; wherein the presence of anti-NS1 IgG3 indicates recent infection by the one or more flaviviruses.

In one aspect, disclosed herein are methods of any preceding aspect, wherein the one or more NS1 proteins are selected from the group consisting of Dengue 1 NS1, Dengue 2 NS1, Dengue 3 NS1, Dengue 4 NS1, Japanese Encephalitis virus NS1, St. Louis Encephalitis virus NS1, West Nile virus NS1, Zika virus NS1, and Yellow fever virus NS1.

Also disclosed are methods of any preceding aspect, wherein the immunoassay used to detect anti-NS1 IgG3 is selected from the group consisting of enzyme linked immunosorbent assays (ELISAs), enzyme linked immunospot assays (ELIspot), radioimmunoassays (RIA), immunobead capture assays, Western blotting, dot blotting, gel-shift assays, intracellular cytokine stain, immunohistochemistry, protein arrays, and multiplexed bead arrays.

Also disclosed are methods of any preceding aspect, wherein the biological sample from the subject is whole blood, serum, Peripheral blood mononuclear cells (PBMC), saliva, urine, oral secretions, amniotic fluid, plasma, bone marrow, or cerebrospinal fluid (CSF).

In one aspect, disclosed herein are methods of any preceding aspect, further comprising measuring the amount of anti-NS1 total IgG and/or one or more IgG isotypes.

Also disclosed herein are methods of measuring the efficacy of a flaviviral vaccine comprising a) obtaining a biological sample from a subject immunized against a *Flavivirus* with a *Flavivirus* vaccine; b) contacting the biological sample with one or more *Flavivirus* NS1 proteins; and c) measuring the amount of anti-NS1 IgG3 and/or total IgG; wherein the larger magnitude of the anti-NS1 IgG3 and/or total IgG response indicates relative to a control indicates the efficacy of the *Flavivirus* vaccine. In some aspect, the method can further comprise the measurement of the remaining IgG isotypes IgG1, IgG2, IgG3 and/or IgG4, and/or total IgG.

In one aspect, disclosed herein are kits for detecting recent *Flavivirus* infection, vaccine efficacy, or the emergence of vaccine resistant strains of *Flavivirus* comprising one or more *Flavivirus* NS1 proteins; an anti-IgG3 antibody; an anti-IgG1 antibody, an anti-IgG2 antibody; an anti-IgG4 antibody; a total anti-IgG antibody, and/or an anti-IgM antibody.

Also disclosed are methods of detecting a prior Dengue virus infection in a subject comprising a) obtaining a biological sample from the subject previously immunized with a Dengue virus vaccine comprising one or more non-Dengue *Flavivirus* proteins; b) contacting the biological sample with one or more Dengue virus NS1 proteins in an assay wherein there is a low cross-reactivity with the one or more non-Dengue *Flavivirus* proteins; and c) measuring an amount of anti-Dengue virus NS1 total IgG; wherein an increase in the anti-Dengue virus NS1 total IgG relative to a control indicates the prior Dengue virus infection in the subject.

Also disclosed are methods of detecting a prior Dengue virus infection in a subject comprising a) obtaining a biological sample from the subject previously immunized with a Dengue virus vaccine comprising one or more non-Dengue *Flavivirus* proteins; b) contacting the biological sample with one or more Dengue virus NS1 proteins in an assay wherein there is a low cross-reactivity with the one or more non-Dengue *Flavivirus* proteins; and c) measuring an amount of one or more of anti-Dengue virus NS1 IgG1, IgG2, IgG3, and IgG4; wherein an increase in one or more of the amounts relative to a control indicates the prior Dengue virus infection in the subject.

Also disclosed are methods of detecting a prior Dengue virus infection in a subject comprising a) contacting a biological sample from the subject with one or more Dengue virus NS1 proteins in an assay wherein there is a low cross-reactivity with one or more non-Dengue *Flavivirus* proteins; and b) measuring an amount of one or more of anti-Dengue virus NS1 IgG1, IgG2, IgG3, IgG4 and total IgG; wherein an increase in one or more of the amounts relative to a control indicates the prior Dengue virus infection in the subject.

BRIEF DESCRIPTION OF THE DRAWINGS

The accompanying drawings, which are incorporated in and constitute a part of this specification, illustrate several embodiments and together with the description illustrate the disclosed compositions and methods.

FIG. 3(A-B) are graphs showing detection of anti-dengue NS1-specific total IgG or IgG3 at different time points after onset of symptoms.

FIG. 4(A-B) shows detection of other *Flavivirus* NS1-specific IgG in confirmed West Nile Virus (WNV) infection or yellow fever (YF) vaccine recipients.

FIG. 7 is a table showing general participant demographics.

FIG. 8 is a table showing a comparison on anti-dengue NS1-specific total IgG and IgG3 detection between primary and secondary dengue infections.

FIG. 9 is a table showing a comparison of anti-dengue NS1-specific total IgG and IgG3 detection between mild (DF) and severe (DFC+DHF) dengue clinical manifestations FIG. 10 is a table showing performance and limit ranges of the IVIG reference curve.

FIG. 11 is a table showing performance characteristics for positive and negative control samples.

FIG. 12 is a table showing evaluation of accuracy of the anti-dengue NS1 IgG ELISA.

FIG. 13 is a table showing verification of lower limit of quantitation (LLOQ) of the anti-dengue NS1 IgG ELISA.

FIG. 14 is a table showing evaluation of specificity of anti-dengue NS1 IgG ELISA with samples positive to other related flaviviruses.

FIG. 15 is a table showing M13 anti-dengue NS1 IgG ELISA serostatus classification of baseline (M0) antidengue NS1 IgG seronegative or seropositive participants who did not have symptomatic VCD infection between first and last injection.

DETAILED DESCRIPTION

Figure 1A:
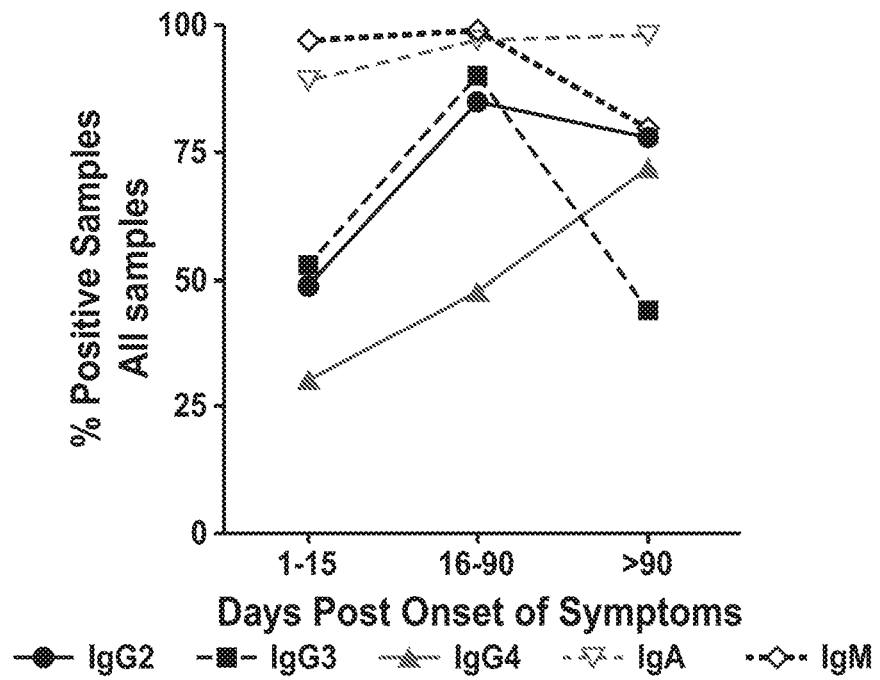
FIG. 1(A-C) shows percentage of samples testing positive for different antibody isotypes specific to dengue virus NS1 protein at different stages following infection considering all patients (FIG. 1A), primary (FIG. 1B), or secondary (FIG. 1C) infections. Samples analyzed were collected at 1-15 days [all samples (n=296), primary infection (n=129) and secondary infection (n=167)], 16-90 days [all samples (n=133), primary infection (n=44) and secondary infection (n=89)] and >90 days [all samples (n=50), primary infection (n=21) and secondary infection (n=29)] post infection.

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

DEFINITIONS

Unless defined otherwise, all technical and scientific terms used herein have the same meaning as commonly understood to one of ordinary skill in the art to which this invention belongs. The following definitions are provided for the full understanding of terms used in this specification.

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

The terms "about" and "approximately" are defined as being "close to" as understood by one of ordinary skill in the art. In some non-limiting embodiments, the terms are defined to be within 10% of the associated value provided. In some non-limiting embodiments, the terms are defined to be within 5%. In still other non-limiting embodiments, the terms are defined to be within 1%.

Grammatical variations of "administer," "administration," and "administering" to a subject include any route of introducing or delivering to a subject an agent. A subject immunized with a vaccine has been administered a vaccine. Administration can be carried out by any suitable route, including oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation, via an implanted reservoir, parenteral (e.g., subcutaneous, intravenous, intramuscular, intra-articular, intra-synovial, intrasternal, intrathecal, intraperitoneal, intrahepatic, intralesional, and intracranial injections or infusion techniques), and the like. "Concurrent administration", "administration in combination", "simultaneous administration" or "administered simultaneously" as used herein, means that the compounds are administered at the same point in time, overlapping in time, or one following the other. In the latter case, the two compounds are administered at times sufficiently close that the results observed are indistinguishable from those achieved when the compounds are administered at the same point in time. "Systemic administration" refers to the introducing or delivering to a subject an agent via a route which introduces or delivers the agent to extensive areas of the subject's body (e.g. greater than 50% of the body), for example through entrance into the circulatory or lymph systems. By contrast, "local administration" refers to the introducing or delivery to a subject an agent via a route which introduces or delivers the agent to the area or area immediately adjacent to the point of administration and does not introduce the agent systemically in a therapeutically significant amount. For example, locally administered agents are easily detectable in the local vicinity of the point of administration but are undetectable or detectable at negligible amounts in distal parts of the subject's body. Administration includes self-administration and the administration by another.

The term "antibody" is used in the broadest sense and encompass native antibodies, for example antibodies produced by a subject and may be detectable in a biological sample of the subject. Antibodies exhibit binding specificity to a specific target, and are usually heterotetrameric glycoproteins of about 150,000 daltons, composed of two identical light (L) chains and two identical heavy (H) chains.

Each heavy chain has at one end a variable domain (VH) followed by a number of constant domains. Each light chain has a variable domain at one end (VL) and a constant domain at its other end.

The term "anti-NS1 antibody" or variations thereof (e.g., anti-DENV NS1 antibody; anti-NS1 IgG3 antibody) refer to an antibody which specifically binds to a NS1 protein.

A "control" is an alternative subject, sample, or set of values used in an experiment for comparison purposes. A control can be "positive" or "negative." A control comprising a collection of values can be used as a standard applied to one or more subjects (e.g., a general number or average that is known and not identified in the method using a sample). For example, a control can comprise a known or determined amount (e.g., an average amount) of antibody (e.g., IgG3) specific for a polypeptide of interest (e.g., NS1) present in a given population. In such a non-limiting example, an average value from a population known to be unexposed to a particular *Flavivirus* relevant to the study can serve as a negative control, whereas an average value from a population known to be exposed to a particular *Flavivirus* relevant to the study can serve as a positive control. Alternatively, and as another non-limiting example, a negative control can comprise a biological sample of a subject known or determined to be unexposed to a particular *Flavivirus* relevant to the study, whereas a positive control can comprise a biological sample of a subject known or determined to be exposed to a particular *Flavivirus* relevant to the study. In embodiments in which a measured amount of an antibody (or a measured amount of a response) is compared to a control, and in which an increase in the amount of the antibody or response indicates an outcome, the control is generally a negative control. In some embodiments, the control can be a biological sample of a subject known or determined to be exposed to a particular *Flavivirus* relevant to the study, wherein the biological sample of the control and the biological sample to be tested are of the same type of biological sample (e.g., blood, sputum, plasma, urine, saliva, etc.).

The term "cross-reactivity" as used herein refers to the detection of an interfering polypeptide in an assay to detect a polypeptide of interest. A first polypeptide is cross-reactive with a second polypeptide in an assay if the assay indiscriminately detects both polypeptides (e.g., an antibody specific for the first polypeptide also binds the second polypeptide). The degree of detection of each of the polypeptides may or may not be equivalent; however, detection of the second polypeptide sufficiently interferes with detection of the first polypeptide. Cross-reactivity is common for polypeptides having highly identical orthologues (e.g., a Dengue Virus NS1 polypeptide and a Yellow Fever Virus NS1 polypeptide). Thus, an assay having a low cross-reactivity with one or more polypeptides can refer to an assay which reliably detects a first polypeptide without significant interfering detection of a second polypeptide. The amount of interfering detection can, in some embodiments, be quantified by an interference ratio between a signal observed for a first polypeptide to a signal observed for a second polypeptide in an assay which includes about the same amount of first and second polypeptides. If the calculated interference ratio is above a threshold interference ratio, the assay can be said to have low cross-reactivity between the two polypeptides examined. In some embodiments, the interference ratio of a first polypeptide signal to a second polypeptide signal in a low cross-reactivity assay is 5:1 or greater, 7:1 or greater, 10:1 or greater, 15:1 or greater, 20:1 or greater, 50:1 or greater, 100:1 or greater, 500:1 or greater, 1,000:1 or greater, or 10,000:1 or greater.

As used herein "infection" refers to a humoral immune response to a *Flavivirus* in a subject as detectable by the methods of the present invention, whether the subject is symptomatic or asymptomatic.

"Identical" or percent "identity," in the context of two or more polynucleotide or polypeptide sequences, refer to two or more sequences or subsequences that are the same or have a specified percentage of amino acid residues or nucleotides that are the same (e.g., about 60% identity, preferably 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over a specified region when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the complement of a test sequence. The definition also includes sequences that have deletions and/or additions, as well as those that have substitutions. As described below, the preferred algorithms can account for gaps and the like. Preferably, identity exists over a region that is at least about 10 amino acids or 20 nucleotides in length, or more preferably over a region that is 10-50 amino acids or 20-50 nucleotides in length. As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

One example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. (1990) *J. Mol. Biol.* 215:403-410). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01.

"NS1," as used herein, refers to one or more "non-structural protein 1" polypeptides of a *Flavivirus*. The term NS1 includes non-structural protein 1 polypeptide monomers, dimers, trimers, tetramers, and hexamers. In some embodiments, the NS1 is a hexamer. In other or further embodiments, the NS1 is recombinant. Depending on context, NS1 can refer to any one or more of Dengue 1 NS1, Dengue 2 NS1, Dengue 3 NS1, Dengue 4 NS1, Japanese Encephalitis virus NS1, St. Louis Encephalitis virus NS1, West Nile virus NS1, Zika virus NS1, and Yellow fever virus NS1.

In some embodiments, NS1 is a polypeptide derived from a Dengue Virus 1 (a Dengue 1 NS1). In some embodiments, the Dengue Virus 1 is of the strain Nauru/Western Pacific/1974. In some embodiments, NS1 is a polypeptide comprising an amino acid sequence which is at least 80% identical to SEQ ID NO: 1. In some embodiments, NS1 is a polypeptide comprising an amino acid sequence which is at least 85%, at least 90%, at least 95%, at least 98%, or at least 99% identical to SEQ ID NO: 1. In some embodiments, NS1 is a polypeptide comprising SEQ ID NO: 1.

In some embodiments, NS1 is a polypeptide derived from a Dengue Virus 2 (a Dengue 2 NS1). In some embodiments, the Dengue Virus 2 is of the strain Thailand/16681/84. In some embodiments, NS1 is a polypeptide comprising an amino acid sequence which is at least 80% identical to SEQ ID NO: 2. In some embodiments, NS1 is a polypeptide comprising an amino acid sequence which is at least 85%, at least 90%, at least 95%, at least 98%, or at least 99% identical to SEQ ID NO: 2. In some embodiments, NS1 is a polypeptide comprising SEQ ID NO: 2.

In some embodiments, NS1 is a polypeptide derived from a Dengue Virus 3 (a Dengue 3 NS1). In some embodiments, the Dengue Virus 3 is of the strain Sri Lanka D3/H/IMTSSA-SRI/2000/1266. In some embodiments, NS1 is a polypeptide comprising an amino acid sequence which is at least 80% identical to SEQ ID NO: 3. In some embodiments, NS1 is a polypeptide comprising an amino acid sequence which is at least 85%, at least 90%, at least 95%, at least 98%, or at least 99% identical to SEQ ID NO: 3. In some embodiments, NS1 is a polypeptide comprising SEQ ID NO: 3.

In some embodiments, NS1 is a polypeptide derived from a Dengue Virus 4 (a Dengue 4 NS1). In some embodiments, the Dengue Virus 4 is of the strain Dominica/814669/1981. In some embodiments, NS1 is a polypeptide comprising an amino acid sequence which is at least 80% identical to SEQ ID NO: 4. In some embodiments, NS1 is a polypeptide comprising an amino acid sequence which is at least 85%, at least 90%, at least 95%, at least 98%, or at least 99% identical to SEQ ID NO: 4. In some embodiments, NS1 is a polypeptide comprising SEQ ID NO: 4.

In some embodiments, NS1 is a polypeptide derived from a Yellow Fever Virus (a Yellow Fever Virus NS1; YFV NS1). In some embodiments, the Yellow Fever Virus is of the strain 17D or 17DD. In some embodiments, NS1 is a polypeptide comprising an amino acid sequence which is at least 80% identical to SEQ ID NO: 5. In some embodiments, NS1 is a polypeptide comprising an amino acid sequence which is at least 85%, at least 90%, at least 95%, at least 98%, or at least 99% identical to SEQ ID NO: 5. In some embodiments, NS1 is a polypeptide comprising SEQ ID NO: 5.

In some embodiments, NS1 is a polypeptide derived from a Zika Virus (a Zika Virus NS1; ZIKV NS1). In some embodiments, the Zika Virus is of the strain Suriname Z1106033 or from the strain Uganda MR 766. In some embodiments, NS1 is a polypeptide comprising an amino acid sequence which is at least 80% identical to SEQ ID NO: 6. In some embodiments, NS1 is a polypeptide comprising an amino acid sequence which is at least 85%, at least 90%, at least 95%, at least 98%, or at least 99% identical to SEQ ID NO: 6. In some embodiments, NS1 is a polypeptide comprising SEQ ID NO: 6.

In some embodiments, NS1 is a polypeptide derived from a West Nile Virus (a West Nile Virus NS1; WNV NS1). In some embodiments, the West Nile Virus is of the strain NY99. In some embodiments, NS1 is a polypeptide derived from a Japanese Encephalitis Virus (a Japanese Encephalitis virus NS1; JEV NS1). In some embodiments, NS1 is a polypeptide derived from a St. Louis Encephalitis Virus (a St. Louis Encephalitis virus NS1).

"Peptide," "protein," and "polypeptide" are used interchangeably to refer to a natural or synthetic molecule comprising two or more amino acids linked by the carboxyl group of one amino acid to the alpha amino group of another. Non-limiting examples of polypeptides include peptide fragments, denatured/unstructured polypeptides, polypeptides having quaternary or aggregated structures, etc. There is expressly no requirement that a polypeptide must contain an intended function; a polypeptide can be functional, non-functional, function for unexpected/unintended purposes, or have unknown function. A polypeptide is comprised of approximately twenty, standard naturally occurring amino acids, although natural and synthetic amino acids which are not members of the standard twenty amino acids may also be used. The standard twenty amino acids include alanine (Ala, A), arginine (Arg, R), asparagine (Asn, N), aspartic acid (Asp, D), cysteine (Cys, C), glutamine (Gln, Q), glutamic acid (Glu, E), glycine (Gly, G), histidine, (His, H), isoleucine (Ile, I), leucine (Leu, L), lysine (Lys, K), methionine (Met, M), phenylalanine (Phe, F), proline (Pro, P), serine (Ser, S), threonine (Thr, T), tryptophan (Trp, W), tyrosine (Tyr, Y), and valine (Val, V). The terms "polypeptide sequence" and "amino acid sequence" are an alphabetical representation of a polypeptide molecule.

A polypeptide can contain chemical modifications such as disulfide bridges, substitution of radioisotopes, phosphorylation, substrate chelation (e.g., chelation of iron or copper atoms), glycosylation, acetylation, formylation, amidation, biotinylation, and a wide range of other modifications. A polypeptide may be attached to other molecules, for instance molecules required for function. Examples of molecules which may be attached to a polypeptide include, without limitation, cofactors, polynucleotides, lipids, metal ions, phosphate, etc. A polypeptide produced recombinantly may additionally comprise "tags" for purification and/or identification purposes. Numerous polypeptide tags are known in the art, including as non-limiting examples hexahistidine tag, sumo tag, AviTag™, FLAG-tag, hemagglutinin tag, streptavidin tag, polyglutamate tag, myc tag, and numerous others (e.g., NS1-his tagged recombinant protein).

A "recent *Flavivirus* infection" is defined herein as an infection within 6 months or less prior to the date of obtaining a biological sample from the infected subject. In some embodiments, the infection occurs within 5 months or less, 4 months or less, 3 months or less, 2 months or less, or 1 month or less prior to the date of obtaining a biological sample from the subject.

"Specifically binds" when referring to a polypeptide (including antibodies) or receptor, refers to a binding reaction which is determinative of the presence of the protein or polypeptide or receptor in a heterogeneous population of proteins and other biologics. Thus, under designated conditions (e g immunoassay conditions in the case of an antibody), a specified ligand or antibody "specifically binds" to its particular "target" (e.g. an antibody specifically binds to an endothelial antigen) when it does not bind in a significant amount to other proteins present in the sample or to other proteins to which the ligand or antibody may come in contact in an organism. Generally, a first molecule that "specifically binds" a second molecule has an affinity constant (Ka) greater than about $10^5$ M$^{-1}$ (e.g., $10^6$ M$^{-1}$, $10^7$ M$^{-1}$, $10^8$ M$^{-1}$, $10^9$ M$^{-1}$, $10^{10}$ M$^{-1}$, $10^{11}$ M$^{-1}$, and $10^{12}$ M$^{-1}$ or more) with that second molecule.

The term "subject" includes animals such as mammals, including, but not limited to, primates (e.g., humans), cows, sheep, goats, horses, dogs, cats, rabbits, rats, mice and the like. In some embodiments, the subject is an animal capable of being infected, at risk of being infected, suspected of being infected, or known to be infected with a *Flavivirus*. In some embodiments, the subject is a mammal. In some embodiments, the subject is a human. In some embodiments, the subject is a human having been present in a location suspected to be or known to be endemic for a *Flavivirus*.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

"Optional" or "optionally" means that the subsequently described event or circumstance may or may not occur, and that the description includes instances where said event or circumstance occurs and instances where it does not.

DETAILED DESCRIPTION OF EMBODIMENTS

Anti-dengue NS1 IgG and IgG3 are identified herein as biomarkers of long-term and recent DENV infection, respectively. Accordingly, provided herein are compositions and methods for detecting recent and long-term DENV infections, and defining disease prevalence and incidence in at-risk populations. Also provided herein are methods that can discriminate previous dengue infection from vaccination with a recombinant, live, attenuated, tetravalent dengue vaccine (referred to herein as "CYD-TDV").

Compositions and Methods for Detection of Recent *Flavivirus* Infection

Although anti-dengue NS1-specific IgA, IgM and IgG have been detected during the convalescent phase in individuals suffering from mild disease (Shu, et al., *J Med Virol.*, 2000, 62:224-32), the duration and isotype profile have not been fully assessed. To this end, the anti-dengue NS1-specific IgA, IgM, IgG2, IgG3 and IgG4 profiles were characterized herein in samples collected during the febrile acute phase of illness and over 1 year after onset of symptoms following DENV3 infection. Although both IgA and IgM antibodies (primarily targeting the viral envelope protein) are often used as biomarkers of acute infection, results shown here suggest that they are of limited value in diagnosing acute or even determining recent infections.

As shown herein, anti-dengue NS1 IgG and IgG3 were consistently detected within the first week and peaked at 2-3 weeks. However, while anti-dengue NS1 IgG was detected at high levels up to 3 years after the onset of symptoms, anti-dengue NS1 IgG3 could not be detected in most participants after 4-6 months. Unlike anti-dengue NS1 IgG (comprised mostly by IgG1 subclass), IgG3 has the shortest half-life (7 days) due to its relative lower affinity to the neonate Fc receptor (FcRn), responsible for antibody recycling (Roopenian, et al., *Nat Rev Immunol.*, 2007, 7:715-25). As a result, increased degradation of anti-dengue NS1 IgG3 occurs relatively shortly after expression, limiting its inflammatory properties and detection in the peripheral blood (Roopenian, 2007). Similar patterns have been observed in incident HIV infection (Seaton, et al., *JCI Insight.*, 2017, 2:pii: 94355; Yates, et al., AIDS, 2011, 25:2089-97). Thus, antigen-specific IgG3 is a good biomarker for recent viral infection.

Dengue virus infection results mostly in asymptomatic symptoms (Grange, et al., *Front Immunol.*, 2014, 5:280) and as such can be difficult, without laboratory confirmation, making accurate estimates of the disease incidence. Direct confirmation of infection using tools such as PCR and detection of NS1 antigen have limited time windows (within the first few days after the onset of symptoms) for maximum sensitivity (Ahmed, et al., *J Vector Borne Dis.*, 2014, 51:194-9). In contrast, as described herein, anti-dengue NS1-specific IgG3 is detected very early after the onset of symptoms and has a wider detection window (4-6 months). In addition, the assay described herein can be translated to a high-throughput setting and is likely to have relatively lower associated costs. Thus, the detection of anti-dengue NS1-specific IgG3 is more useful for diagnosing recent infections and for generating incidence estimates, using MDIG3 and FRPS, in a sampled population.

Accordingly, disclosed herein are methods for detecting a recent infection of a subject to one or more flaviviruses. Typically, IgG antibody levels, once established for a given antigenic exposure, remain elevated though possibly slightly diminished relative to peak antibody levels. This is due to the establishment of memory B cells and long-lived plasma cells which are constantly secreting antibody. Thus, antibody levels from a secondary infection start at an elevated level and have an increased steady state level once the infection is established. It is shown herein that IgG3 has a short half-life, which results in a precipitous drop-off in IgG3 within 4 months of the onset of symptoms of a *Flavivirus* infection. Consequently, IgG3 antibody levels specific to a *Flavivirus* infection produced by long-lived plasma cells is comparatively low to non-existent and secondary infections do not result in an increased steady state level of antibody production. Accordingly, IgG3 represents an ideal antibody isotype to detect the emergence of a recent infection.

Disclosed herein are methods for detecting a recent infection of a subject by one or more flaviviruses. In some embodiments, the methods comprise a) obtaining a biological sample from the subject; b) contacting the biological sample with one or more *Flavivirus* NS1 proteins; and c) measuring the amount of anti-NS1 IgG3; wherein the presence of anti-NS1 IgG3 indicates recent infection by one or more flaviviruses. In some embodiments, the detection of anti-NS1 antibodies of different IgG isotypes, IgM, and/or total IgG can provide useful information regarding the historical infection in the subject. Thus, in some embodiments, the disclosed methods can further comprise measuring the amount of anti-NS1 total IgG, IgM, and/or one or more IgG isotypes.

It is understood and herein contemplated that the ability to discriminate a recent *Flavivirus* infection from a prior *Flavivirus* infection has applications beyond the mere determination of a recent infection, for example measuring the efficacy of a vaccine, where the level of anti-NS1 IgG3 antibody generated indicates the efficacy of the vaccine. Due to the cross-reactivity of some *Flavivirus* antigens, total IgG, IgM, or major isotypes IgG1, IgG2, and IgG4, which remain at elevated levels for the life of the host, can give false positive determinations of efficacy if taken alone. Because IgG3 is short-lived and is quick to increase following antigenic exposure, IgG3 provides a better marker for an immune response to recent *Flavivirus* exposure and consequently to a recently administered vaccine.

Also disclosed herein are methods of measuring the efficacy of a flaviviral vaccine comprising a) obtaining a biological sample from a subject immunized against a *Flavivirus* with a *Flavivirus* vaccine; b) contacting the biological sample with one or more *Flavivirus* NS1 proteins; and c) measuring the amount of anti-NS1 IgG3; wherein an increase in the anti-NS1 IgG3 relative to a control indicates the efficacy of the *Flavivirus* vaccine. In some embodiments, the methods can further comprise measuring one or more of the remaining IgG isotypes IgG1, IgG2, and IgG4, and total IgG.

In some embodiments, the measurement of total IgG anti-NS1 can be used to identify an infection occurring after immunization. For example, Sanofi Dengue Vaccine does not express dengue NS1 and anti-dengue NS1 antibodies do not significantly cross react with yellow fever NS1. Also, the detecting of increased titer of anti-dengue-NS1 indicates infection. By titrating the anti-NS1 antibodies in at least two time points, one can quantify the efficacy of the vaccine against symptomatic and asymptomatic dengue infections.

Accordingly, also disclosed herein are methods of measuring the efficacy of a flaviviral vaccine comprising a) obtaining a biological sample from a subject immunized against a *Flavivirus* with a *Flavivirus* vaccine at two or more time points; b) contacting the biological samples with one or more *Flavivirus* NS1 proteins; c) titrating the anti-NS1 antibodies for the two or more time points; and d) measuring the amount of anti-NS1 total IgG; wherein an increase in the anti-NS1 total IgG relative to a control indicates the efficacy of the *Flavivirus* vaccine. In some embodiments, the methods can further comprise the measurement of the remaining IgG isotypes IgG1, IgG2, IgG3, and/or IgG4.

In some embodiments, the two or more time points comprise a first time point and a second time point. In some embodiments, the first and second time points are at least 1 day, at least 2 days, at least 3 days, at least 5 days, at least 7 days, at least 10 days, at least 2 weeks, at least 4 weeks, at least 1 month, at least 2 months, at least 3 months, at least 6 months, or at least 1 year apart.

Due to the ability to detect a recent *Flavivirus* infection, the disclosed methods can also be used to detect the emergence of a *Flavivirus* that is resistant to the vaccine.

In some embodiments, the disclosed methods can also be used to identify infection by a *Flavivirus*, such as, Zika virus during gestation and evaluate the risk of congenital syndrome, such as Zika syndrome; wherein the presence of a recent *Flavivirus* infection, such as a Zika virus infection, during gestation indicates an increased risk of congenital syndrome.

Accordingly, also disclosed herein are methods of detecting infection by a *Flavivirus*, such as, Zika virus during gestation in a subject and thereby an increased risk of congenital syndrome, such as Zika syndrome to the offspring of the subject comprising a) obtaining a biological sample from a subject; b) contacting the biological sample with one or more *Flavivirus* NS1 proteins, such as, Zika NS1 protein; and c) measuring the amount of anti-NS1 IgG3; wherein an increase in the anti-NS1 IgG3 relative to a control indicates the presence of Zika virus in the subject during gestation and an increased risk of congenital syndrome. In some embodiments, the method can further comprise measuring one or more of the remaining IgG isotypes IgG1, IgG2, and IgG4, and total IgG.

Compositions and Methods for Detection of Dengue Virus Infection in Subjects Immunized Against *Flavivirus*

Results described herein demonstrate that the anti-dengue NS1 IgG ELISA is qualified and provides valuable information for the assessment of dengue serostatus of CYD-TDV recipients in samples collected after vaccination. This has enabled a post hoc analysis to further evaluate vaccine safety and efficacy by dengue serostatus, in particular, to more precisely ascertain risk estimates in dengue seronegative individuals.

As described herein, an anti-dengue NS1 IgG specific ELISA was investigated to evaluate the serostatus of individuals both before and after vaccination with CYD-TDV. The developed anti-dengue NS1 IgG ELISA, using the 9 EU/mL threshold, is a suitable alternative to dengue PRNT for assessing baseline dengue serostatus. The ELISA differentiates between anti-dengue NS1 antibodies induced by wild-type dengue infection and CYD-TDV and provides useful information on dengue serostatus in both pre- and/or post-vaccination samples.

Assessment of accuracy, precision and linearity/dilutability all demonstrated suitable performance even in the presence of hemolytic, icteric and lipidic matrices. In addition, little to no interference was observed in competition studies with unrelated antigens or NS1 proteins from multiple flaviviruses.

Although the anti-dengue NS1 IgG ELISA 9 EU/mL threshold (near the LLOQ) minimized the false seronegative rate, it does result in a relatively high false seropositive rate. Nonetheless, as the most relevant question related to CYD-TDV safety and efficacy is in individuals without previous infection by dengue (e.g. dengue seronegative), the 9 EU/mL threshold was chosen for the reanalysis of M13 samples to infer baseline dengue serostatus in the subsequent post hoc analysis of vaccine safety and efficacy in clinical studies (Sridhar et al., manuscript submitted). The 9 EU/mL threshold minimized the incorrect inclusion of dengue exposed participants (dengue seropositive) into the seronegative estimates. This was particularly important as the CYD-TDV efficacy trials were undertaken in endemics settings with high dengue seroprevalence, and as such, the participants had a high likelihood of prior infection by dengue. In contrast, a threshold of 50 EU/mL minimizes the false seropositive rate and can be considered more adequate for correctly identifying those previously exposed to dengue, by limiting the potential misclassification of those not previously exposed to dengue as seropositive. The actual readout of the anti-dengue NS1 IgG ELISA post-vaccination can also be utilized as a continuous variable in combination with other variables for the prediction of baseline dengue serostatus.

The anti-dengue NS1 IgG GMCs is likely influenced by CYD-TDV exposure to some extent. This influence was greater in individuals known to be dengue seropositive at baseline (by dengue PRNT), but was still apparent in individuals known to be seronegative, albeit at very low levels (GMCs remained <9 EU/mL). The relatively low impact of CYD-TDV on anti-dengue NS1 IgG GMCs in those dengue seronegative further supports its utility in subsequent post hoc analysis of vaccine safety and efficacy (Sridhar et al. manuscript submitted). However, some misclassification of baseline seronegatives as seropositives was observed for both vaccine recipients and controls. This may be partially explained by assay variability or asymptomatic dengue infections occurring between M0 (pre-vaccination) and M13 (post-vaccination). Interestingly, the frequency of misclassification observed in the control group is consistent with previously reported rates of asymptomatic dengue infections in these studies (Olivera-Botello et al., *J Infect Dis.*, 2016, 21: 994-1000). Nevertheless, the excess misclassification observed in the vaccine group compared to the control group is likely explained by a moderate effect of CYD-TDV on the post-vaccination anti-dengue NS1 IgG levels.

Accordingly, disclosed herein are compositions and methods for detecting a prior Dengue virus infection in a subject, and in some embodiments, a prior Dengue virus infection that occurred prior to a *Flavivirus* immunization. In some aspects, methods are provided for detecting a prior Dengue virus infection in a subject comprising a) obtaining a biological sample from the subject previously immunized with a Dengue virus vaccine comprising one or more non-Dengue *Flavivirus* proteins; b) contacting the biological sample with one or more Dengue virus NS1 proteins in an assay wherein there is a low cross-reactivity with the one or more non-Dengue *Flavivirus* proteins; and c) measuring an amount of anti-Dengue virus NS1 total IgG; wherein an increase in the anti-Dengue virus NS1 total IgG relative to a control indicates the prior Dengue virus infection in the subject.

In some aspects, methods are provided for detecting a prior Dengue virus infection in a subject comprising a) obtaining a biological sample from the subject previously immunized with a Dengue virus vaccine comprising one or more non-Dengue *Flavivirus* proteins; b) contacting the biological sample with one or more Dengue virus NS1 proteins in an assay wherein there is a low cross-reactivity with the one or more non-Dengue *Flavivirus* proteins; and c) measuring an amount of one or more of anti-Dengue virus NS1 IgG1, IgG2, IgG3, and IgG4; wherein an increase in one or more of the amounts relative to a control indicates the prior Dengue virus infection in the subject.

In other aspects, methods are provided for detecting a prior Dengue virus infection in a subject comprising a) contacting the biological sample with one or more Dengue virus NS1 proteins in an assay wherein there is a low cross-reactivity with one or more non-Dengue flaviviruses; and b) measuring an amount of one or more of anti-Dengue virus NS1 IgG1, IgG2, IgG3, IgG4 and total IgG; wherein there is a low cross-reactivity with one or more non-Dengue flaviviruses, and wherein an increase in one or more of the amounts relative to a control indicates the prior Dengue virus infection in the subject.

In some embodiments, the non-Dengue *Flavivirus* is West Nile virus, Japanese Encephalitis virus, Yellow Fever virus, or Zika virus. In some embodiments, the non-Dengue *Flavivirus* is a Yellow Fever virus. In some embodiments, the non-Dengue *Flavivirus* is a Zika virus.

In some embodiments, the one or more NS1 proteins in the assay is selected from the group consisting of Dengue 1 NS1, Dengue 2 NS1, Dengue 3 NS1, and Dengue 4 NS1. In some embodiments, the Dengue 1 NS1 is of strain Nauru/Western Pacific/1974, the Dengue 2 NS1 is of strain Thailand/16681/84, the Dengue 3 NS1 is of strain Sri Lanka D3/H/IMTSSA-SRI/2000/1266, and/or the Dengue 4 NS1 is of strain Dominica/814669/1981. In some embodiments, the one or more NS1 proteins is a recombinant NS1 protein.

The assay comprising contacting the biological sample with one of more Dengue virus NS1 proteins results in low cross-reactivity with one or more non-Dengue virus proteins due to the identity of the one or more of the NS1 protein(s) and/or the assay conditions. Assay conditions that can result in low-cross reactivity include, but are not limited to, time of contact between binding constituents (i.e., NS1 protein and NS1 protein antibody), temperature, pH, media, and any combination thereof. In some embodiments "low crossreactivity" refers to no, less than 0.25%, less than 0.5%, less than 1%, or less than 5% statistically significant reactivity.

In some embodiments, the prior immunization is with a vaccine that does not comprise a Dengue virus NS1 protein or does not comprise an immunogenic Dengue virus NS1 protein. In other or further embodiments, the prior immunization is with a vaccine that comprises a yellow fever NS1 protein. One non-limiting example of such a vaccine is a Sanofi Dengvaxia vaccine. In some embodiments, the prior Dengue virus infection occurred before immunization. In other embodiments, the prior Dengue virus infection occurred after immunization. In some embodiments, by titrating the anti-NS1 antibodies in at least two time points one can quantify the efficacy of the vaccine against symptomatic and asymptomatic Dengue infections.

In some instances, the detection of anti-NS1 antibodies of different IgG isotypes, IgM, and/or total IgG can provide useful information regarding the historical infection in the subject. Thus, in one aspect, the disclosed methods can further comprise measuring the amount of anti-NS1 total IgG, IgM, and/or one or more IgG isotypes.

The disclosed methods utilize biological samples obtained from a subject to perform an immunoassay. In one aspect, the biological sample from the subject is whole blood, serum, Peripheral blood mononuclear cells (PBMC), saliva, urine, oral secretions, amniotic fluid, plasma, bone marrow, or cerebrospinal fluid (CSF). The biological sample can be obtained via any means known in the art for collecting tissue.

In some embodiments, the biological sample is taken prior to immunization with a Dengue virus vaccine. In some embodiments, the biological sample is taken after immunization with a Dengue virus vaccine. The biological sample can be taken days, weeks or months following immunization. In some embodiments the biological sample can be taken between about one and three weeks, about two and four weeks, about three and five weeks, or about four and six weeks following immunization. In some embodiments, the biological sample can be taken between about one and three months, about two and four months, about three and five months, or about four and six months following immunization. In some embodiments, the biological sample can be taken greater than about one, two, three, four, five, six, seven or eight weeks following immunization. In some embodiments the biological sample can be taken between one and thirty days, between thirty and sixty days, or greater than thirty days following immunization.

Immunoassays

The disclosed methods can use immunoassays that detect the binding of anti-*Flavivirus* NS1 antibodies (e.g., IgG1, IgG2, IgG3, IgG4, total IgG, and/or IgM) to one or more NS1 proteins. In some embodiments, the one or more NS1 proteins are selected from the group consisting of Dengue 1 NS1, Dengue 2 NS1, Dengue 3 NS1, Dengue 4 NS1, Japanese Encephalitis virus NS1, St. Louis Encephalitis virus NS1, West Nile virus NS1, Zika virus NS1, and Yellow Fever virus NS1. It is understood and herein contemplated that the NS1 protein used in the assay can be from the same *Flavivirus* being detected or to which immune protection with a vaccine is sought (for example, a Dengue 1 NS1 for detection of Dengue 1 infection, a Dengue 2 NS1 for detection of Dengue 2 infection, a Dengue 3 NS1 for detection of Dengue 3 infection, a Dengue 4 NS1 for detection of Dengue 4 infection, a Yellow Fever virus NS1 for detection of Yellow Fever virus infection, a Zika virus NS1 for detection of Zika virus infection, a West Nile virus NS1 for detection of West Nile virus infection, a Japanese Encephalitis virus NS1 for detection of Japanese Encephalitis virus infection and St. Louis Encephalitis virus for detection of St. Louis Encephalitis virus infection).

In some instances, it can be advantageous to test for exposure to multiple flaviviruses. Thus, it is contemplated herein that he disclosed methods can utilize a panel of NS1 proteins from 1, 2, 3, 4, 5, 6, 7, 8, and/or 9 flaviviruses, including but not limited to Dengue 1 NS1, Dengue 2 NS1, Dengue 3 NS1, Dengue 4 NS1, Japanese Encephalitis virus NS1, St. Louis Encephalitis virus NS1, West Nile virus NS1, Zika virus NS1, and Yellow fever virus NS1. Due to cross-reactivity of some *Flavivirus* antigens, in some instances the detection of *Flavivirus* infection can be obtained through use of an NS1 protein from a *Flavivirus* other than the virus being detected. For example, detection of Dengue 1 infection can be obtained through use of a Dengue 2, Dengue 3, or Dengue 4 NS1. In some aspect, the NS1 can be a recombinant or synthetic NS1 specifically designed to avoid or reduce cross-reactivity or be cross reactive.

The disclosed methods utilize biological samples obtained from a subject to perform an immunoassay. In one aspect, the biological sample from the subject is whole blood, serum, Peripheral blood mononuclear cells (PBMC), saliva, urine, oral secretions, amniotic fluid, plasma, bone marrow, or cerebrospinal fluid (CSF). The biological sample can be obtained via any means known in the art for collecting tissue.

In some embodiments, measurements of the presence or amount of an antibody can be compared to a control. In some embodiments, a measured amount of an antibody (e.g., IgG3) in a biological sample can indicate an outcome when the measured amount is increased as compared to a control. In some embodiments, the measured amount of an antibody in a sample is at least 25% increased as compared to a control. In some embodiments, the measured amount of an antibody (e.g., IgG3) in a sample is at least 50%, at least 60%, at least 70%, at least 80%, at least 90%, at least 95%, at least 98%, or at least 99% increased as compared to a control. In some embodiments, the measured amount of an antibody (e.g., IgG3) in a sample is at least two-fold, at least three-fold, at least four-fold, at least five-fold, at least six-fold, at least seven-fold, at least eight-fold, at least nine-fold, or at least ten-fold increased as compared to a control.

The disclosed methods can use immunoassays to measure the antibody (e.g., IgG3) level specific to a *Flavivirus* NS1 protein. As such, an immunoassay can be used to determine the presence or amount of an antibody (e.g., an anti-NS1 IgG3 antibody) in a biological sample. The steps of various useful immunodetection methods have been described in the scientific literature, such as, e.g., Maggio et al., Enzyme-Immunoassay, (1987) and Nakamura, et al., Enzyme Immunoassays: Heterogeneous and Homogeneous Systems, Handbook of Experimental Immunology, Vol. 1: Immunochemistry, 27.1-27.20 (1986), each of which is incorporated herein by reference in its entirety and specifically for its teaching regarding immunodetection methods Immunoassays, in their most simple and direct sense, are binding assays involving binding between antibodies and antigen. Many types and formats of immunoassays are known and all are suitable for detecting the disclosed biomarkers. Examples of immunoassays are enzyme linked immunosorbent assays (ELISAs), radioimmunoassays (RIA), radioimmune precipitation assays (RIPA), immunobead capture assays, Western blotting, dot blotting, gel-shift assays, flow cytometry, protein arrays, multiplexed bead arrays, magnetic capture, in vivo imaging, fluorescence resonance energy transfer (FRET), and fluorescence recovery/localization after photobleaching (FRAP/FLAP). In some embodiments, the immunoassay used to detect anti-NS1 IgG3 is selected from the group consisting of enzyme linked immunosorbent assays (ELISAs), enzyme linked immunospot assays (ELIspot), radioimmunoassays (RIA), immunobead capture assays, Western blotting, dot blotting, gel-shift assays, intracellular cytokine stain, immunohistochemistry, protein arrays, and multiplexed bead arrays.

In general, immunoassays involve contacting a sample suspected of containing a molecule of interest (such as the disclosed biomarkers) with an antibody to the molecule of interest or contacting an antibody to a molecule of interest (such as antibodies to the disclosed biomarkers) with a molecule that can be bound by the antibody, as the case may be, under conditions effective to allow the formation of immunocomplexes. Contacting a sample with the antibody to the molecule of interest or with the molecule that can be bound by an antibody to the molecule of interest under conditions effective and for a period of time sufficient to allow the formation of immune complexes (primary immune complexes) is generally a matter of simply bringing into contact the molecule or antibody and the sample and incubating the mixture for a period of time sufficient for the antibodies to form immune complexes with, i.e., to bind to, any molecules (e.g., antigens) present to which the antibodies can bind. In many forms of immunoassay, the sample-antibody composition, such as a tissue section, ELISA plate, dot blot or Western blot, can then be washed to remove any non-specifically bound antibody species, allowing only those antibodies specifically bound within the primary immune complexes to be detected.

Immunoassays can include methods for detecting or quantifying the amount of a molecule of interest (such as the disclosed biomarkers or their antibodies) in a sample, which methods generally involve the detection or quantitation of any immune complexes formed during the binding process. In general, the detection of immunocomplex formation is well known in the art and can be achieved through the application of numerous approaches. These methods are generally based upon the detection of a label or marker, such as any radioactive, fluorescent, biological or enzymatic tags or any other known label.

As used herein, a label can include a fluorescent dye, a member of a binding pair, such as biotin/streptavidin, a metal (e.g., gold), or an epitope tag that can specifically interact with a molecule that can be detected, such as by producing a colored substrate or fluorescence. Substances suitable for detectably labeling proteins include fluorescent dyes (also known herein as fluorochromes and fluorophores) and enzymes that react with colorimetric substrates (e.g., horseradish peroxidase). The use of fluorescent dyes is generally preferred in the practice of the invention as they can be detected at very low amounts. Furthermore, in the case where multiple antigens are reacted with a single array, each antigen can be labeled with a distinct fluorescent compound for simultaneous detection. Labeled spots on the array are detected using a fluorimeter, the presence of a signal indicating an antigen bound to a specific antibody.

Fluorophores are compounds or molecules that luminesce. Typically, fluorophores absorb electromagnetic energy at one wavelength and emit electromagnetic energy at a second wavelength. Representative fluorophores include, but are not limited to, 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein; 5-Carboxytetramethylrhodamine (5-TAMRA); 5-Hydroxy Tryptamine (5-HAT); 5-ROX (carboxy-X-rhodamine); 6-Carboxyrhodamine 6G; 6-CR 6G; 6-JOE; 7-Amino-4-methylcoumarin; 7-Aminoactinomycin D (7-AAD); 7-Hydroxy-4I methylcoumarin; 9-Amino-6-chloro-2-methoxyacridine (ACMA); AB Q; Acid Fuchsin; Acridine Orange; Acridine Red; Acridine Yellow; Acriflavin; Acriflavin Feulgen SITSA; Aequorin (Photoprotein); AFPs—AutoFluorescent Protein—(Quantum Biotechnologies) see sgGFP, sgBFP; Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC, AMCA-S; Aminomethylcoumarin (AMCA); AMCA-X; Aminoactinomycin D; Aminocoumarin; Anilin Blue; Anthrocyl stearate; APC-Cy7; APTRA-BTC; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); BCECF (high pH); BCECF (low pH); Berberine Sulphate; Beta Lactamase; BFP blue shifted GFP (Y66H); Blue Fluorescent Protein; BFP/GFP FRET; Bimane; Bisbenzemide; Bisbenzimide (Hoechst); bis-BTC; Blancophor FFG; Blancophor SV; BOBO™-1; BOBO™-3; Bodipy492/515; Bodipy493/503; Bodipy500/510; Bodipy; 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; BTC; BTC-5N; Calcein; Calcein Blue; Calcium Crimson–; Calcium Green; Calcium Green-1 $Ca^{2+}$ Dye; Calcium Green-2 $Ca^{2+}$; Calcium Green-5N $Ca^{2+}$; Calcium Green-C18 $Ca^{2+}$; Calcium Orange; Calcofluor White; Carboxy-X-rhodamine (5-ROX); Cascade Blue™; Cascade Yellow; Catecholamine; CCF2 (GeneBlazer); CFDA; CFP (Cyan Fluorescent Protein); CFP/YFP FRET; Chlorophyll; Chromomycin A; Chromomycin A; CL-NERF; CMFDA; Coelenterazine; Coelenterazine cp; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM I Methylcoumarin; CTC; CTC Formazan; Cy2™; Cy3.1 8; Cy3.5™; Cy3™; Cy5.1 8; Cy5.5™; Cy5™; Cy7™; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3'DCFDA; DCFH (Dichlorodihydrofluorescein Diacetate); DDAO; DHR (Dihydorhodamine 123); Di-4-ANEPPS; Di-8-ANEPPS (non-ratio); DiA (4-Di 16-ASP); Dichlorodihydrofluorescein Diacetate (DCFH); DiD-Lipophilic Tracer; DiD (Di1C18(5)); DIDS; Dihydrorhodamine 123 (DHR); DiI (Di1C18(3)); I Dinitrophenol; DiO (DiOC18(3)); DiR; DiR (Di1C18(7)); DM-NERF (high pH); DNP; Dopamine; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (111) chloride; EYFP; Fast Blue; FDA; Feulgen (Pararosaniline); FIF (Formaldehyd Induced Fluorescence); FITC; Flazo Orange; Fluo-3; Fluo-4; Fluorescein (FITC); Fluorescein Diacetate; Fluoro-Emerald; Fluoro-Gold (Hydroxystilbamidine); Fluor-Ruby; FluorX; FM 1-43™; FM 4-46; Fura Red™ (high pH); Fura Red™/Fluo-3; Fura-2; Fura-2/BCECF; Genacryl Brilliant Red B; Genacryl Brilliant Yellow 10GF; Genacryl Pink 3G; Genacryl Yellow 5GF; GeneBlazer; (CCF2); GFP (S65T); GFP red shifted (rsGFP); GFP wild type' non-UV excitation (wtGFP); GFP wild type, UV excitation (wtGFP); GFPuv; Gloxalic Acid; Granular blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1, high calcium; Indo-1 low calcium; Indodicarbocyanine (DiD); Indotricarbocyanine (DiR); Intrawhite Cf; JC-1; JO JO-1; JO-PRO™-1; LaserPro; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO™-1; LO-PRO-1; Lucifer Yellow; LysoTracker™ Blue; LysoTracker™ Blue-White; LysoTracker™ Green; LysoTracker™ Red; LysoTracker™ Yellow; LysoSensor™ Blue; LysoSensor™ Green; LysoSensor™ Yellow/Blue; Mag Green; Magdala Red (Phloxin B); Mag-Fura Red; Mag-Fura-2; Mag-Fura-5; Mag-Indo-1; Magnesium Green™; Magnesium Orange; Malachite Green; Marina Blue™; I Maxilon Brilliant Flavin 10 GFF; Maxilon Brilliant Flavin 8 GFF; Merocyanin; Methoxycoumarin; MitoTracker™ Green FM; MitoTracker™ Orange; MitoTracker™ Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxedidole; Noradrenaline; Nuclear Fast Red; i Nuclear Yellow; Nylosan Brilliant lavin E8G; Oregon Green™; Oregon Green™ 488; Oregon Green™ 500; Oregon Green™ 514; Pacific Blue; Pararosaniline (Feulgen); PBFI; PE-CyS; PE-Cy7; PerCP; PerCP-Cy5.5; PE-TexasRed (Red 613); Phloxin B (Magdala Red); Phorwite AR; Phorwite BKL; Phorwite Rev; Phorwite RPA; Phosphine 3R; PhotoResist; Phycoerythrin B [PE]; Phycoerythrin R [PE]; PKH26 (Sigma); PKH67; PMIA; Pontochrome Blue Black; POPO™-1; POPO™-3; PO-PRO™-1; PO-I PRO-3; Primuline; Procion Yellow; Propidium lodid (Pl); PyMPO; Pyrene; Pyronine; Pyronine B; Pyrozal Brilliant Flavin 7GF; QSY 7; Quinacrine Mustard; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycocyanine; R-phycoerythrin (PE); rsGFP; S65A; S65C; S65L; S65T; Sapphire GFP; SBFI; Serotonin; Sevron Brilliant Red 2B; Sevron Brilliant Red 4G; Sevron I Brilliant Red B; Sevron Orange; Sevron Yellow L; sgBFP™ (super glow BFP); sgGFP™ (super glow GFP); SITS (Primuline; Stilbene Isothiosulphonic Acid); SNAFL calcein; SNAFL-1; SNAFL-2; SNARF calcein; SNARF1; Sodium Green™; SpectrumAqua; SpectrumGreen; SpectrumOrange; Spectrum Red; SPQ (6-methoxy-N-(3 sulfopropyl) quinolinium); Stilbene; Sulphorhodamine B and C; Sulphorhodamine Extra; SYTO™ 11; SYTO™ 12; SYTO™ 13; SYTO™ 14; SYTO™ 15; SYTO™ 16; SYTO™ 17; SYTO™ 18; SYTO™ 20; SYTO™ 21; SYTO™ 22; SYTO™23; SYTO™ 24; SYTO™ 25; SYTO™ 40; SYTO™ 41; SYTO™ 42; SYTO™ 43; SYTO™ 44; SYTO™ 45; SYTO™ 59; SYTO™ 60; SYTO™ 61; SYTO™ 62; SYTO™ 63; SYTO™ 64; SYTO™ 80; SYTO™ 81; SYTO™ 82; SYTO™ 83; SYTO™ 84; SYTO™ 85; SYTOX™ Blue; SYTOX™ Green; SYTOX™ Orange; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TON; Thiolyte; Thiozole Orange; Tinopol CBS (Calcofluor White); TIER; TO-PRO™-1; TO-PRO™-3; TO-PRO™-5; TOTO™-1; TOTO™-3; TRI-COLOR® (PE-Cy5®); TRITC TetramethylRodamineIsoThioCyanate; TrueBlue™; Tru Red; Ultralite; Uranine B; Uvitex SFC; wt GFP; WW 781; X-Rhodamine; XRITC; Xylene Orange; Y66F; Y66H; Y66W; Yellow GFP; YFP; YO-PRO™-1; YO-PRO™-3; YOYO™-1; YOYO™-1; SYBR™ Green; Thiazole orange (interchelating dyes); semiconductor nanoparticles such as quantum dots; or caged fluorophore (which can be activated with light or other electromagnetic energy source), or a combination thereof.

A modifier unit such as a radionuclide can be incorporated into or attached directly to any of the compounds described herein by halogenation. Examples of radionuclides useful in this embodiment include, but are not limited to, tritium, iodine-125, iodine-131, iodine-123, iodine-124, astatine-210, carbon-11, carbon-14, nitrogen-13, fluorine-18. In another aspect, the radionuclide can be attached to a linking group or bound by a chelating group, which is then attached to the compound directly or by means of a linker. Examples of radionuclides useful in the methods and kits disclosed herein include, but are not limited to, Tc-99m, Re-186, Ga-68, Re-188, Y-90, Sm-153, Bi-212, Cu-67, Cu-64, and Cu-62. Radiolabeling techniques such as these are routinely used in the radiopharmaceutical industry.

The radiolabeled compounds are useful as imaging agents to diagnose neurological disease (e.g., a neurodegenerative disease) or a mental condition or to follow the progression or treatment of such a disease or condition in a mammal (e.g., a human). The radiolabeled compounds described herein can be conveniently used in conjunction with imaging techniques such as positron emission tomography (PET) or single photon emission computerized tomography (SPECT).

Labeling can be either direct or indirect. In direct labeling, the detecting antibody (the antibody for the molecule of interest) or detecting molecule (the molecule that can be bound by an antibody to the molecule of interest) include a label. Detection of the label indicates the presence of the detecting antibody or detecting molecule, which in turn indicates the presence of the molecule of interest or of an antibody to the molecule of interest, respectively. In indirect labeling, an additional molecule or moiety is brought into contact with, or generated at the site of, the immunocomplex. For example, a signal-generating molecule or moiety such as an enzyme can be attached to or associated with the detecting antibody or detecting molecule. The signal-generating molecule can then generate a detectable signal at the site of the immunocomplex. For example, an enzyme, when supplied with suitable substrate, can produce a visible or detectable product at the site of the immunocomplex. ELISAs use this type of indirect labeling.

As another example of indirect labeling, an additional molecule (which can be referred to as a binding agent) that can bind to either the molecule of interest or to the antibody (primary antibody) to the molecule of interest, such as a second antibody to the primary antibody, can be contacted with the immunocomplex. The additional molecule can have a label or signal-generating molecule or moiety. The additional molecule can be an antibody, which can thus be termed a secondary antibody. Binding of a secondary antibody to the primary antibody can form a so-called sandwich with the first (or primary) antibody and the molecule of interest. The immune complexes can be contacted with the labeled, secondary antibody under conditions effective and for a period of time sufficient to allow the formation of secondary immune complexes. The secondary immune complexes can then be generally washed to remove any non-specifically bound labeled secondary antibodies, and the remaining label in the secondary immune complexes can then be detected. The additional molecule can also be or include one of a pair of molecules or moieties that can bind to each other, such as the biotin/avidin pair. In this mode, the detecting antibody or detecting molecule should include the other member of the pair.

Other modes of indirect labeling include the detection of primary immune complexes by a two-step approach. For example, a molecule (which can be referred to as a first binding agent), such as an antibody, that has binding affinity for the molecule of interest or corresponding antibody can be used to form secondary immune complexes, as described above. After washing, the secondary immune complexes can be contacted with another molecule (which can be referred to as a second binding agent) that has binding affinity for the first binding agent, again under conditions effective and for a period of time sufficient to allow the formation of immune complexes (thus forming tertiary immune complexes). The second binding agent can be linked to a detectable label or signal-generating molecule or moiety, allowing detection of the tertiary immune complexes thus formed. This system can provide for signal amplification.

Immunoassays that involve the detection of as substance, such as a protein or an antibody to a specific protein, include label-free assays, protein separation methods (i.e., electrophoresis), solid support capture assays, or in vivo detection. Label-free assays are generally diagnostic means of determining the presence or absence of a specific protein, or an antibody to a specific protein, in a sample. Protein separation methods are additionally useful for evaluating physical properties of the protein, such as size or net charge. Capture assays are generally more useful for quantitatively evaluating the concentration of a specific protein, or antibody to a specific protein, in a sample. Finally, in vivo detection is useful for evaluating the spatial expression patterns of the substance, i.e., where the substance can be found in a subject, tissue or cell.

Provided that the concentrations are sufficient, the molecular complexes ([Ab-Ag]n) generated by antibody—antigen interaction are visible to the naked eye, but smaller amounts may also be detected and measured due to their ability to scatter a beam of light. The formation of complexes indicates that both reactants are present, and in immunoprecipitation assays a constant concentration of a reagent antibody is used to measure specific antigen ([Ab-Ag]n), and reagent antigens are used to detect specific antibody ([Ab-Ag]n). If the reagent species is previously coated onto cells (as in hemagglutination assay) or very small particles (as in latex agglutination assay), "clumping" of the coated particles is visible at much lower concentrations. A variety of assays based on these elementary principles are in common use, including Ouchterlony immunodiffusion assay, rocket immunoelectrophoresis, and immunoturbidimetric and nephelometric assays. The main limitations of such assays are restricted sensitivity (lower detection limits) in comparison to assays employing labels and, in some cases, the fact that very high concentrations of analyte can actually inhibit complex formation, necessitating safeguards that make the procedures more complex. Some of these Group 1 assays date right back to the discovery of antibodies and none of them have an actual "label" (e.g. Ag-enz). Other kinds of immunoassays that are label free depend on immunosensors, and a variety of instruments that can directly detect antibody—antigen interactions are now commercially available. Most depend on generating an evanescent wave on a sensor surface with immobilized ligand, which allows continuous monitoring of binding to the ligand Immunosensors allow the easy investigation of kinetic interactions and, with the advent of lower-cost specialized instruments, may in the future find wide application in immunoanalysis.

The use of immunoassays to detect a specific protein can involve the separation of the proteins by electrophoresis. Electrophoresis is the migration of charged molecules in solution in response to an electric field. Their rate of migration depends on the strength of the field; on the net charge, size and shape of the molecules and also on the ionic strength, viscosity and temperature of the medium in which the molecules are moving. As an analytical tool, electrophoresis is simple, rapid and highly sensitive. It is used analytically to study the properties of a single charged species, and as a separation technique.

Generally, the sample is run in a support matrix such as paper, cellulose acetate, starch gel, agarose or polyacrylamide gel. The matrix inhibits convective mixing caused by heating and provides a record of the electrophoretic run: at the end of the run, the matrix can be stained and used for scanning, autoradiography or storage. In addition, the most commonly used support matrices—agarose and polyacrylamide—provide a means of separating molecules by size, in that they are porous gels. A porous gel may act as a sieve by retarding, or in some cases completely obstructing, the movement of large macromolecules while allowing smaller molecules to migrate freely. Because dilute agarose gels are generally more rigid and easy to handle than polyacrylamide of the same concentration, agarose is used to separate larger macromolecules such as nucleic acids, large proteins and protein complexes. Polyacrylamide, which is easy to handle and to make at higher concentrations, is used to separate most proteins and small oligonucleotides that require a small gel pore size for retardation.

Proteins are amphoteric compounds; their net charge therefore is determined by the pH of the medium in which they are suspended. In a solution with a pH above its isoelectric point, a protein has a net negative charge and migrates towards the anode in an electrical field. Below its isoelectric point, the protein is positively charged and migrates towards the cathode. The net charge carried by a protein is in addition independent of its size—i.e., the charge carried per unit mass (or length, given proteins and nucleic acids are linear macromolecules) of molecule differs from protein to protein. At a given pH therefore, and under non-denaturing conditions, the electrophoretic separation of proteins is determined by both size and charge of the molecules.

Sodium dodecyl sulfate (SDS) is an anionic detergent which denatures proteins by "wrapping around" the polypeptide backbone—and SDS binds to proteins fairly specifically in a mass ratio of 1.4:1. In so doing, SDS confers a negative charge to the polypeptide in proportion to its length. Further, it is usually necessary to reduce disulfide bridges in proteins (denature) before they adopt the random-coil configuration necessary for separation by size; this is done with 2-mercaptoethanol or dithiothreitol (DTT). In denaturing SDS-PAGE separations therefore, migration is determined not by intrinsic electrical charge of the polypeptide, but by molecular weight.

Determination of molecular weight is done by SDS-PAGE of proteins of known molecular weight along with the protein to be characterized. A linear relationship exists between the logarithm of the molecular weight of an SDS-denatured polypeptide, or native nucleic acid, and its Rf. The Rf is calculated as the ratio of the distance migrated by the molecule to that migrated by a marker dye-front. A simple way of determining relative molecular weight by electrophoresis (Mr) is to plot a standard curve of distance migrated vs. log 10 MW for known samples, and read off the log Mr of the sample after measuring distance migrated on the same gel.

In two-dimensional electrophoresis, proteins are fractionated first on the basis of one physical property, and, in a second step, on the basis of another. For example, isoelectric focusing can be used for the first dimension, conveniently carried out in a tube gel, and SDS electrophoresis in a slab gel can be used for the second dimension. One example of a procedure is that of O'Farrell, P. H., High Resolution Two-dimensional Electrophoresis of Proteins, J. Biol. Chem. 250:4007-4021 (1975), herein incorporated by reference in its entirety for its teaching regarding two-dimensional electrophoresis methods. Other examples include but are not limited to, those found in Anderson, L and Anderson, N G, High resolution two-dimensional electrophoresis of human plasma proteins, Proc. Natl. Acad. Sci. 74:5421-5425 (1977), Ornstein, L., Disc electrophoresis, L. Ann. N.Y. Acad. Sci. 121:321349 (1964), each of which is herein incorporated by reference in its entirety for teachings regarding electrophoresis methods. Laemmli, U.K., Cleavage of structural proteins during the assembly of the head of bacteriophage T4, Nature 227:680 (1970), which is herein incorporated by reference in its entirety for teachings regarding electrophoresis methods, discloses a discontinuous system for resolving proteins denatured with SDS. The leading ion in the Laemmli buffer system is chloride, and the trailing ion is glycine. Accordingly, the resolving gel and the stacking gel are made up in Tris-HCl buffers (of different concentration and pH), while the tank buffer is Tris-glycine. All buffers contain 0.1% SDS.

One example of an immunoassay that uses electrophoresis that is contemplated in the current methods is Western blot analysis. Western blotting or immunoblotting allows the determination of the molecular mass of a protein and the measurement of relative amounts of the protein present in different samples. Detection methods include chemiluminescence and chromagenic detection. Standard methods for Western blot analysis can be found in, for example, D. M. Bollag et al., *Protein Methods* (2d edition 1996) and E. Harlow & D. Lane, *Antibodies, a Laboratory Manual* (1988), U.S. Pat. No. 4,452,901, each of which is herein incorporated by reference in their entirety for teachings regarding Western blot methods. Generally, proteins are separated by gel electrophoresis, usually SDS-PAGE. The proteins are transferred to a sheet of special blotting paper, e.g., nitrocellulose, though other types of paper, or membranes, can be used. The proteins retain the same pattern of separation they had on the gel. The blot is incubated with a generic protein (such as milk proteins) to bind to any remaining sticky places on the nitrocellulose. An antibody is then added to the solution which is able to bind to its specific protein.

The attachment of specific antibodies to specific immobilized antigens can be readily visualized by indirect enzyme immunoassay techniques, usually using a chromogenic substrate (e.g. alkaline phosphatase or horseradish peroxidase) or chemiluminescent substrates. Other possibilities for probing include the use of fluorescent or radioisotope labels (e.g., fluorescein, $^{125}I$). Probes for the detection of antibody binding can be conjugated anti-immunoglobulins, conjugated staphylococcal Protein A (binds IgG), or probes to biotinylated primary antibodies (e.g., conjugated avidin/streptavidin).

The power of the technique lies in the simultaneous detection of a specific protein by means of its antigenicity, and its molecular mass. Proteins are first separated by mass in the SDS-PAGE, then specifically detected in the immunoassay step. Thus, protein standards (ladders) can be run simultaneously in order to approximate molecular mass of the protein of interest in a heterogeneous sample.

The gel shift assay or electrophoretic mobility shift assay (EMSA) can be used to detect the interactions between DNA binding proteins and their cognate DNA recognition sequences, in both a qualitative and quantitative manner Exemplary techniques are described in Ornstein L., Disc electrophoresis-I: Background and theory, Ann. NY Acad. Sci. 121:321-349 (1964), and Matsudiara, P T and D R Burgess, SDS microslab linear gradient polyacrylamide gel electrophoresis, Anal. Biochem. 87:386-396 (1987), each of which is herein incorporated by reference in its entirety for teachings regarding gel-shift assays.

In a general gel-shift assay, purified proteins or crude cell extracts can be incubated with a labeled (e.g., $^{32}P$-radiolabeled) DNA or RNA probe, followed by separation of the complexes from the free probe through a nondenaturing polyacrylamide gel. The complexes migrate more slowly through the gel than unbound probe. Depending on the activity of the binding protein, a labeled probe can be either double-stranded or single-stranded. For the detection of DNA binding proteins such as transcription factors, either purified or partially purified proteins, or nuclear cell extracts can be used. For detection of RNA binding proteins, either purified or partially purified proteins, or nuclear or cytoplasmic cell extracts can be used. The specificity of the DNA or RNA binding protein for the putative binding site is established by competition experiments using DNA or RNA fragments or oligonucleotides containing a binding site for the protein of interest, or other unrelated sequence. The differences in the nature and intensity of the complex formed in the presence of specific and nonspecific competitor allows identification of specific interactions. Refer to Promega, Gel Shift Assay FAQ, available at www.promega.com/faq/gelshfaq.html (last visited Mar. 25, 2005), which is herein incorporated by reference in its entirety for teachings regarding gel shift methods.

Gel shift methods can include using, for example, colloidal forms of COOMASSIE (Imperial Chemicals Industries, Ltd) blue stain to detect proteins in gels such as polyacrylamide electrophoresis gels. Such methods are described, for example, in Neuhoff et al., Electrophoresis 6:427-448 (1985), and Neuhoff et al., Electrophoresis 9:255-262 (1988), each of which is herein incorporated by reference in its entirety for teachings regarding gel shift methods. In addition to the conventional protein assay methods referenced above, a combination cleaning and protein staining composition is described in U.S. Pat. No. 5,424,000, herein incorporated by reference in its entirety for its teaching regarding gel shift methods. The solutions can include phosphoric, sulfuric, and nitric acids, and Acid Violet dye.

Radioimmune Precipitation Assay (RIPA) is a sensitive assay using radiolabeled antigens to detect specific antibodies in serum. The antigens are allowed to react with the serum and then precipitated using a special reagent such as, for example, protein A sepharose beads. The bound radiolabeled immunoprecipitate is then commonly analyzed by gel electrophoresis. Radioimmunoprecipitation assay (RIPA) is often used as a confirmatory test for diagnosing the presence of HIV antibodies. RIPA is also referred to in the art as Farr Assay, Precipitin Assay, Radioimmune Precipitin Assay; Radioimmunoprecipitation Analysis; Radioimmunoprecipitation Analysis, and Radioimmunoprecipitation Analysis.

While the above immunoassays that utilize electrophoresis to separate and detect the specific proteins of interest allow for evaluation of protein size, they are not very sensitive for evaluating protein concentration. However, also contemplated are immunoassays wherein the protein or antibody specific for the protein is bound to a solid support (e.g., tube, well, bead, or cell) to capture the antibody or protein of interest, respectively, from a sample, combined with a method of detecting the protein or antibody specific for the protein on the support. Examples of such immunoassays include Radioimmunoassay (RIA), Enzyme-Linked Immunosorbent Assay (ELISA), Flow cytometry, protein array, multiplexed bead assay, and magnetic capture.

Radioimmunoassay (RIA) is a classic quantitative assay for detection of antigen-antibody reactions using a radioactively labeled substance (radioligand), either directly or indirectly, to measure the binding of the unlabeled substance to a specific antibody or other receptor system. Radioimmunoassay is used, for example, to test hormone levels in the blood without the need to use a bioassay. Non-immunogenic substances (e.g., haptens) can also be measured if coupled to larger carrier proteins (e.g., bovine gamma-globulin or human serum albumin) capable of inducing antibody formation. RIA involves mixing a radioactive antigen (because of the ease with which iodine atoms can be introduced into tyrosine residues in a protein, the radioactive isotopes $^{125}$I or $^{131}$I are often used) with antibody to that antigen. The antibody is generally linked to a solid support, such as a tube or beads. Unlabeled or "cold" antigen is then adding in known quantities and measuring the amount of labeled antigen displaced. Initially, the radioactive antigen is bound to the antibodies. When cold antigen is added, the two compete for antibody binding sites—and at higher concentrations of cold antigen, more binds to the antibody, displacing the radioactive variant. The bound antigens are separated from the unbound ones in solution and the radioactivity of each used to plot a binding curve. The technique is both extremely sensitive, and specific.

Enzyme-Linked Immunosorbent Assay (ELISA), or more generically termed EIA (Enzyme ImmunoAssay), is an immunoassay that can detect an antibody specific for a protein. In such an assay, a detectable label bound to either an antibody-binding or antigen-binding reagent is an enzyme. When exposed to its substrate, this enzyme reacts in such a manner as to produce a chemical moiety which can be detected, for example, by spectrophotometric, fluorometric or visual means. Enzymes which can be used to detectably label reagents useful for detection include, but are not limited to, horseradish peroxidase, alkaline phosphatase, glucose oxidase, β-galactosidase, ribonuclease, urease, catalase, malate dehydrogenase, staphylococcal nuclease, asparaginase, yeast alcohol dehydrogenase, alpha-glycerophosphate dehydrogenase, triose phosphate isomerase, glucose-6-phosphate dehydrogenase, glucoamylase and acetylcholinesterase.

Variations of ELISA techniques are known to those of skill in the art. In one variation, antibodies that can bind to proteins can be immobilized onto a selected surface exhibiting protein affinity, such as a well in a polystyrene microtiter plate. Then, a test composition suspected of containing a marker antigen can be added to the wells. After binding and washing to remove non-specifically bound immunocomplexes, the bound antigen can be detected. Detection can be achieved by the addition of a second antibody specific for the target protein, which is linked to a detectable label. This type of ELISA is a simple "sandwich ELISA." Detection also can be achieved by the addition of a second antibody, followed by the addition of a third antibody that has binding affinity for the second antibody, with the third antibody being linked to a detectable label.

Another variation is a competition ELISA. In competition ELISA's, test samples compete for binding with known amounts of labeled antigens or antibodies. The amount of reactive species in the sample can be determined by mixing the sample with the known labeled species before or during incubation with coated wells. The presence of reactive species in the sample acts to reduce the amount of labeled species available for binding to the well and thus reduces the ultimate signal.

Regardless of the format employed, ELISAs have certain features in common, such as coating, incubating or binding, washing to remove non-specifically bound species, and detecting the bound immunocomplexes. Antigen or antibodies can be linked to a solid support, such as in the form of plate, beads, dipstick, membrane or column matrix, and the sample to be analyzed applied to the immobilized antigen or antibody. In coating a plate with either antigen or antibody, one will generally incubate the wells of the plate with a solution of the antigen or antibody, either overnight or for a specified period of hours. The wells of the plate can then be washed to remove incompletely adsorbed material. Any remaining available surfaces of the wells can then be "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, a secondary or tertiary detection means rather than a direct procedure can also be used. Thus, after binding of a protein or antibody to the well, coating with a non-reactive material to reduce background, and washing to remove unbound material, the immobilizing surface is contacted with the control clinical or biological sample to be tested under conditions effective to allow immunocomplex (antigen/antibody) formation. Detection of the immunocomplex then requires a labeled secondary binding agent or a secondary binding agent in conjunction with a labeled third binding agent.

Enzyme-Linked Immunospot Assay (ELISPOT) is an immunoassay that can detect an antibody specific for a protein or antigen. In such an assay, a detectable label bound to either an antibody-binding or antigen-binding reagent is an enzyme. When exposed to its substrate, this enzyme reacts in such a manner as to produce a chemical moiety which can be detected, for example, by spectrophotometric, fluorometric or visual means. Enzymes which can be used to detectably label reagents useful for detection include, but are not limited to, horseradish peroxidase, alkaline phosphatase, glucose oxidase, β-galactosidase, ribonuclease, urease, catalase, malate dehydrogenase, staphylococcal nuclease, asparaginase, yeast alcohol dehydrogenase, alpha-glycerophosphate dehydrogenase, triose phosphate isomerase, glucose-6-phosphate dehydrogenase, glucoamylase and acetylcholinesterase. In this assay a nitrocellulose microtiter plate is coated with antigen. The test sample is exposed to the antigen and then reacted similarly to an ELISA assay. Detection differs from a traditional ELISA in that detection is determined by the enumeration of spots on the nitrocellulose plate. The presence of a spot indicates that the sample reacted to the antigen. The spots can be counted and the number of cells in the sample specific for the antigen determined.

"Under conditions effective to allow immunocomplex (antigen/antibody) formation" means that the conditions include diluting the antigens and antibodies with solutions such as BSA, bovine gamma globulin (BGG) and phosphate buffered saline (PBS)/TWEEN® so as to reduce non-specific binding and to promote a reasonable signal to noise ratio.

The suitable conditions also mean that the incubation is at a temperature and for a period of time sufficient to allow effective binding. Incubation steps can typically be from about 1 minute to twelve hours, at temperatures of about 20° to 30° C., or can be incubated overnight at about 0° C. to about 10° C.

Following all incubation steps in an ELISA, the contacted surface can be washed so as to remove non-complexed material. A washing procedure can include washing with a solution such as PBS/TWEEN®20 or borate buffer. Following the formation of specific immunocomplexes between the test sample and the originally bound material, and subsequent washing, the occurrence of even minute amounts of immunocomplexes can be determined.

To provide a detecting means, the second or third antibody can have an associated label to allow detection, as described above. This can be an enzyme that can generate color development upon incubating with an appropriate chromogenic substrate. Thus, for example, one can contact and incubate the first or second immunocomplex with a labeled antibody for a period of time and under conditions that favor the development of further immunocomplex formation (e.g., incubation for 2 hours at room temperature in a PBS-containing solution such as PBS-TWEEN®).

After incubation with the labeled antibody, and subsequent to washing to remove unbound material, the amount of label can be quantified, e.g., by incubation with a chromogenic substrate such as urea and bromocresol purple or 2,2'-azido-di-(3-ethyl-benzthiazoline-6-sulfonic acid [ABTS] and $H_2O_2$, in the case of peroxidase as the enzyme label. Quantitation can then be achieved by measuring the degree of color generation, e.g., using a visible spectra spectrophotometer.

Protein arrays are solid-phase ligand binding assay systems using immobilized proteins on surfaces which include glass, membranes, microtiter wells, mass spectrometer plates, and beads or other particles. The assays are highly parallel (multiplexed) and often miniaturized (microarrays, protein chips). Their advantages include being rapid and automatable, capable of high sensitivity, economical on reagents, and giving an abundance of data for a single experiment. Bioinformatics support is important; the data handling demands sophisticated software and data comparison analysis. However, the software can be adapted from that used for DNA arrays, as can much of the hardware and detection systems.

One of the chief formats is the capture array, in which ligand-binding reagents, which are usually antibodies but can also be alternative protein scaffolds, peptides or nucleic acid aptamers, are used to detect target molecules in mixtures such as plasma or tissue extracts. In diagnostics, capture arrays can be used to carry out multiple immunoassays in parallel, both testing for several analytes in individual sera for example and testing many serum samples simultaneously. In proteomics, capture arrays are used to quantitate and compare the levels of proteins in different samples in health and disease, i.e. protein expression profiling. Proteins other than specific ligand binders are used in the array format for in vitro functional interaction screens such as protein-protein, protein-DNA, protein-drug, receptor-ligand, enzyme-substrate, etc. The capture reagents themselves are selected and screened against many proteins, which can also be done in a multiplex array format against multiple protein targets.

For construction of arrays, sources of proteins include cell-based expression systems for recombinant proteins, purification from natural sources, production in vitro by cell-free translation systems, and synthetic methods for peptides. Many of these methods can be automated for high throughput production. For capture arrays and protein function analysis, it is important that proteins should be correctly folded and functional; this is not always the case, e.g. where recombinant proteins are extracted from bacteria under denaturing conditions. Nevertheless, arrays of denatured proteins are useful in screening antibodies for cross-reactivity, identifying autoantibodies and selecting ligand binding proteins.

Protein arrays have been designed as a miniaturization of familiar immunoassay methods such as ELISA and dot blotting, often utilizing fluorescent readout, and facilitated by robotics and high throughput detection systems to enable multiple assays to be carried out in parallel. Commonly used physical supports include glass slides, silicon, microwells, nitrocellulose or PVDF membranes, and magnetic and other microbeads. While microdrops of protein delivered onto planar surfaces are the most familiar format, alternative architectures include CD centrifugation devices based on developments in microfluidics (Gyros, Monmouth Junction, N.J.) and specialized chip designs, such as engineered microchannels in a plate (e.g., The Living Chip™, Biotrove, Woburn, Mass.) and tiny 3D posts on a silicon surface (Zyomyx, Hayward Calif.). Particles in suspension can also be used as the basis of arrays, providing they are coded for identification; systems include color coding for microbeads (Luminex, Austin, Tex.; Bio-Rad Laboratories) and semiconductor nanocrystals (e.g., QDots™, Quantum Dot, Hayward, Calif.), and barcoding for beads (UltraPlex™, SmartBead Technologies Ltd, Babraham, Cambridge, UK) and multimetal microrods (e.g., Nanobarcodes™ particles, Nanoplex Technologies, Mountain View, Calif.). Beads can also be assembled into planar arrays on semiconductor chips (LEAPS technology, BioArray Solutions, Warren, N.J.).

Immobilization of proteins involves both the coupling reagent and the nature of the surface being coupled to. A good protein array support surface is chemically stable before and after the coupling procedures, allows good spot morphology, displays minimal nonspecific binding, does not contribute a background in detection systems, and is compatible with different detection systems. The immobilization method used are reproducible, applicable to proteins of different properties (size, hydrophilic, hydrophobic), amenable to high throughput and automation, and compatible with retention of fully functional protein activity. Orientation of the surface-bound protein is recognized as an important factor in presenting it to ligand or substrate in an active state; for capture arrays the most efficient binding results are obtained with orientated capture reagents, which generally require site-specific labeling of the protein.

Both covalent and noncovalent methods of protein immobilization are used and have various pros and cons. Passive adsorption to surfaces is methodologically simple, but allows little quantitative or orientational control; it may or may not alter the functional properties of the protein, and reproducibility and efficiency are variable. Covalent coupling methods provide a stable linkage, can be applied to a range of proteins and have good reproducibility; however, orientation may be variable, chemical derivatization may alter the function of the protein and requires a stable interactive surface. Biological capture methods utilizing a tag on the protein provide a stable linkage and bind the protein specifically and in reproducible orientation, but the biological reagent must first be immobilized adequately, and the array may require special handling and have variable stability.

Several immobilization chemistries and tags have been described for fabrication of protein arrays. Substrates for covalent attachment include glass slides coated with amino- or aldehyde-containing silane reagents. In the Versalinx™ system (Prolinx, Bothell, Wash.) reversible covalent coupling is achieved by interaction between the protein derivatized with phenyldiboronic acid, and salicylhydroxamic acid immobilized on the support surface. This also has low background binding and low intrinsic fluorescence and allows the immobilized proteins to retain function. Noncovalent binding of unmodified protein occurs within porous structures such as HydroGel™ (PerkinElmer, Wellesley, Mass.), based on a 3-dimensional polyacrylamide gel; this substrate is reported to give a particularly low background on glass microarrays, with a high capacity and retention of protein function. Widely used biological coupling methods are through biotin/streptavidin or hexahistidine/Ni interactions, having modified the protein appropriately. Biotin may be conjugated to a poly-lysine backbone immobilized on a surface such as titanium dioxide (Zyomyx) or tantalum pentoxide (Zeptosens, Witterswil, Switzerland).

Array fabrication methods include robotic contact printing, ink-jetting, piezoelectric spotting and photolithography. A number of commercial arrayers are available [e.g. Packard Biosciences] as well as manual equipment [V & P Scientific]. Bacterial colonies can be robotically gridded onto PVDF membranes for induction of protein expression in situ.

At the limit of spot size and density are nanoarrays, with spots on the nanometer spatial scale, enabling thousands of reactions to be performed on a single chip less than 1 mm square. BioForce Laboratories have developed nanoarrays with 1521 protein spots in 85 sq microns, equivalent to 25 million spots per sq cm, at the limit for optical detection; their readout methods are fluorescence and atomic force microscopy (AFM).

Fluorescence labeling and detection methods are widely used. The same instrumentation as used for reading DNA microarrays is applicable to protein arrays. For differential display, capture (e.g., antibody) arrays can be probed with fluorescently labeled proteins from two different cell states, in which cell lysates are directly conjugated with different fluorophores (e.g. Cy-3, Cy-5) and mixed, such that the color acts as a readout for changes in target abundance. Fluorescent readout sensitivity can be amplified 10-100 fold by tyramide signal amplification (TSA) (PerkinElmer Lifesciences). Planar waveguide technology (Zeptosens) enables ultrasensitive fluorescence detection, with the additional advantage of no intervening washing procedures. High sensitivity can also be achieved with suspension beads and particles, using phycoerythrin as label (Luminex) or the properties of semiconductor nanocrystals (Quantum Dot). A number of novel alternative readouts have been developed, especially in the commercial biotech arena. These include adaptations of surface plasmon resonance (HTS Biosystems, Intrinsic Bioprobes, Tempe, Ariz.), rolling circle DNA amplification (Molecular Staging, New Haven Conn.), mass spectrometry (Intrinsic Bioprobes; Ciphergen, Fremont, Calif.), resonance light scattering (Genicon Sciences, San Diego, Calif.) and atomic force microscopy [BioForce Laboratories].

Capture arrays form the basis of diagnostic chips and arrays for expression profiling. They employ high affinity capture reagents, such as conventional antibodies, single domains, engineered scaffolds, peptides or nucleic acid aptamers, to bind and detect specific target ligands in high throughput manner.

Antibody arrays have the required properties of specificity and acceptable background, and some are available commercially (BD Biosciences, San Jose, Calif.; Clontech, Mountain View, Calif.; BioRad; Sigma, St. Louis, Mo.). Antibodies for capture arrays are made either by conventional immunization (polyclonal sera and hybridomas), or as recombinant fragments, usually expressed in *E. coli*, after selection from phage or ribosome display libraries (Cambridge Antibody Technology, Cambridge, UK; BioInvent, Lund, Sweden; Affitech, Walnut Creek, Calif.; Biosite, San Diego, Calif.). In addition to the conventional antibodies, Fab and scFv fragments, single V-domains from camelids or engineered human equivalents (Domantis, Waltham, Mass.) may also be useful in arrays.

The term "scaffold" refers to ligand-binding domains of proteins, which are engineered into multiple variants capable of binding diverse target molecules with antibody-like properties of specificity and affinity. The variants can be produced in a genetic library format and selected against individual targets by phage, bacterial or ribosome display. Such ligand-binding scaffolds or frameworks include 'Affibodies' based on Staph. aureus protein A (Affibody, Bromma, Sweden), 'Trinectins' based on fibronectins (Phylos, Lexington, Mass.) and 'Anticalins' based on the lipocalin structure (Pieris Proteolab, Freising-Weihenstephan, Germany). These can be used on capture arrays in a similar fashion to antibodies and may have advantages of robustness and ease of production. For example, scaffold proteins, like Top7 can be used as carrier of NS1 epitopes and then used as antigens in immune assays. So small immune dominant fragments of NS1 can be incorporated as antigens. In one aspect, disclosed herein the disclosed methods rather than contacting the biological sample with one or more *Flavivirus* NS1 proteins comprise contacting the biological sample with one or more *Flavivirus* NS1 immuno dominant epitopes; wherein the immune dominant epitopes of NS1 are inserted as peptides into a scaffold protein, such as, for example Top 7.

Nonprotein capture molecules, notably the single-stranded nucleic acid aptamers which bind protein ligands with high specificity and affinity, are also used in arrays (SomaLogic, Boulder, Colo.). Aptamers are selected from libraries of oligonucleotides by the Selex™ procedure and their interaction with protein can be enhanced by covalent attachment, through incorporation of brominated deoxyuridine and UV-activated crosslinking (photoaptamers). Photocrosslinking to ligand reduces the crossreactivity of aptamers due to the specific steric requirements. Aptamers have the advantages of ease of production by automated oligonucleotide synthesis and the stability and robustness of DNA; on photoaptamer arrays, universal fluorescent protein stains can be used to detect binding.

Protein analytes binding to antibody arrays may be detected directly or via a secondary antibody in a sandwich assay. Direct labelling is used for comparison of different samples with different colors. Where pairs of antibodies directed at the same protein ligand are available, sandwich immunoassays provide high specificity and sensitivity and are therefore the method of choice for low abundance proteins such as cytokines; they also give the possibility of detection of protein modifications. Label-free detection methods, including mass spectrometry, surface plasmon resonance and atomic force microscopy, avoid alteration of ligand. What is required from any method is optimal sensitivity and specificity, with low background to give high signal to noise. Since analyte concentrations cover a wide range, sensitivity has to be tailored appropriately; serial dilution of the sample or use of antibodies of different affinities are solutions to this problem. Proteins of interest are frequently those in low concentration in body fluids and extracts, requiring detection in the pg range or lower, such as cytokines or the low expression products in cells.

An alternative to an array of capture molecules is one made through 'molecular imprinting' technology, in which peptides (e.g., from the C-terminal regions of proteins) are used as templates to generate structurally complementary, sequence-specific cavities in a polymerizable matrix; the cavities can then specifically capture (denatured) proteins that have the appropriate primary amino acid sequence (ProteinPrint™, Aspira Biosystems, Burlingame, Calif.).

Another methodology which can be used diagnostically and in expression profiling is the ProteinChip® array (Ciphergen, Fremont, Calif.), in which solid phase chromatographic surfaces bind proteins with similar characteristics of charge or hydrophobicity from mixtures such as plasma or tumor extracts, and SELDI-TOF mass spectrometry is used to detection the retained proteins.

Large-scale functional chips have been constructed by immobilizing large numbers of purified proteins and used to assay a wide range of biochemical functions, such as protein interactions with other proteins, drug-target interactions, enzyme-substrates, etc. Generally, they require an expression library, cloned into *E. coli*, yeast or similar from which the expressed proteins are then purified, e.g. via a His tag, and immobilized. Cell free protein transcription/translation is a viable alternative for synthesis of proteins which do not express well in bacterial or other in vivo systems.

For detecting protein-protein interactions, protein arrays can be in vitro alternatives to the cell-based yeast two-hybrid system and may be useful where the latter is deficient, such as interactions involving secreted proteins or proteins with disulfide bridges. High-throughput analysis of biochemical activities on arrays has been described for yeast protein kinases and for various functions (protein-protein and protein-lipid interactions) of the yeast proteome, where a large proportion of all yeast open-reading frames was expressed and immobilized on a microarray. Large-scale 'proteome chips' promise to be very useful in identification of functional interactions, drug screening, etc. (Proteometrix, Branford, Conn.).

As a two-dimensional display of individual elements, a protein array can be used to screen phage or ribosome display libraries, in order to select specific binding partners, including antibodies, synthetic scaffolds, peptides and aptamers. In this way, 'library against library' screening can be carried out. Screening of drug candidates in combinatorial chemical libraries against an array of protein targets identified from genome projects is another application of the approach.

A multiplexed bead assay, such as, for example, the BD™ Cytometric Bead Array, is a series of spectrally discrete particles that can be used to capture and quantitate soluble analytes. The analyte is then measured by detection of a fluorescence-based emission and flow cytometric analysis. Multiplexed bead assay generates data that is comparable to ELISA based assays, but in a "multiplexed" or simultaneous fashion. Concentration of unknowns is calculated for the cytometric bead array as with any sandwich format assay, i.e. through the use of known standards and plotting unknowns against a standard curve. Further, multiplexed bead assay allows quantification of soluble analytes in samples never previously considered due to sample volume limitations. In addition to the quantitative data, powerful visual images can be generated revealing unique profiles or signatures that provide the user with additional information at a glance.

Kits

Also disclosed herein are kits drawn to reagents that can be used in practicing the methods disclosed herein. Such kits can be useful for determining the recency of infection, determining infection prior to vaccination, determining the efficacy of a vaccine, identifying infection by a *Flavivirus* such as Zika during gestation, evaluating the risk of a congenital syndrome such as Zika syndrome, and/or determining the emergence of a vaccine-resistant strain of *Flavivirus*. In other kits, such kits can be useful for detecting a prior Dengue virus infection. The kits can include any reagent or combination of reagents discussed herein or that would be understood to be required or beneficial in the practice of the disclosed methods. For example, the kits can include NS1 proteins from one or more flaviviruses and labeled anti-IgG antibodies for the detection of anti-IgG3 or anti-IgG antibodies, as well as the buffers, plasticware (microtiter plates, tubes, membrane microtiter plates) and enzymes required to perform the assay. For example, disclosed is a kit for detecting a recent *Flavivirus* infection, vaccine efficacy, or the emergence of a vaccine-resistant strain of *Flavivirus* comprising one or more *Flavivirus* NS1 proteins; an anti-IgG3 antibody; an anti-IgG1 antibody, an anti-IgG2 antibody; an anti-IgG4 antibody; a total anti-IgG antibody, and/or an anti-IgM antibody. As another example, disclosed is a kit for detecting a prior Dengue virus infection; an anti-IgG3 antibody; an anti-IgG1 antibody, an anti-IgG2 antibody; an anti-IgG4 antibody; a total anti-IgG antibody, and/or an anti-IgM antibody.

In some embodiments, the one or more NS1 proteins of the kits are selected from the group consisting of Dengue 1 NS1, Dengue 2 NS1, Dengue 3 NS1, Dengue 4 NS1, Japanese Encephalitis virus NS1, St. Louis Encephalitis virus NS1, West Nile virus NS1, Zika virus NS1, and Yellow fever virus NS1. In some embodiments, the one or more NS1 proteins of the kits are selected from the group consisting of Dengue 1 NS1, Dengue 2 NS1, Dengue 3 NS1, and Dengue 4 NS1. In some embodiments, the NS1 protein used in the kit can be from the same *Flavivirus*, or even the Dengue virus, being detected by the kit (for example, a Dengue 1 NS1 for detection of Dengue 1 infection, a Dengue 2 NS1 for detection of Dengue 2 infection, a Dengue 3 NS1 for detection of Dengue 3 infection, a Dengue 4 NS1 for detection of Dengue 4 infection, a Yellow Fever virus NS1 for detection of Yellow Fever virus infection, a Zika virus NS1 for detection of Zika virus infection, a West Nile virus NS1 for detection of West Nile virus infection, a Japanese Encephalitis virus NS1 for detection of Japanese Encephalitis virus infection, and St. Louis Encephalitis virus for detection of St. Louis Encephalitis virus infection). In some embodiments, the kits can comprise NS1 peptide epitopes in a scaffold. In some instances, it can be advantageous to test for infection by multiple flaviviruses, or even infection by multiple Dengue viruses. Thus, it is contemplated herein that the disclosed kits can include a panel of NS1 proteins from 1, 2, 3, 4, 5, 6, 7, 8, and/or 9 flaviviruses, including but not limited to Dengue 1 NS1, Dengue 2 NS1, Dengue 3 NS1, Dengue 4 NS1, Japanese Encephalitis virus NS1, St. Louis Encephalitis virus NS1, West Nile virus NS1, Zika virus NS1, and Yellow fever virus NS1. It is also contemplated herein that the disclosed kits can include a panel of NS1 proteins from 1, 2, 3, 4, 5, 6, 7, 8, and/or 9 flaviviruses, including but not limited to Dengue 1 NS1, Dengue 2 NS1, Dengue 3 NS1, and Dengue 4 NS1, including various strains thereof. Due to cross-reactivity of some *Flavivirus* antigens, in some instances the detection of *Flavivirus* infection can be obtained through use of an NS1 proteins in kits from flaviviruses other than the virus being detected. For example, detection of Dengue 1 can be obtained using a kit comprising an NS1 protein form a Dengue 2, Dengue 3, or Dengue 4 NS1. In some aspect, the NS1 can be a recombinant or synthetic NS1 specifically designed to avoid or reduce cross-reactivity or be cross reactive.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1: Detection of Long Term and Recent Dengue Virus Infections

Summary

Dengue virus (DENV) infections elicit antibody responses to the non-structural protein 1 (NS1) that are associated with protection against disease. However, the antibody isotypes and subclasses involved, and their kinetics have not been extensively studied. The antibody responses to DENV NS1 were characterized by Enzyme-Linked Immunosorbent Assay (ELISA) in a longitudinal cohort of 266 confirmed dengue cases in Recife, Northeast Brazil. Samples were collected during the febrile phase and up to over 3 years after onset of symptoms. The antibodies investigated [IgA, IgM, IgG (including IgG2, IgG3 and IgG4 subclasses)] had distinct kinetic profiles following primary or secondary DENV infections. Of interest, most of these antibodies were consistently detected more than 6 months after onset of symptoms, except for IgG3. Anti-dengue NS1-specific IgG was consistently detected from the acute phase to beyond 3 years after symptom onset. In contrast, anti-dengue NS1-specific IgG3 was detected within the first week, peaked at week 2-3, and disappeared within 4-6 months after onset of symptoms. The mean duration of the IgG3 positive signal was 149 days (ranging from 126 to 172 days). Thus, anti-dengue NS1-specific IgG and IgG3 are demonstrated herein as biomarkers of long-term and recent (less than 6 months) DENV infections, respectively.

Material and Methods

Abbreviations: CYD-TDV, recombinant, live, attenuated, tetravalent dengue vaccine; DENV, dengue virus; IgG, immunoglobulin G; DF, dengue fever; DFC, complicated dengue fever; DHF, dengue hemorrhagic fever; NS1, dengue non-structural protein 1; $EC_{50}$, half maximal effective concentration; ELISA, enzyme-linked immunosorbent assay; GMC, geometric mean concentration; IQC, internal quality control; IVIG, reference generated using purified immunoglobulin; JEV, Japanese encephalitis virus; LLOQ, lower limit of quantitation; PCR, polymerase chain reaction; PRNT, plaque reduction neutralization test; ROC, receiver operating characteristic; TBEV, tick-borne encephalitis virus; USUV, Usutu virus; WNV, West Nile virus; ZIKV, Zika virus.

NS1 antigens. Recombinant proteins expressed in the mammalian cell line 293 were purchased from the Native Antigen Company (Oxfordshire, UK) and included DENV1 (strain Nauru/Western Pacific/1974), DENV2 (strain Thailand/16681/84), DENV3 (strain Sri Lanka D3/H/IMTSSA-SRI/2000/1266) and DENV4 (strain Dominica/814669/1981) NS1, Yellow Fever virus (YFV; strain 17D) NS1 and West Nile virus (WNV; strain NY99) NS1.

Positive and negative controls for anti-dengue NS1 IgG ELISA. Pooled immunoglobulins for intravenous injection (IVIg) purified from healthy donors from dengue endemic areas (LFB Biomedicaments, Courtaboeuf Cedex, France) was reconstituted in human IgG-depleted serum (Molecular Innovation, Novi, USA) at 50 mg/mL and used as positive control in the anti-dengue NS1 total IgG ELISA (here referred to as dengue NS1 IgG ELISA where a conjugate specific to all IgG subclasses was used). Pooled serum samples from confirmed dengue cases, 20 to 30 days after onset of symptoms (recent infection), were used as positive control in the anti-dengue NS1 IgA, IgM, IgG2, IgG3 and IgG4 enzyme-linked immunosorbent assays (ELISAs).

A dengue naive human type AB serum from healthy individuals from USA (MP Biomedicals, Solon, USA) was used as negative control for the IgG, IgG2, IgG3, IgM and IgA ELISA. A sample from one dengue immune subject exposed to dengue virus 10 years prior sample collection was used as negative control for IgG3 ELISA.

Hyperimmune serum samples of other flaviviruses. Hyperimmune serum samples against YFV antigens were obtained from a well-characterized cohort of yellow fever (YF)-17DD vaccine recipients from September 2005 to March 2007 in Recife, Brazil (de Melo, et al., *Am J Trop Med Hyg.*, 2011, 85:739-47). Longitudinal samples were collected before and after vaccination (30 to 90 days after vaccination). YFV-specific IgG in the samples was confirmed using virus particle-specific ELISA described elsewhere. Id. All samples tested were collected from individuals naïve to DENV as confirmed by anti-dengue virus-specific IgG ELISA. Id. WNV immune sera were collected from polymerase chain reaction (PCR)-confirmed cases in Idaho, USA, and kindly provided by Dr. William H. Hildebrand (Department of Microbiology and Immunology, University of Oklahoma Health Sciences Center, Oklahoma City, Okla., United States of America) (Kaabinejadian, et al., *PLoS One*, 2013, 8:e66298). Japanese Encephalitis immune pooled serum was obtained commercially from Japanese Encephalitis virus (JEV) vaccine recipients (NIBSC, UK).

All YFV-specific IgG samples collected after vaccination were pooled, as were the WNV and JEV immune sera, respectively, and used to evaluate the specificity of the anti-dengue NS1 total IgG ELISA.

Dengue clinical cohort. Longitudinal serum samples from virologically- and/or serologically-confirmed dengue cases used in this study were obtained from a well-characterized hospital-based cohort of confirmed DENV3 cases in Recife, Northeast Brazil (Cordeiro, et al., *Am J Trop Med Hyg.*, 2007, 77:1128-34). Dengue diagnosis included reverse transcription PCR (RT-PCR) to detect virus RNA as well as virus isolation in C6/36 mosquito cell lines, which were carried out on acute samples collected at patient hospital admission. Detection of virus-specific IgM and IgG antibodies were performed using commercial ELISA kits in order to determine type of infection (primary or secondary) (Cordeiro, et al., *PLoS One*, 2009, 4:e4945). The time points assigned for each sample were determined based on the number of days after onset of symptoms reported by the patients at admission.

Dengue cases were clinically classified into DF and DHF according to the World Health Organization (WHO) criteria from 1997 (World Health Organization, 1997. Dengue hemorrhagic fever: diagnosis, treatment, prevention and control. Second edition. World Health Organization, Geneva, Switzerland., available at: www.who.int/csdresources/publications/dengue/Denguepublication/en/ (accessed Feb. 5, 2018)). Dengue fever (DF) cases were characterized by fever lasting up to 7 days and accompanied by at least two of the following symptoms: headache, retro-orbital pain, myalgia, arthralgia, and rash associated with a platelet level above 100,000/mm$^3$. Dengue hemorrhagic fever (DHF) cases were defined as having the same clinical manifestations as those in DF, but with evidence of hemorrhage, thrombocytopenia (platelet<100,000/mm$^3$), and plasma leakage following defervescence. Dengue cases presenting thrombocytopenia but did not fulfill the requirements for DHF were classified as complicated dengue fever (DFC).

Detection of anti-dengue NS1-specific antibodies by enzyme-linked immunosorbent assay (ELISA). DENV NS1 protein from all four DENV serotypes (pooled at equimolar ratios) were used to coat high binding, half area 96-well polystyrene plates (Corning, N.Y., USA) overnight at 4° C. in carbonate/bicarbonate buffer (Thermo Scientific, Rockford, USA). The plates were blocked with skimmed milk (Bio-Rad, Hercules, USA) at 5% (w/v) in phosphate buffered saline+0.1% (v/v) TWEEN®20 (PBS-T) for 15 minutes at room temperature (18° C. to 23° C.). To determine the overall NS1-specific antibody responses following DENV infection, serum samples were added to the plates at a single dilution (1:50) and incubated at room temperature for 1 hour. Plates were washed five times with PBS-T and incubated for 1 hour at room temperature with horseradish peroxidase (HRP)-linked antibody anti-human total IgG (Jackson Immunoresearch, West Grove, USA), IgG2 (Invitrogen, Eugene USA), IgG3 (Invitrogen, Eugene, USA), IgG4 (Invitrogen, Eugene, USA), IgA (SeraCare, Milford, USA) or IgM (SeraCare, Milford, USA). After five washes with PBS-T, the plates were then incubated at room temperature for 30 minutes with SureBlue Reserve TMB Microwell Peroxidase substrate (SeraCare, Milford, USA) and the reaction stopped with 1N hydrochloric acid (Sigma, Saint Louis, USA). Optical densities at wavelength of 450 nm (OD450 nm) were determined using SpectraMax Plus PC380 microplate spectrophotometer using SoftMax Pro software version 6.4 (Molecular Devices, Sunnyvale, USA). The optical density from a blank sample was subtracted from all measurements before analysis.

Anti-dengue NS1-specific antibody endpoint titers (highest sample dilution that gives a signal above the assay cut-off) were further determined for IgG and IgG3 in three-fold serially diluted samples starting from the 1:50 dilution. Negative and positive control serum samples were included in each plate for cut-off values calculation and assay quality control, respectively. Endpoint antibody titers were calculated using 4-parameter non-linear regression built into the SoftMax Pro software.

Statistical analysis. Association analysis between detectable NS1-specific IgG/IgG3 titers and type of infection or clinical outcome was performed using exact Fisher's t-test. Four-parameter curve fitting was used to evaluate the upper asymptote, lower asymptote and slope of total IgG and IgG3 curves. All analyses described were performed using Prism version 7.02 statistical package (Graphpad, La Jolla, USA). Percent coefficient of variation (% CV) was calculated by dividing the standard deviation by the average of the curve parameter of each individual curve.

The mean duration of recent infection (MDRI) and False-Recent Rate (FRR) for various recency discrimination thresholds in IgG3 signal (MDIG3) were estimated, with recent infection defined as positive signal (e.g., anti-dengue NS1-specific IgG3 titer greater than a chosen threshold). Results on titer >1:100 were reported. MDRI was estimated using binomial logistic regression, e.g., fitting a model for the probability of obtaining the recent infection biomarker as a function of time since febrile illness onset. The MDRI is the integral of this function from zero to a chosen cutoff time (in this case, one year) beyond which recent results are defined as falsely recent. Confidence intervals for MDRI were obtained by 10,000 iterations of subject-level bootstrap resampling and computing the $2.5^{th}$ and $97.5^{th}$ percentiles of the MDRI estimates obtained on the resampled datasets. False-Recent Rate is simply the proportion of subjects that produce a recent result at time-points more than 1 year after onset of symptoms, with confidence intervals derived from an exact binomial test. These methods have been previously described (Kassanjee, et al., *Epidemiology*, 2012, 23:721-8; Kassanjee, et al., AIDS, 2014, 28:2439-49), and the calculations were conducted using the R package inctools, available from cran.r-project.org/web/packages/inctools/.

Results

Demographics of study participants. The longitudinal samples already available for use in this study were collected from 266 participants of a well-characterized cohort with confirmed DENV3 infection (Cordeiro, et al., *Am J Trop Med Hyg.*, 2007, 77:1128-34), and included children (36%) and adults (64%); the majority in both age groups had secondary dengue infections (72.2%) with DF or complicated dengue fever (DFC; Table 1). Individuals with DHF corresponded to a minor fraction of the population under study (1.9% and 3.8% of primary and secondary dengue infections, respectively; Table 1) limiting any possible evaluation of the relationship between clinical outcome and antibody responses to DENV NS1.

Pre-screening of different antibody types specific to DENV NS1. Antibody responses against DENV NS1 following dengue infection were investigated by testing for the presence of anti-dengue NS1-specific IgA, IgM, IgG2, IgG3, IgG4 antibodies at a single sample dilution (1:50) during the course of dengue infection and over one year after onset of symptoms. Reponses among individuals with primary or secondary dengue infections were compared. Nearly 600 samples were used in this analysis. Anti-dengue NS1-specific IgA, IgM and IgG antibodies were detected at different stages of infection and exhibited distinct kinetics following DENV infection. Overall, the antibody response kinetics were determined by number of previous DENV infections, as secondary infections had accelerated onset of and higher antibody levels compared with primary infections. Anti-dengue NS1-specific IgA was detected on the first day after onset of symptoms and remained high for over 6 months. Anti-dengue NS1-specific IgM exhibited a similar profile to IgA, although secondary infections were characterized by lower IgM levels compared with primary DENV infections.

Anti-dengue NS1-specific IgG2 and IgG4 were characterized by low levels that peaked over two months after onset of symptoms. Anti-dengue NS1-specific IgG3 was detected within the first week, peaked at 2-3 weeks and the levels decayed over three months after onset of symptoms.

Figure 1B:
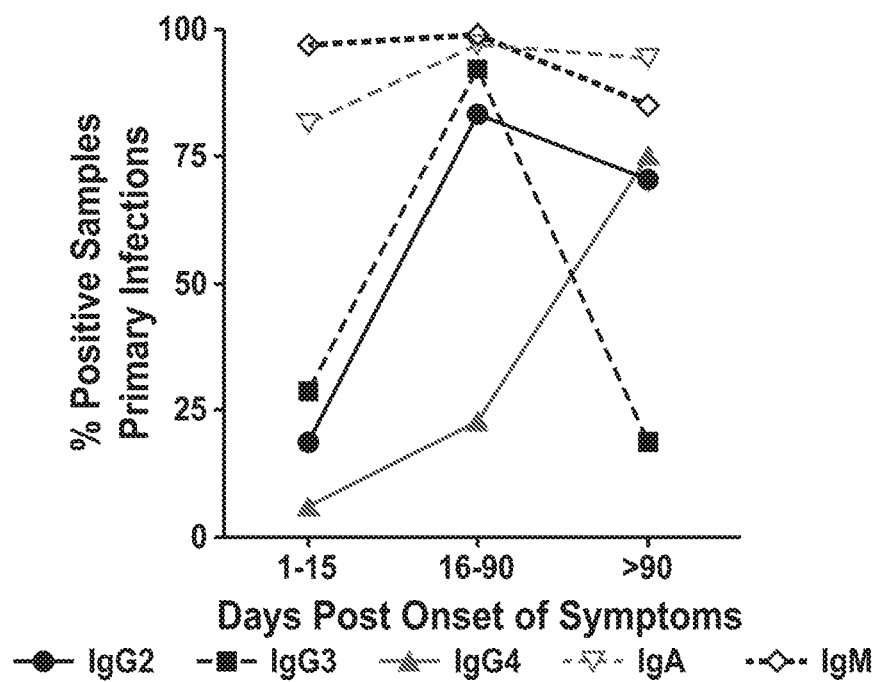
Figure 1C:
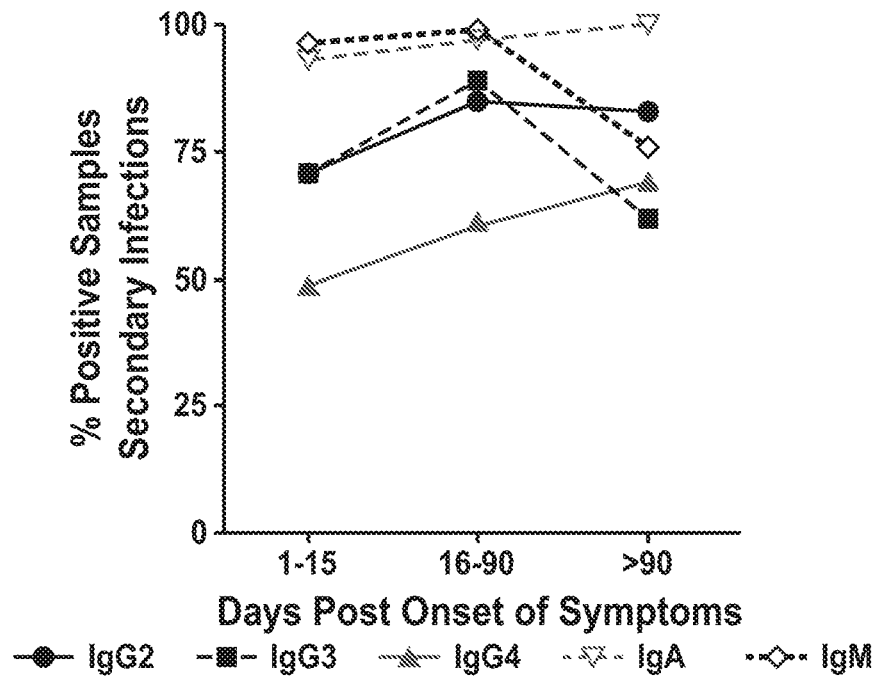

FIG. 1 depicts the number and percentage of samples, respectively, positive for each antibody analyzed at three different time points representing the acute phase (below 15 days), convalescence (16-90 days) and baseline after recovery (over 90 days). The percentage of samples positive for anti-dengue NS1-specific IgA and IgM was over 70% throughout the course of infection, regardless of the number of previous DENV infections. The anti-dengue NS1-specific IgG2 detection rate peaked at 16-90 days and remained high for over 90 days in both primary and secondary DENV infections (FIG. 1). In contrast, the anti-dengue NS1-specific IgG4 detection rate gradually increased peaking at over 90 days in samples from both primary and secondary infections (FIG. 1). The percentage of samples positive for anti-dengue NS1-specific IgG3 peaked at 16-90 days (over 75%) and, unlike anti-dengue NS1-specific IgA and IgM, dropped to undetectable levels in most of samples obtained later than 90 days after onset of symptoms. Thus, due to its short transient circulation, anti-dengue NS1-specific IgG3 can be a useful marker of recent DENV infection.

Figure 2A:
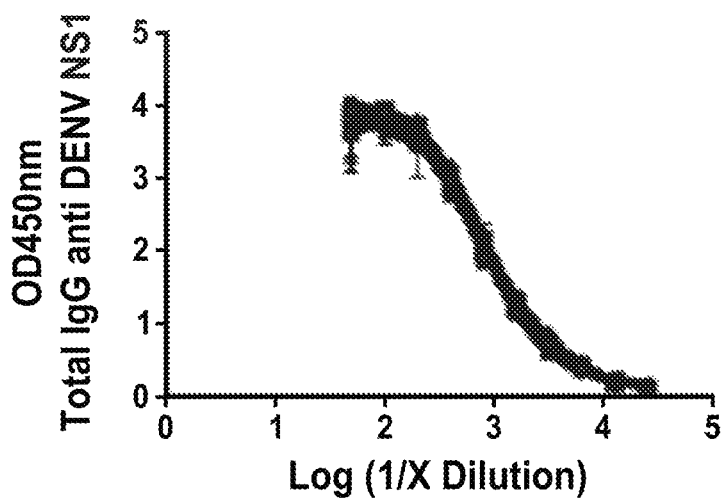
FIG. 2(A-E) shows anti-dengue NS1 total IgG and IgG3 immunoassay performances. Pooled immunoglobulins for intravenous injection purified from healthy donors from dengue endemic areas and pooled sera from recent virus exposures were serial diluted and used as positive controls in the anti-dengue NS1 total IgG (FIG. 2A) and IgG3 (FIG. 2B) immunoassays, respectively, on multiple days. Coefficient of variances were calculated (CV) on the upper and lower asymptote as well as $EC_{50}$ and slope (FIG. 2C). Serum samples from recent and from remote dengue infections as well as pooled sera from yellow fever vaccine recipients, Japanese encephalitis vaccine recipients and West Nile virus immune individuals, respectively, were tested in the anti-dengue NS1 total IgG (FIG. 2D) and IgG3 (FIG. 2E) immunoassays.
Figure 2E:
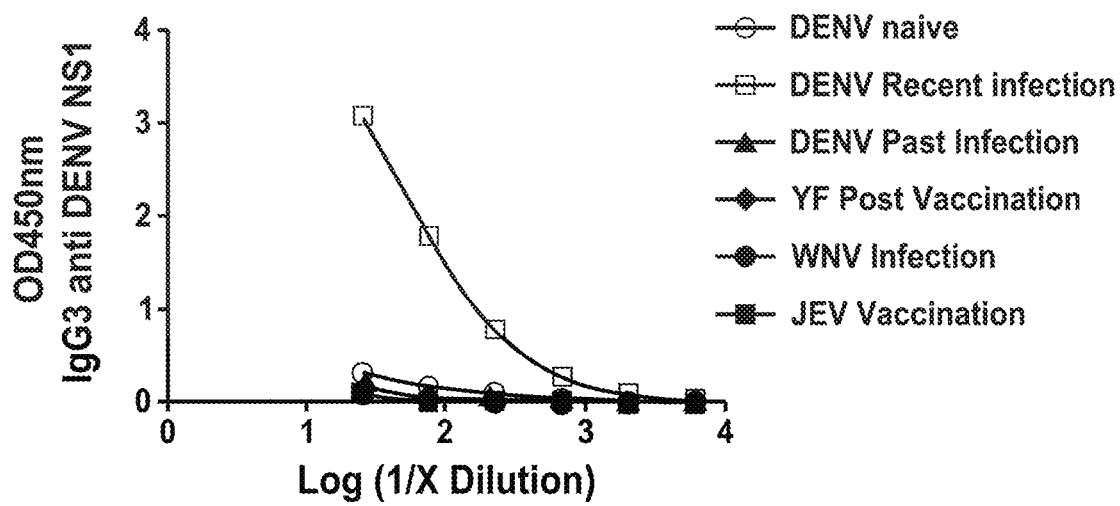
Figure 4A:
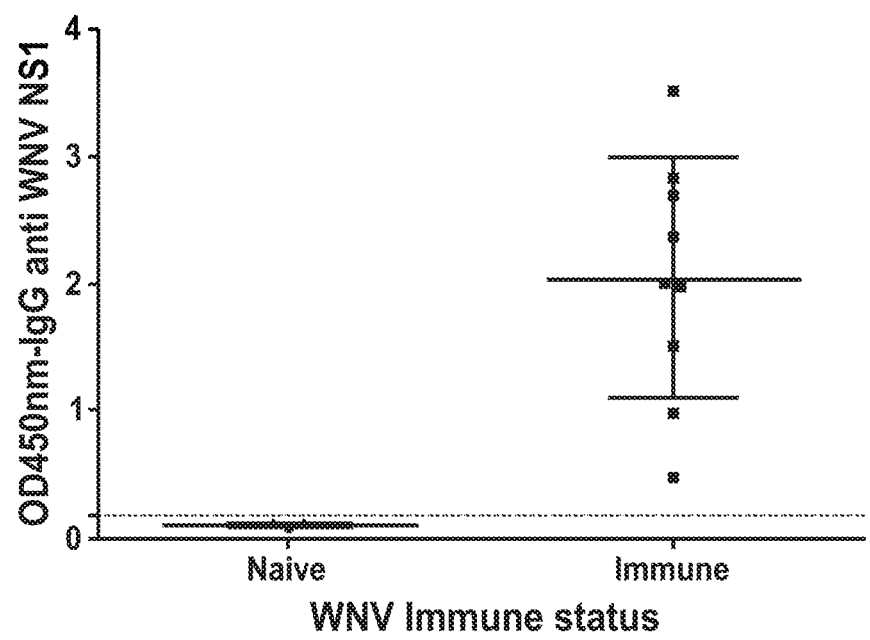
FIG. 4A shows naïve and convalescent samples collected up to one year after WNV infection evaluated for presence of WNV NS1-specific IgG. Error bars represents mean and standard deviation.
Figure 4B:
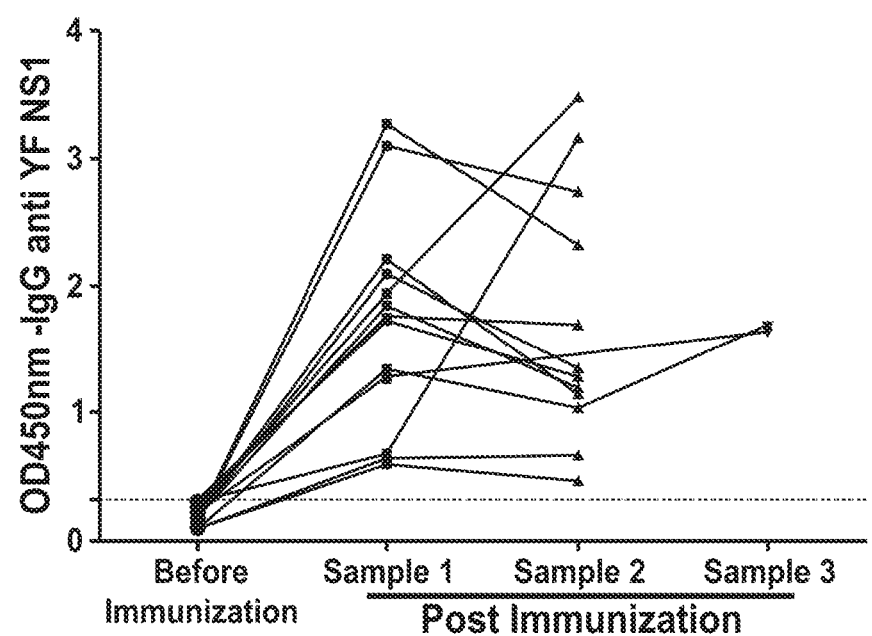
FIG. 4B shows samples collected from dengue naïve individuals from Brazil, before and after YF vaccination (from 30 to 90 days after immunization) evaluated for YF NS1-specific IgG.

Endpoint titers of anti-dengue NS1-specific IgG and IgG3. The endpoint titers of the anti-dengue NS1-specific IgG and IgG3 semi-quantitative immunoassays were evaluated in 916 longitudinal samples from 266 confirmed dengue cases. Titration curves with IVIg (n=104 individual curves) or pooled samples from recent infections (n=17 individual curves)] were used to evaluate data reproducibility of IgG and IgG3 immunoassays. Coefficients of variance (% CV) of the four data fitting parameters (upper and lower asymptote, slope and $EC_{50}$) of all curves evaluated suggest both immunoassays have good reproducibility (FIG. 2A-2C). Moreover, anti-NS1 antibodies present in hyperimmune pooled sera to other flaviviruses (following YF and JE vaccination or WNV infection; FIG. 4) did not cross-react with DENV NS1 in both immunoassays (FIG. 2D-2E).

Table 2 shows the number of individuals with either primary or secondary DENV infections with detectable anti-dengue NS1-specific IgG and IgG3 with both immunoassays. Participants with at least one sample collected between 10 and 90 days after the onset of symptoms were considered in this analysis. All confirmed dengue cases had detectable (titer >1:50) anti-dengue NS1 total IgG in at least one sample evaluated (Table 2), except for one sample from a child. Anti-dengue NS1-specific IgG3 was more likely to be detected (titer >1:50) in samples from primary (87.9%) than secondary (74.5%) DENV infections (Odds Ratio=3.8; 95% CI=1.1 to 12.2; p=0.025 Exact Fisher test) when both adults and children were analyzed together. Such an association was not evident when both age groups were analyzed separately (Table 2). No significant association between detectable titers and disease severity was observed in similar analyses performed comparing mild (DF) and severe (DFC+DHF) cases (Table 3).

Figure 3A:
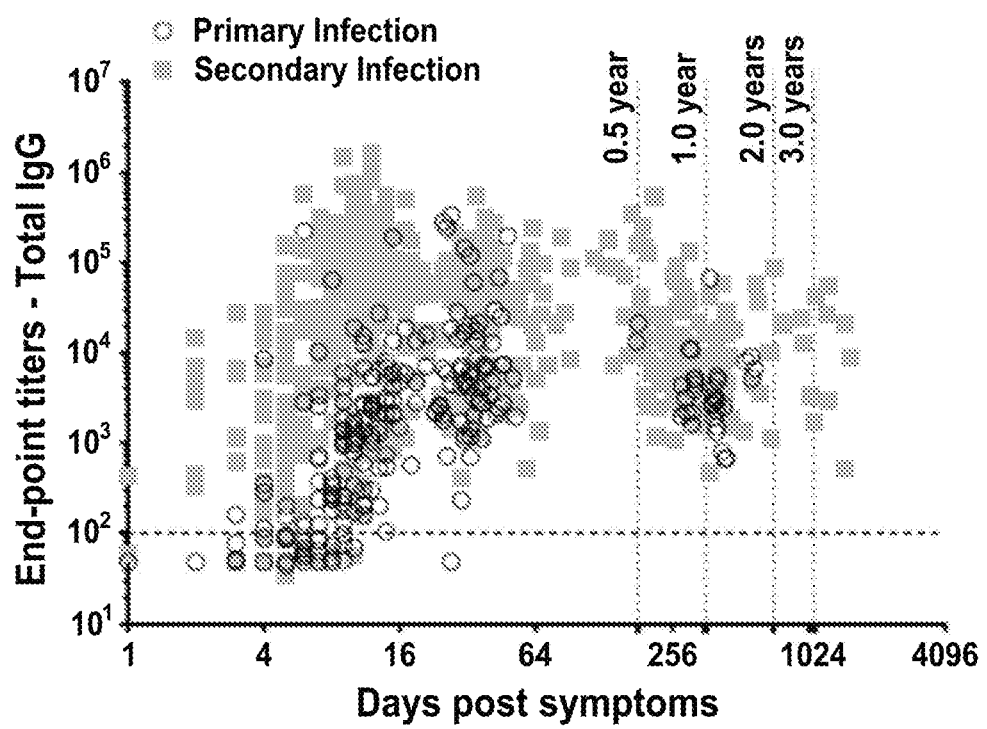
FIG. 3A shows the detection of anti-dengue NS1 total IgG in primary or secondary dengue infections.
Figure 3B:
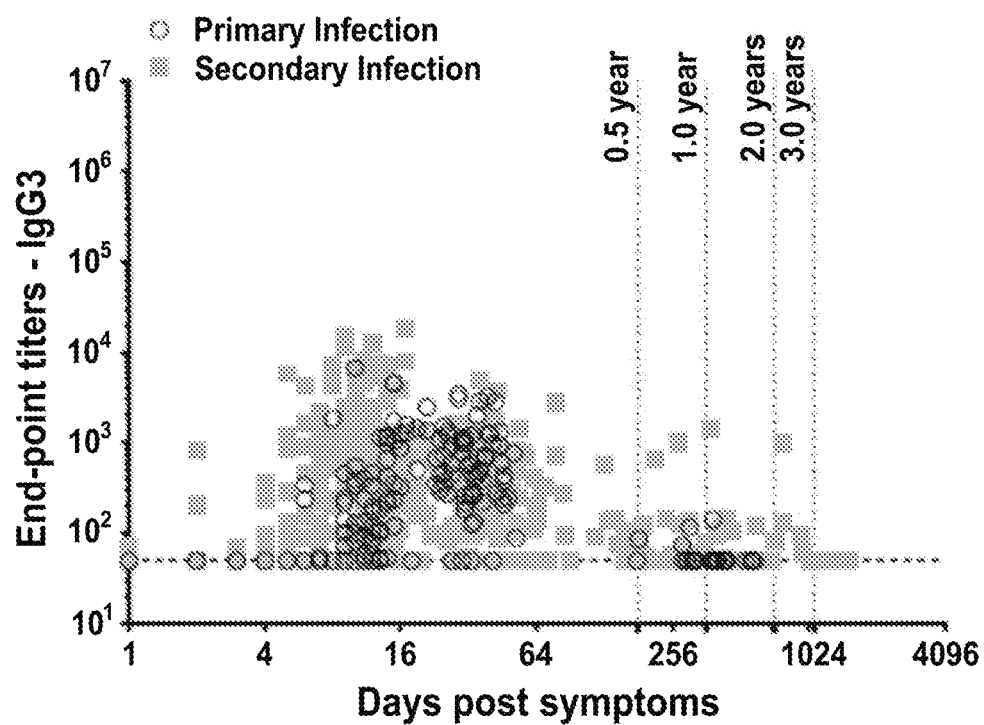
FIG. 3B shows the detection of anti-dengue NS1 total IgG in samples from individuals developing different clinical outcomes (DF, DFC or DHF).

Anti-dengue NS1-specific IgG and IgG3 were detected at earlier time points and reached higher peak levels in secondary DENV infections than primary (FIG. 3). The average duration of positive anti-dengue NS1-specific IgG3 signal (MDIG3), at a titer threshold of 1:100 calculated using all the IgG3 titration data (primary and secondary DENV infections; children and adults), was 149 days (MDRI, 95% CI: 126-172) and had an estimated probability of generating a false recent signal after 1 year of 0% (FRR, 95% CI 0 to 5.2%). Anti-dengue NS1-specific IgG3 titers dropped to low levels or was undetectable 4-6 months from onset of symptoms for most samples (FIG. 3A). However, anti-dengue NS1-specific IgG remained detectable for over 3 years after onset of symptoms (FIG. 3B). The anti-dengue NS1-specific IgG and IgG3 kinetics appeared similar across the different clinical outcomes evaluated, although the limited number of available samples from DHF participants did not allow a more in-depth analysis in this group (data not shown).

Example 2: Anti-Dengue NS1 IgG ELISA that can Discriminate Between Prior Dengue Infection from Vaccination with a Tetravalent Dengue Vaccine Summary Dengue virus infection elicits immune responses to multiple viral antigens including antibodies to dengue non-structural protein 1 (NS1) which are rapidly induced and detected within days of infection. The recombinant, live, attenuated, tetravalent dengue vaccine (CYD-TDV; Sanofi Pasteur) uses the yellow fever vaccine virus as a back-bone but expresses dengue virus premembrane and envelop proteins. Since CYD-TDV does not express dengue NS1, the utility of dengue NS1-specific IgG antibodies as biomarkers of dengue exposure in CYD-TDV recipients and controls was evaluated. A quantitative anti-dengue NS1 IgG enzyme-linked immunosorbent assay (ELISA) was optimized and evaluated. Parameters assessed included: accuracy, dilutability/linearity, precision, limit of quantitation and specificity. The assay specificity was further evaluated using Japanese Encephalitis virus, West Nile virus, Yellow Fever virus or Zika virus positive sera samples collected following confirmed infection or vaccination. Receiver operating-characteristics (ROC) curves, as well as sensitivity and specificity for discriminating previous dengue exposure, were assessed using 1,250 reference samples. Overall, the anti-dengue NS1 IgG ELISA discriminated previous dengue exposure from non-exposure before vaccination with CYD-TDV (ROC area under the curve>0.9). Assessment of paired samples from 2,511 vaccinated participants showed high overall agreement (93%) between pre-vaccination and post-vaccination dengue serostatus classification based on the anti-dengue NS1 IgG ELISA. However, misclassification of dengue serostatus was observed after vaccination likely due to a combination of asymptomatic dengue infections, assay variability and a moderate effect of CYD-TDV on the anti-dengue NS1 IgG ELISA readout.

Materials and Methods

Abbreviations: CYD-TDV, recombinant, live, attenuated, tetravalent dengue vaccine; IgG, immunoglobulin G; NS1, dengue non-structural protein 1; EC50, half maximal effective concentration; ELISA, enzyme-linked immunosorbent assay; GMC, geometric mean concentration; IQC, internal quality control; IVIG, reference generated using purified immunoglobulin; JEV, Japanese encephalitis virus; LLOQ, lower limit of quantitation; PRNT, plaque reduction neutralization test; ROC, receiver operating characteristic; TBEV, tick-borne encephalitis virus; USUV, Usutu virus; WNV, West Nile virus; ZIKV, Zika virus.

Recombinant proteins. Recombinant NS1 proteins from the following flaviviruses were obtained commercially (Native Antigen Company, Oxfordshire, UK): dengue virus (DENV) serotypes 1, 2, 3 and 4, yellow fever virus (YFV), Japanese encephalitis virus (JEV), tick-borne encephalitis virus (TBEV), West Nile virus (WNV), Zika virus (ZIKV), Usutu virus (USUV).

Unrelated proteins. Pertussis toxin (Marcy L'Etoile, France), tetanus toxoid (Toronto, Canada) and diphtheria toxoid (Swiftwater, USA) were manufactured by Sanofi Pasteur and used for antigen competition analysis.

Reference standard, internal quality controls and sample panel. The assay reference was generated using purified immunoglobulin (referred as IVIG) prepared in 2011 from pooled plasma from thousands of healthy participants in Brazil with confirmed reactivity to all 4 Dengue serotypes by PRNT. The lyophilized material was reconstituted at 50 mg/mL in IgG depleted human serum (Molecular Innovation, Novi, USA) determined to be negative for dengue NS1-specific IgG.

Samples from dengue seropositive individuals living in endemic areas in South America were obtained commercially (SeraCare, Milford, USA) and characterized for Dengue NS1 specific IgG levels over the quantitative range of the assay. Samples from dengue seronegative individuals living in the USA were obtained commercially (Keystone Biologicals, Hatboro, USA) and characterized by values near the limit of detection of the assay. All these samples were used as internal quality controls (IQC) in the development and characterization of the ELISA. Additional sample panels used for further assay characterization were prepared using commercially available serum with known dengue serostatus (SeraCare, Milford, USA).

Anti-Dengue NS1 IgG ELISA. BioOne Microlon (Greiner, Frickenhausen, Germany) flat bottom 96-well microtiter plates were coated with pooled DENV NS1, from all 4 serotypes at equimolar concentration, at 0.75 µg/mL in carbonate/bicarbonate buffer pH 9.6±0.1 overnight at 4° C. Coated plates were washed with 0.01M phosphate buffered saline+0.05% TWEEN®20 (PBS-T; Hyclone, Logan, USA) and blocked with PBS-T supplemented with 1% (v/v) goat normal serum (1% GNS; Gibco, Gaithersburg, USA) for 45±5 minutes at 21° C. The plates were washed again with PBS-T, then 2-fold serially-diluted human samples and IQCs in 1% GNS were added and incubated for 60±5 minutes at 37° C. Plates were washed a third time with PBS-T and incubated with peroxidase-conjugated F(ab')2 goat anti-human IgG, Fcγ Fragment (Jackson ImmunoResearch, West Grove, USA) in 1% GNS for 60±5 minutes at 37° C. The plates were washed again for the fourth time with PBS-T and color was developed with SureBlue Reserve TMB Microwell Peroxidase Substrate (SeraCare, Milford, USA) for 30±2 minutes at 21° C. The reaction was stopped with 1N HCl (Fisher Scientific, Fair Lawn, USA) and optical density at 450 nm (650 nm as the reference wavelength) measured using a SpectraMax Plus 384 Microplate reader (Molecular Devices, Sunnyvale, USA) in conjunction with SoftMax Pro software version 6.5.1 (Molecular Devices, Sunnyvale, USA). The concentration of anti-dengue NS1 IgG in the serum samples was determined in relation to the reference standards using a 4-parameter logistic (4PL) model built into the SoftMax Pro Software. Concentrations were reported in ELISA Units per milliliter (EU/mL).

Assay performance evaluation parameters. Assay qualification was carried out based on the ICH Harmonized Tripartite Guideline (ICH Harmonized Tripartite Guideline, 2005, Validation of analytical procedures: text and methodology Q2 (R1), available at: www.ich.org/fileadmin/Public_Web_Site/ICH_Products/Guidelines/Quality/Q2_R1/Step4/Q2_R1_Guideline.pdf (accessed Jan. 25, 2018) and included analytical specificity, matrix effect, accuracy, lower limit of quantitation (LLOQ), precision and linearity/dilutability as described below.

Matrix effect, analytical specificity, accuracy and linearity or dilutability. Accuracy, specificity in various serum matrices and linearity or dilutability of the assay were assessed based on spike recovery of characterized dengue IgG positive samples into hemolytic (Rockland, Limerick, USA), lipidic (Calbiochem, Temecula, USA), icteric (Calbiochem, Temecula, USA) or dengue negative serum samples (Keystone Biologicals, Hatboro, USA). For accuracy and matrix effects, the percentage recovery was calculated as (Observed Result÷Expected Result)×100%. Linearity was calculated by plotting the Expected Result as the independent variable (X-axis) and the Observed Result as the dependent variable (Y-axis) and fitting a linear regression. The slope and coefficient of correlation ($R^2$) for the linear regression was used to evaluate dilutability and linearity.

Precision. Assay precision was assessed using a panel of 120 samples with concentrations spanning a wide range (high, mid, low, negative and within 3×LLOQ) by multiple analysts to generate replicate results within runs (for intra-assay precision or repeatability) as well as across runs (for intermediate precision). Both repeatability and intermediate precision are assessed with the geometric coefficient of variation (GCV) expressed as a percentage, % GCV.

LLOQ establishment and verification. The minimum concentration at which samples yielded determinations with suitable precision and accuracy was established as the LLOQ. The established LLOQ was challenged and verified using a sample panel with concentrations near the LLOQ of the assay.

Analytical specificity (antigen competition). Competition studies were performed using homologous and heterologous competitors with samples containing a wide range of dengue NS1-specific IgG concentrations. Specificity was assessed in two parameters, percent competition and fold-difference between homologous and heterologous concentrations at which 50% competition was achieved (EC50). Percent competition was calculated as [1−(Signal or Optical Density of the Competed Sample÷Signal or Optical Density of the Uncompeted Sample)]×100%. For EC50 concentration estimates, homologous and heterologous percent competitions calculated (dependent variable, Y-axis) at each competitor concentration tested (independent variable, X-axis) were plotted. Linear regression fit was used in the portion of the curve crossing the 50% competition threshold and EC50 calculated using the linear regression equation. The fold difference between the homologous and heterologous competitors was calculated as Heterologous Competitor EC50÷Homologous Competitor EC50.

*Flavivirus* pre-immune sera. Dengue and Zika antibody-positive serum samples were obtained from individuals with virologically-confirmed dengue (VCD) or Zika infection in clinical trials with CYD-TDV, and JEV antibody-positive serum samples from participants demonstrated to be JEV PRNT positive. Additional JEV samples for specificity assessment were obtained from participants immunized with the live-attenuated SA14-14-2 JE vaccine in Sanofi Pasteur sponsored clinical trials. All samples were obtained in compliance with the original clinical protocols and consent for use of serum collected. The testing laboratory was blinded to any previous dengue serostatus as well as treatment group (vaccine or control).

Yellow fever—antibody positive human serum samples were obtained from healthy adult donors who received YFV vaccine (YF-VAX™). West Nile antibody-positive samples were purchased from SeraCare® (Milford, USA) and Discovery Life Science Inc (Los Osos, USA). Dengue antibody-negative human serum samples were obtained from healthy participants of Sanofi Pasteur sponsored studies from non-endemic dengue areas (USA).

Initial assay characterization for clinical evaluation of previous dengue exposure. To evaluate the performance of the anti-dengue NS1 IgG ELISA for ascertaining dengue exposure in clinical samples, the assay was characterized using 1250 samples from CYD-TDV clinical trials which were split into five distinct groups. Groups 1 and 2 served as reference dengue unexposed, while groups 3, 4 and 5 served as reference dengue exposed. Group 1 comprised samples from dengue unexposed participants from the USA (non-endemic region), minimizing the probability of previous exposure to dengue virus. These samples were also selected based on confirmed negative dengue PRNT50 titers (Timiryasova et al., *Am J Trop Med Hyg.*, 2013, 88:962-70) at baseline (before vaccination). Group 2 comprised samples from clinical trials conducted in dengue endemic regions (Southeast Asia), that were confirmed negative by dengue PRNT50 titers at baseline, but previous exposure to dengue virus (symptomatic or asymptomatic) could not be ruled out. Group 3 were selected from dengue exposed participants in clinical trials conducted in dengue endemic regions (Southeast Asia) who were dengue seropositive as determined by PRNT50; however, exposure to dengue was not virologically-confirmed and the time since dengue exposure and the infecting serotype were not known. Group 4 was selected from participants in CYD-TDV clinical trials with a documented VCD infection by RT-PCR within 1-13 months of serum collection, and those who also had longitudinal samples available about 2-3 years later (3-4 years after VCD infection) were included in Group 5.

An additional evaluation was performed using samples from Groups 1 and 2 (reference dengue unexposed) to investigate the potential influence of CYD-TDV exposure on the post-vaccination anti-dengue NS1 IgG ELISA levels. This involved measuring pre- and post-vaccination geometric mean concentrations (GMCs) overall, and stratified according to *Flavivirus* background where the samples were obtained.

Assay characterization using samples from phase III efficacy studies. Extensive assessment of the anti-dengue NS1 IgG ELISA concordance/agreement with the dengue PRNT50 assay (historically used for classifying dengue serostatus) was performed on baseline (pre-vaccination samples). Further, because of the possibility of boosting of low-level cross-reactive anti-dengue NS1 antibody responses following immunization with CYD-TDV, detailed assessments of the possible influence of the vaccine on the assay measurements were also performed. These assessments were done by applying the assay to a large number of samples; approximately 8000 samples from the immunogenicity subsets, 4000 collected before exposure to CYD-TDV or control (referred to as baseline or M0) and 4000 collected after exposure to three injections of CYD-TDV or control (referred to as post-dose 3, PD3 or M13).

Statistical Analysis.

Establishment of assay reference and controls. The reciprocal of the geometric mean for the half maximal effective concentration (EC50) endpoint values of individual curves was assigned as reference concentration. The assay detection limit or limit of detection (LOD) was determined using the method of estimating Minimum Detectable Concentration (MDC) and Reliable Detection Limit (RDL) on the mean reference curves (O'Connel, et al., *Chemometr Intell Lab Syst.*, 1993, 20:97-114; Quinn et al., *Emerg Infect Dis.*, 2002, 8:1103-10). The acceptable limits were established based on ±two standard deviations (SD) from the average for control sera and ±three SD for the reference.

Evaluation of assay parameter performance. Intra-assay precision (or repeatability) and intermediate precision was evaluated by estimating the variance component in a mixed model. The accuracy and matrix were evaluated using percent recovery in a spike-recovery experiment using reference serum. Percent recovery was calculated as (Observed Result÷Expected Result)×100%. Linearity was evaluated by fitting the Expected Result as the independent variable (X-variable) against the Observed Result as the dependent variable (Y-variable) in a linear regression model. The LLOQ was established following the method described in EP-17 guidelines (National Committee for Clinical Laboratory Standards, Protocols for determination of limits of detection and limits of quantitation, approved guideline. NCCLS document EP17-A [ISBN 1-56238-551-8], NCCLS, 940 West Valley Road, Suite 1400, Wayne, Pa. 19087-1898 USA, 2004). The LLOQ was challenged and verified by evaluating the linearity and precision of the sample near the LLOQ level.

Receiver operating characteristic (ROC) curves and area under the curve (AUC). The Receiver operating characteristic curves or ROC curves were created by plotting the true seropositive rate defined as the rate of NS1 positive in group 3/4/5 samples against the false seropositive rate defined as NS1 positive in group 1/2 samples at various NS1 thresholds from 9 EU/mL to approximately 100 EU/mL. The area under the ROC was calculated as a single numerical measurement to describe the performance of the NS1 concentration as a biomarker for discriminating previous dengue exposure from non-exposure.

Other statistical methods for assay characterization. The performance characteristics of the assay at different thresholds were estimated based on rates of true or false classifications compared to the reference standards.

Concordance between the anti-dengue NS1 IgG ELISA serostatus classifications at a threshold of 9 EU/mL with the PRNT50 at baseline were evaluated by estimating the percent agreement and Cohen's kappa. Agreement between the methods was estimated as the proportion of all baseline samples that had the same dengue serostatus classification by both methods. The GMC was calculated for pre- and post-vaccinations samples in the vaccine and control groups, respectively. The GMC ratio was calculated as the ratio of post-vaccination to pre-vaccination GMCs in each group. To compare the changes in anti-dengue NS1 IgG values from paired prevaccination/injection to post-vaccination/injection samples between the vaccine and control groups, the difference in the log 10-transformed results were calculated and a Student's t-test was utilized to compare the difference between groups. A chi-square test was used to compare vaccine and control groups on the frequency of erroneously classifying month 0 (M0) dengue serostatus based on anti-dengue NS1 IgG level (with a threshold<9 EU/mL to define seronegative) when using month 13 (M13) sample measurements.

Results

Anti-dengue NS1 IgG ELISA design and establishment of assay reference and controls. The IVIG reference standard obtained from healthy individuals in Brazil prior to 2015 was reconstituted in human IgG-depleted serum. The reconstituted material demonstrated similar levels of reactivity to the recombinant NS1 proteins of each DENV serotype individually and when all four serotype-specific recombinant NS1 antigens were pooled (data not shown). The anti-dengue NS1 IgG level of the IVIG was established as 863.3 EU/mL based on the reciprocal of the EC50 endpoint ELISA values of 104 individual titration curves.

The IVIG reference standard was used to generate an 8-point assay reference curve comprising serial 2-fold dilutions in the range 4.31-0.03 EU/mL. Four parameter curve fitting analyses demonstrated that the upper and lower asymptote as well as slope of the curve were 3.834, 0.153 and 1.427, respectively (Table 4). In addition, the assay LOD was established as 2.33 EU/mL.

The concentration of the positive internal quality control (IQC) and test samples were calculated based on the mean of 5 dilutions minimum, with acceptable coefficient of variation (CV) of <20%. Acceptance ranges for individual IQCs were established over the range of the assay (high, intermediate, low and negative) based on multiple runs, analysts and days to capture the majority of the sources of assay variability (Table 5). The validity of results from each plate requires that reference curve parameters, blank background and IQCs for each plate to be within established ranges shown in Tables 4 and 5, respectively.

Evaluation of assay parameter performance. The accuracy of the assay was evaluated based on spiking studies using samples with established concentrations. Samples ranging 863.3-5.7 EU/mL were prepared in negative serum matrix and tested a minimum of 3-10 times by two analysts. Assay accuracy was 89-114% based on percentage recovery (Table 6).

LLOQ was characterized as 9 EU/mL based on EP-17 guidelines (National Committee for Clinical Laboratory Standards, 2004) and verified by calculating percentage recovery and intermediate precision of samples exhibiting dengue IgG NS1 levels of: <9 EU/mL, 9-30 EU/mL, 30-100 EU/mL and >100 EU/mL. The minimum concentration demonstrating percentage recovery between 80-120% and intermediate precision≤25% CV was 9.0 EU/mL (LLOQ; Table 7). For analysis purposes, samples with values<9 EU/mL were assigned a value of half the LLOQ (e.g., 4.5 EU/mL) to calculate the GMC.

Repeatability of the assay was analyzed using 120 samples, tested 3-5 times by two analysts in a single run, and positive samples were included in the statistical analysis. The estimated percentage CV for analyst 1 and 2 were 11.6 (95% confidence interval [CI]: 10.7, 12.5) and 12.2 (95% CI: 11.3, 13.2), respectively, and overall 11.9% (95% CI: 11.3, 12.6). Intermediate precision, evaluated using 120 samples tested 6-10 times by two analysts over 9 days, was 14.7% (95% CI: 13.9, 15.6).

Linearity and dilutability were evaluated by determining the concentration of anti-dengue NS1 IgG for 10 individual samples tested undiluted and a minimum of two additional dilutions. Linear regression analysis for each sample demonstrated slopes in the range 0.89-1.21 with $R^2 \geq 0.99$ (FIG. 10).

Potential interference from lipidic, icteric and hemolytic matrices in addition to unrelated antibodies was assessed to determine specificity. The assay reference was spiked into the four matrices prepared in anti-dengue NS1 IgG negative serum at five concentrations spanning the range of the assay. The samples were then tested with the ELISA and evaluated for percentage recovery. No significant interference with assay accuracy (percentage recovery 80-120%) was demonstrated with any of the matrices evaluated (data not shown).

Figure 5:
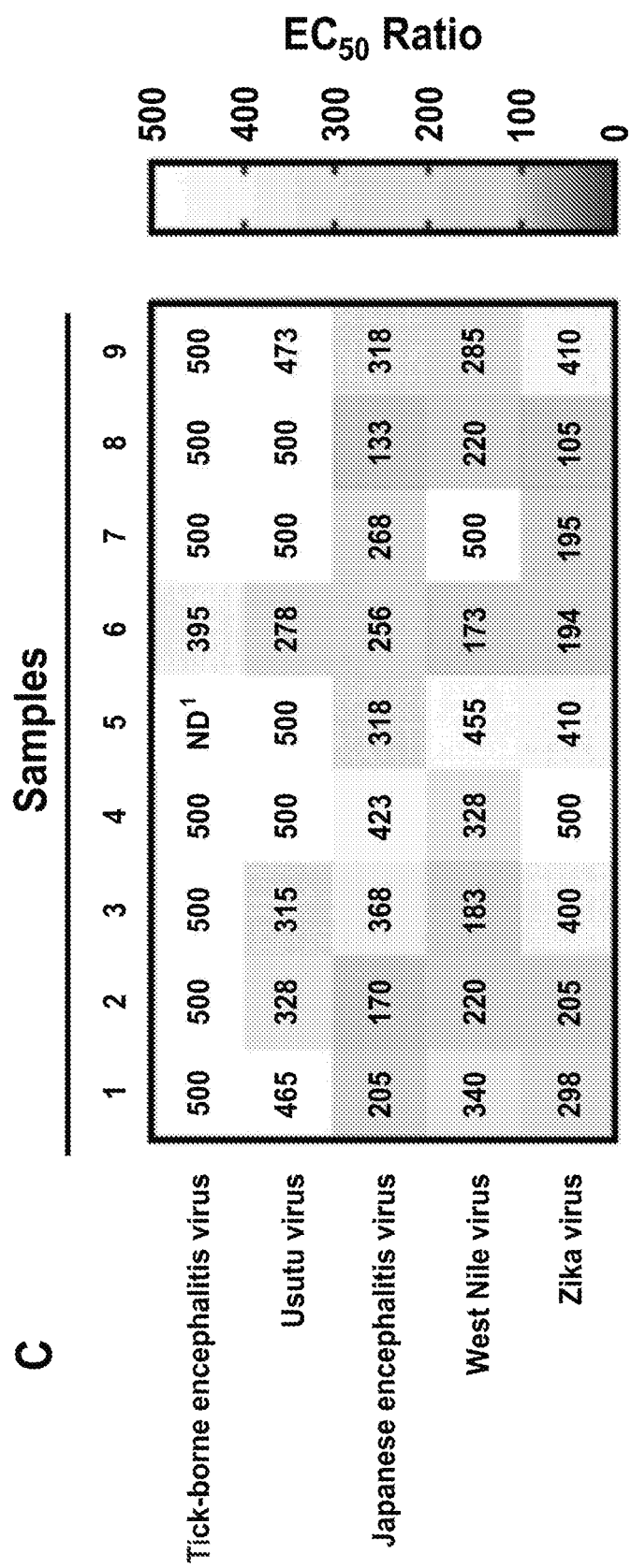
FIG. 5 shows heatmap graphic of heterologous and homologous competition of serum antibodies to unrelated or *Flavivirus* NS1 antigens. This figure shows the fold change difference between $EC_{50}$ ratios (heterologous flaviviruses/homologous Dengue) plotted as a heatmap graphic.

Antigen specificity was further evaluated using 10 representative anti-dengue NS1 IgG positive samples spiked with homologous and heterologous competitors. Competition with homologous dengue NS1 was consistently demonstrated (≥75% signal inhibition) in the ELISA for all samples tested. In contrast, unrelated antigen (pertussis toxin, tetanus toxoid and diphtheria toxoid) had little to no interference with the assay (<12% signal inhibition). For the heterologous NS1 antigens evaluated, the percent competition was >25% for 6-9 samples for ZIKV, JEV, WNV, USUV and TBEV, and no significant competition was observed for YFV NS1. Of note, the competitors were spiked at NS1 concentrations of about 20 µg/mL, while the detection antigen (pooled DENV serotypes 1-4) was 0.75 µg/mL, about 25-fold excess of competitor. Therefore, samples demonstrating competition≥25% were further evaluated by competing with titrating concentrations of homologous or heterologous *Flavivirus* NS1 antigens. The differences in relative ratio of the heterologous EC50/homologous EC50 (heterologous antigen EC50 effective concentration/homologous antigen EC50 effective concentration) were greater than 100-fold for all the heterologous competitors (FIG. 5).

Evaluation of assay specificity using other *Flavivirus* positive sera. The specificity of the assay was also assessed using samples with positive antibody titers to other flaviviruses: ZIKV, JEV, YFV and WNV. As shown in Table 8, the GMCs were 6.6, 4.7, 51.0 and 21.9 EU/mL for YFV, JEV, WNV and ZIKV positive samples, respectively.

Initial assay characterization for clinical evaluation of previous dengue exposure. The anti-dengue NS1 IgG ELISA was further evaluated for its intended use utilizing clinical samples divided into five distinct groups, used as reference for the classification of dengue exposure or not. Dengue-negative participants from non-endemic regions (PRNT negative, likely dengue unexposed) had GMC values below the LLOQ of 9 EU/mL (group 1, GMC 6.6 EU/mL [95% CI: 6.2, 7.0]) and similar to PRNT negative individuals in dengue endemic regions (group 2, GMC 7.8 EU/mL [95% CI: 6.8, 9.0 EU/mL]). Samples from participants with presumed prior exposure to dengue based solely on serology (PRNT positive, Group 3) had significantly greater anti-dengue NS1 IgG levels (GMC 74.4 EU/mL [95% CI, 59.8 to 92.6 EU/mL]). Samples obtained from VCD cases collected 1-13 months post-infection (recent infection) had markedly higher anti-dengue NS1 IgG levels (GMC 981.8 EU/mL [95% CI, 814.0, 950.3 EU/mL]). The anti-dengue NS1 IgG response remained high (GMC 770.9 EU/mL [95% CI, 625.4 to 950.3 EU/mL]) in VCD positive samples collected>3-4 years post infection (remote infection; group 5).

The ROC curve, which simultaneously present true positive rate (sensitivity) against false positive rate (1 minus specificity) at different thresholds was determined. The area under the ROC curve was >0.90 for data analysis encompassing the five reference groups, indicating that the anti-dengue NS1 IgG ELISA was capable of discriminating between samples that were dengue unexposed and exposed.

The rates of misclassification (false positives and false negatives) at different assay thresholds from 9-100 EU/mL were determined. At LLOQ threshold (here, 9.0 EU/mL), the false positive rate (misclassify unexposed samples as seropositive) was 31.4% and the false negative rate (misclassify exposed samples as seronegative) was 4.7%. This threshold minimizes the erroneous classification of samples from dengue exposed individuals as seronegative, but results in erroneous classification of samples from dengue unexposed individuals as seropositive. The false seropositive rate decreased to 9.3% and 2.5% at 20 EU/mL and 50 EU/mL thresholds, respectively, while the false seronegative rate increased to 6.8% and 12.1%, respectively.

Assay characterization using samples pre and post vaccination. Overall, there was high agreement observed (90.15%) in the dengue serostatus classification before vaccination between the PRNT and anti-dengue NS1 IgG ELISA, using the 9 EU/mL threshold for the latter, indicating that the assay may be a suitable alternative to dengue PRNT for assessing baseline dengue serostatus. Cohen's kappa coefficients indicated substantial agreement between the two classification methods (0.75 overall, 95% CI: 0.729, 0.776).

Table 9 shows the classification of serostatus by the anti-dengue NS1 ELISA applied to M13 samples in participants with paired M0 (baseline) and M13 (post-dose 3) samples for whom the M0 sample tested below the threshold of 9 EU/mL (e.g., seronegative by the NS1 assay at M0), and for whom the M0 sample tested equal or greater than 9 EU/ml (e.g., seropositive by NS1 assay at M0). Overall, there was high agreement between pre-vaccination/injection (M0) and post-vaccination/injection dengue serostatus classification (M13) by the NS1 assay for CYDTDV (92.8% agreement) and control (94.4% agreement) groups, indicating the value of the assay for assessment of previous dengue exposure even when applied post-vaccination. However, when using NS1 at M13, there is evidence of misclassification of baseline dengue NS1 seronegative participants as seropositive in both CYD-TDV and control groups. Furthermore, there is excess misclassification of seronegative participants (by M0 NS1<9 EU/mL) as seropositive (by M13 NS1≥9 EU/mL) in the CYD-TDV group compared to controls, although the magnitude of this excess misclassification is small (approximately 8%).

Example 3: ZIKV NS1 IgG3 Assay & DENV NS1 IgG3 Assay

Half of the area of 96-well polystyrene plates (Corning, USA) were coated with 50 µL per well of pooled DENV NS1 (Native Antigen, UK) at 2.27 µg/mL in carbonate/bicarbonate buffer (rows A through D) and the other half of the plate with 50 µL per well of ZIKV NS1 Native Antigen, UK) at 2.27 µg/mL in carbonate/bicarbonate buffer (rows E through H) and incubated overnight (16 hrs-18 hours) at 4° C. in a humid chamber. The plate was aspirated and 150 µL of skimmed milk (Bio-Rad, USA) were added per well at 5% (w/v) in PBS-T buffer [PBS with 0.1% (v/v) TWEEN®20; blocking/dilution buffer]. Plates were incubated for 15 minutes at room temperature (RT; 22° C.+2° C.). Plates were aspirated and, in duplicate, 50 µL of serum samples and assay controls [Zika positive control: serum from recent Zika infection collected 20-30 days post onset of symptoms); Dengue positive control: pooled sera from recent Dengue infection collected 20-30 days post onset of symptoms; Negative control: pooled sera from healthy individuals naïve to both Zika virus and Dengue virus)] diluted 1:50 in blocking/dilution buffer were added per well. Plates were incubated for 1 hr at RT. Plates were washed 5 times with 190 µL per well of washing buffer [PBS with 0.1% (v/v) TWEEN 20]. Plates were dried (by aspirating using a plate washer machine or by tapping in paper towel), and then 50 µL of Mouse anti human IgG3-HRP (Invitrogen, USA) at 1:600 were added per well. Plates were incubated for 1 hour at RT, then washed 5 times with 190 µL per well of washing buffer. Plates were dried and 50 µL of TMB (KPL, USA) were added per well. Plates were incubated for 30 minutes at RT, and the reaction was stopped with 50 µL per well of 1N HCl. Optical densities at wavelength of 450 nm ($OD_{450}$) were determined using SpectraMax Plus PC380 microplate spectrophotometer using the SoftMax Pro software version 6.4 (Molecular Devices). Plates were read within 20 minutes of stopping the reaction. All wells were subtracted by the average of the conjugate blanks. For Dengue IgG3 analysis, the DENV ratio was determined by dividing the OD450 nm of the samples by the average OD450 nm of the negative control. For ZIKV IgG3 analysis, the ZIKV ratio was determined by dividing the OD450 nm of the samples by the average OD450 nm of the Dengue recent infection. The cut-off values for the DENV IgG3 and ZIKV IgG3 ratios were 1.5 and 0.586 respectively. If a sample's average ratio was above the cut-off value, it was considered eligible for analysis only if the coefficient of variation [(Standard deviation of replicates/average of replicates)×100] of replicates was below 20%.

Total DENV NS1 IgG assay. High binding, half area 96-well polystyrene plates (Corning, USA) were coated overnight at 4° C. with DENV NS1 (pooled at equimolar ratio; Native Antigen, UK) at 1 µg/mL in carbonate/bicarbonate buffer (Pierce, Ill., USA). Plates were blocked with skimmed milk (Bio-Rad) at 5% (w/v) in PBS-T buffer [PBS with 0.1% (v/v) TWEEN®20; blocking buffer] for 15 minutes at room temperature (RT; 21° C. to 23° C.). To determine the NS1-specific antibody titers, serum samples were 3-fold serially diluted in blocking buffer (1:50-1:4050, 1:900-1:72900 or 1:8100-1:656100) for a total of 5-point dilutions and incubated for 1 hour at RT. On each plate, a negative and a positive control serum samples were included for calculation of cut-off values and for assay quality control respectively. Pooled human serum sample from the USA negative for IgG anti-DENV was used as a negative control, whereas a pooled sample from Brazil was used as a positive control at three different dilutions (high, medium and low controls). The negative control was confirmed for the absence of IgG anti-dengue antigens and, thus, considered a dengue naïve sample. Plates were washed 5 times with PBS-T and incubated for 1 hour at RT with horseradish peroxidase (HRP)-linked antibody anti-human IgG (Jackson Immunoresearch). After 5 washes with PBS-T, plates were incubated for 30 minutes at RT with TMB substrate (KPL, USA), and the reaction was stopped with 1 M hydrochloric acid (HCl; Sigma). Optical densities at wavelength of 450 nm (OD450) were determined using SpectraMax Plus PC380 microplate spectrophotometer using the SoftMax Pro software version 6.4 (Molecular Devices). The results from all wells were subtracted from the blank before analysis. Cut-off values were calculated as the mean OD of negative control plus 3 times the standard deviation. For NS1-specific IgG assay, negative control values ranged from 0.132 to 0.293 [mean/SD: 0.200/0.019 (n=75 plates)]. Positive control values for high, medium and low dilutions (n=75 plates) ranged from 1.334 to 2.705 [mean/SD: 1.846/0.228], 0.697 to 1.66 [mean/SD: 1.057/0.146] and 0.403 to 0.943 [mean/SD: 0.638/0.083]. Endpoint antibody titers were calculated using 4-parameter nonlinear regression on Prism version 6e (GraphPad Software Inc., La jolla, CA).

PRNT. ZIKV and DENV1-4 specific neutralizing antibodies were assessed by PRNT, following a modified protocol described in details elsewhere. PRNT was performed using virus strains isolated in Northeast Brazil: ZIKV (BR-PE243/2015), DENV-1 (BR-PE/97-42735), DENV-2 (BR-PE/95-3808), DENV-3 (BR-PE/02-95016), and DENV-4 (BR-PE/12-008). Serum samples were heat-inactivated (30 min at 56° C.) and serially diluted by 4-fold (starting at 1:20) with Minimal Essential Medium (MEM). Virus was then mixed with an equal volume of serum and incubated at 37° C. for 1 hr. The virus-serum mixture was inoculated onto Vero cell monolayers in 24-well plates (150,000 cells/well) and allowed to absorb for 1 hour at 37° C. prior to the addition of 500 μL of semi-solid medium (MEM10× containing 10% carboxymethylcellulose (3%), 10% fetal bovine serum, 1% penicillin/streptomycin and 1% amphotericin b). Following incubation (6 days, at 37° C.), cells were fixed with 1 mL of formalin solution (3.5 M), and then stained with crystal violet for visualization of plaques. The cut-off for PRNT positivity was defined based on a 50% reduction in plaque counts (PRNT50). ZIKV and DENV1-4 neutralizing antibody titers were estimated using a four-parameter non-linear regression. Serum samples were considered positive when antibody titers were >1:100 (log 2) for ZIKV and >1:20 against at least one DENV serotype.

Results

A factor limiting quantification of Zika seroconversion is the lack of serological tests that can measure antibody responses to Zika with high sensitivity and specificity. Many available assays are not specific between flaviviruses. Non-specificity is problematic when quantifying Zika transmission in populations that have been heavily exposed to other flaviviruses including dengue. Described here is an assay based on IgG3 responses to the NS1 antigen of ZIKV. This assay was validated using samples obtained before and after ZIKV introduction into the study population (FIG. 6), as well as samples from PCR-confirmed infections (data not shown). A subset of samples was also tested using a ZIKV plaque reduction neutralization assay.

Figure 6:
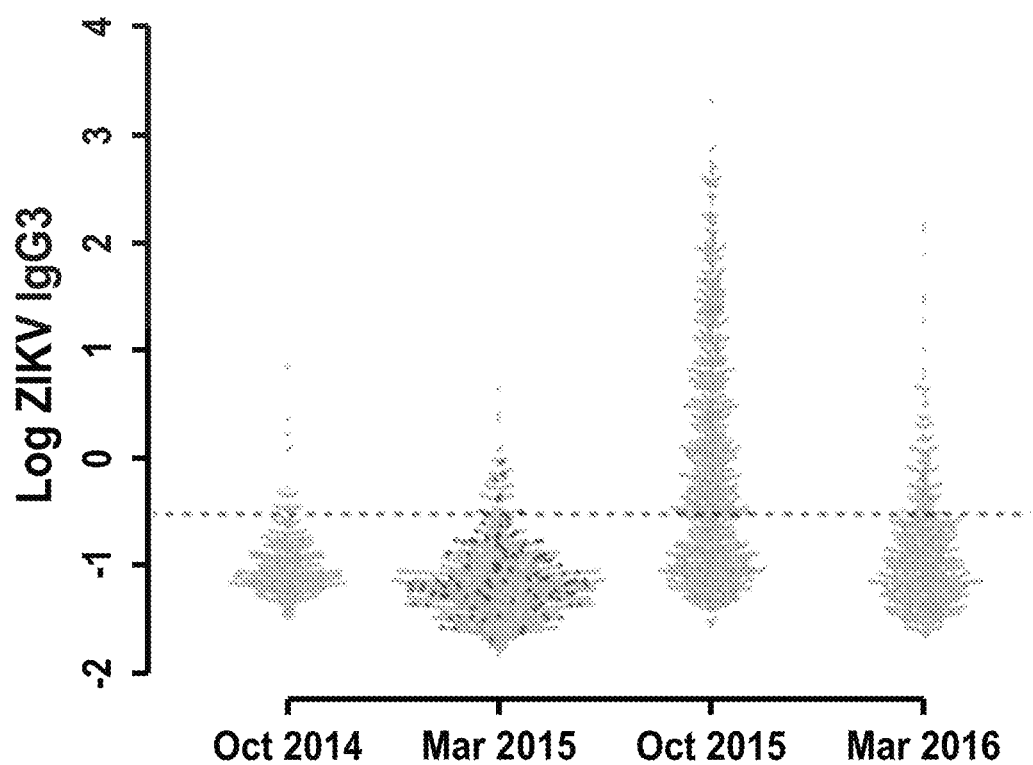
FIG. 6 shows the results of serological testing conducted around the time that the ZIKV outbreak took place in the tested population. Each dot shows the result of an individual sample using the ZIKV IgG3 assay. A subset of samples was also tested using a ZIKV plaque reduction neutralization assay. Dashed line indicates the cut-point established, using plaque reduction neutralization test (PRNT) results as the gold standard, to achieve a sensitivity of 85% and a specificity of 97%.

Multiple rounds of sampling occurred before and after the bulk of clinical Zika cases were detected in this community. FIG. 6 shows the timing of sampling performed in this cohort around the period of the Zika outbreak in this population. Samples collected in October 2014 and March 2015, before the ZIKV epidemic, were consistently negative for ZIKV NS1 IgG3 antibodies (7% seropositive 95% CI 6%-9%, n=988) in an IgG3 assay as well as by plaque reduction neutralization (1% 95% CI 0%-6%, n=101). In contrast, 60% (95% CI 57%-64%, n=716) of samples collected in October 2015 (5 months after the epidemic peaked) were positive, indicating infection of the majority of individuals in the cohort.

What is claimed is:

1. A method of measuring efficacy of a recently administered *Flavivirus* vaccine comprising:
   a) obtaining a biological sample from a subject administered the *Flavivirus* vaccine within a prior four months and wherein the subject had an onset of symptoms of a *Flavivirus* a infection greater than four months prior to the administration of the *Flavivirus* vaccine;
   b) contacting the biological sample with one or more *Flavivirus* NS1 polypeptides corresponding to the *Flavivirus* vaccine; and
   c) detecting an amount of anti-NS1 IgG3 in the biological sample;
wherein an increase in the amount of anti-NS1 IgG3 relative to a control indicates efficacy of the recently administered *Flavivirus* vaccine, wherein the control is obtained from a second subject or a population that had the *Flavivirus* infection and had not been recently vaccinated with the *Flavivirus* vaccine.

2. The method of claim 1, further comprising measuring an amount of anti-NS1 IgG1, anti-NS1 IgG2, anti-NS1 IgG4, anti-NS1 total IgG, and/or anti-NS1 IgM.

3. The method of claim 1, wherein the one or more NS1 polypeptides are selected from the group consisting of a Dengue 1 NS1, a Dengue 2 NS1, a Dengue 3 NS1, a Dengue 4 NS1, a Japanese Encephalitis virus NS1, a St. Louis Encephalitis virus NS1, a West Nile virus NS1, a Zika virus NS1, and a Yellow fever virus NS1.

4. The method of claim 1, wherein the *Flavivirus* vaccine is a Dengue virus vaccine and the one or more NS1 proteins are selected from the group consisting of a Dengue 1 NS1, a Dengue 2 NS1, a Dengue 3 NS1, and a Dengue 4 NS1.

5. The method of claim 1, wherein the *Flavivirus* vaccine is a Zika virus vaccine and the NS1 protein is a Zika virus NS1.

6. The method of claim 1, wherein the anti-NS1 IgG3 is detected in an immunoassay selected from the group consisting of enzyme linked immunosorbent assays (ELISAs), enzyme linked immunospot assays (ELIspot), radioimmunoassays (RIA), immunobead capture assays, Western blotting, dot blotting, gel-shift assays, intracellular cytokine stain, immunohistochemistry, protein arrays, and multiplexed bead arrays.

7. The method of claim 1, wherein the biological sample is whole blood, serum, peripheral blood mononuclear cells (PBMC), saliva, urine, oral secretions, amniotic fluid, plasma, bone marrow, or cerebrospinal fluid (CSF).

8. The method of claim 1, further comprising detecting an increase in an amount of anti-NS1 IgG1, anti-NS1 IgG2, or anti-NS1 IgG4 corresponding to the one or more flaviviruses as compared to a control.

9. The method of claim 1, further comprising detecting an increase in an amount of anti-NS1 total IgG corresponding to the one or more flaviviruses as compared to a control.

10. The method of claim 4, wherein the *Flavivirus* vaccine comprises one or more non-Dengue *Flavivirus* polypeptides.

11. The method of claim 10, wherein the *Flavivirus* vaccine comprises a yellow fever NS1 polypeptide and not a Dengue virus NS1 polypeptide.

12. The method of claim 1, wherein the biological sample is obtained within four months or less after the administration.

13. The method of claim 1, wherein the biological sample is obtained within two and four weeks after the administration.

14. The method of claim 1, wherein the biological sample is obtained within one and three weeks after the administration.

15. The method of claim 1, wherein the biological sample is obtained within three and five weeks after the administration.

16. The method of claim 1, wherein the biological sample is obtained within four and six weeks after the administration.

17. The method of claim 1, wherein the biological sample is obtained within one and three months after the administration.

18. The method of claim 1, wherein the biological sample is obtained within two and four months after the administration.

19. The method of claim 1, wherein the subject had the onset of symptoms of the *Flavivirus* infection greater than six months prior to the administration of the *Flavivirus* vaccine.

20. The method of claim 1, wherein the subject had the onset of symptoms of the *Flavivirus* infection greater than one year prior to the administration of the *Flavivirus* vaccine.

* * * * *